United States Patent
Devgon et al.

(10) Patent No.: US 11,207,498 B2
(45) Date of Patent: Dec. 28, 2021

(54) FLUID TRANSFER DEVICES WITH EXTENDED LENGTH CATHETERS AND METHODS OF USING THE SAME

(71) Applicant: Velano Vascular, Inc., San Francisco, CA (US)

(72) Inventors: Pitamber Devgon, Philadelphia, PA (US); Brian J. Funk, San Francisco, CA (US); Evan Vandenbrink, Burlingame, CA (US)

(73) Assignee: Velano Vascular, Inc., San Francisco, CA (US)

( * ) Notice: Subject to any disclaimer, the term of this patent is extended or adjusted under 35 U.S.C. 154(b) by 0 days.

(21) Appl. No.: 16/998,697

(22) Filed: Aug. 20, 2020

(65) Prior Publication Data
US 2021/0052851 A1    Feb. 25, 2021

Related U.S. Application Data

(60) Provisional application No. 62/889,252, filed on Aug. 20, 2019.

(51) Int. Cl.
| | | |
|---|---|---|
| *A61M 25/01* | (2006.01) | |
| *A61M 39/02* | (2006.01) | |
| *A61M 25/00* | (2006.01) | |

(52) U.S. Cl.
CPC .... *A61M 25/0113* (2013.01); *A61M 39/0247* (2013.01); *A61M 25/002* (2013.01);
(Continued)

(58) Field of Classification Search
CPC .......... A61M 25/0113; A61M 39/0247; A61M 25/002; A61M 2039/0258;
(Continued)

(56) References Cited

U.S. PATENT DOCUMENTS

| 3,262,448 A | 7/1966 | Ring et al. |
|---|---|---|
| 3,766,913 A | 10/1973 | Moorehead et al. |

(Continued)

FOREIGN PATENT DOCUMENTS

| CN | 101884823 A | 11/2010 |
|---|---|---|
| EP | 1191970 B1 | 3/2006 |

(Continued)

OTHER PUBLICATIONS

Office Action for U.S. Appl. No. 13/234,857, dated Apr. 16, 2015, 17 pgs.

(Continued)

*Primary Examiner* — Nathan R Price
*Assistant Examiner* — Melissa A Snyder
(74) *Attorney, Agent, or Firm* — The Webb Law Firm

(57) ABSTRACT

An apparatus includes a housing, a catheter, and an actuator. The housing has a first port and a second port that is coupleable to an indwelling vascular access device. The catheter is at least partially disposed in the housing such that the first port of the housing receives a proximal end portion of the catheter. The actuator is partially disposed in the housing to selectively engage a portion of the catheter in the housing. The actuator is configured to be rotated an angular distance relative to the housing to move a distal end portion of the catheter a linear distance from a first position inside the housing, to a second position in which the catheter extends through the second port and distal to the indwelling vascular access device when the second port is coupled thereto. The linear distance is greater than the angular distance.

22 Claims, 22 Drawing Sheets

(52) U.S. Cl.
CPC ............. *A61M 2039/0258* (2013.01); *A61M 2039/0273* (2013.01); *A61M 2039/0276* (2013.01)

(58) Field of Classification Search
CPC .. A61M 2039/0273; A61M 2039/0276; A61M 25/0136
See application file for complete search history.

(56) References Cited

U.S. PATENT DOCUMENTS

| | | | |
|---|---|---|---|
| 3,835,854 A * | 9/1974 | Jewett | A61M 25/0113 604/159 |
| 4,068,659 A | 1/1978 | Moorehead | |
| 4,159,022 A | 6/1979 | Pevsner | |
| 4,192,319 A | 3/1980 | Hargens et al. | |
| 4,314,555 A | 2/1982 | Sagae | |
| 4,342,313 A * | 8/1982 | Chittenden | A61M 25/0113 604/159 |
| 4,705,511 A | 11/1987 | Kocak | |
| 4,790,830 A | 12/1988 | Hamacher | |
| 4,808,158 A | 2/1989 | Kreuzer et al. | |
| 4,808,165 A | 2/1989 | Carr | |
| 4,935,010 A | 6/1990 | Cox et al. | |
| 4,976,697 A | 12/1990 | Walder et al. | |
| 5,013,304 A | 5/1991 | Russell et al. | |
| 5,057,092 A | 10/1991 | Webster, Jr. | |
| 5,069,674 A | 12/1991 | Fearnot et al. | |
| 5,100,390 A | 3/1992 | Lubeck et al. | |
| 5,135,502 A | 8/1992 | Koenig, Jr. et al. | |
| 5,147,334 A | 9/1992 | Moss | |
| 5,201,722 A | 4/1993 | Moorehead et al. | |
| 5,203,771 A | 4/1993 | Melker et al. | |
| 5,254,107 A | 10/1993 | Soltesz | |
| 5,270,003 A | 12/1993 | Bernes et al. | |
| 5,360,407 A | 11/1994 | Leonard | |
| 5,368,029 A | 11/1994 | Holcombe et al. | |
| 5,405,323 A | 4/1995 | Rogers et al. | |
| 5,415,636 A | 5/1995 | Forman | |
| 5,552,118 A | 9/1996 | Mayer | |
| 5,553,625 A | 9/1996 | Rao | |
| 5,562,631 A | 10/1996 | Bogert | |
| 5,603,706 A | 2/1997 | Wyatt et al. | |
| 5,611,782 A | 3/1997 | Haedt | |
| 5,658,263 A | 8/1997 | Dang et al. | |
| 5,704,914 A | 1/1998 | Stocking et al. | |
| 5,713,876 A | 2/1998 | Bogert et al. | |
| 5,749,857 A | 5/1998 | Cuppy | |
| 5,755,709 A | 5/1998 | Cuppy | |
| 5,807,350 A | 9/1998 | Diaz | |
| 5,810,835 A * | 9/1998 | Ryan | A61M 25/0084 604/159 |
| 5,827,229 A | 10/1998 | Auth et al. | |
| 5,848,996 A | 12/1998 | Eldor | |
| 5,853,393 A | 12/1998 | Bogert | |
| 5,897,537 A | 4/1999 | Berg et al. | |
| 5,911,715 A | 6/1999 | Berg et al. | |
| 5,944,690 A | 8/1999 | Falwell et al. | |
| 5,944,695 A | 8/1999 | Johnson et al. | |
| 6,036,677 A | 3/2000 | Javier, Jr. et al. | |
| 6,059,759 A | 5/2000 | Mottola et al. | |
| 6,080,138 A | 6/2000 | Lemke et al. | |
| 6,093,177 A | 7/2000 | Javier et al. | |
| 6,126,618 A | 10/2000 | Bischof | |
| 6,197,001 B1 | 3/2001 | Wilson et al. | |
| 6,213,978 B1 | 4/2001 | Voyten | |
| 6,394,979 B1 | 5/2002 | Sharp et al. | |
| 6,508,790 B1 | 1/2003 | Lawrence | |
| 6,585,703 B1 | 7/2003 | Kassel et al. | |
| 6,648,835 B1 | 11/2003 | Shemesh | |
| 6,652,507 B2 | 11/2003 | Pepin | |
| 6,685,664 B2 | 2/2004 | Levin et al. | |
| 6,692,473 B2 | 2/2004 | St Cyr et al. | |
| 6,712,790 B1 | 3/2004 | Prestidge et al. | |
| 6,719,726 B2 | 4/2004 | Meng et al. | |
| 6,719,781 B1 | 4/2004 | Kim | |
| 6,722,370 B1 | 4/2004 | Mann | |
| 6,726,675 B1 | 4/2004 | Beyar | |
| 6,755,812 B2 | 6/2004 | Peterson et al. | |
| 6,858,024 B1 | 2/2005 | Berg et al. | |
| 6,872,193 B2 | 3/2005 | Shaw et al. | |
| 6,908,459 B2 | 6/2005 | Harding et al. | |
| 6,913,595 B2 | 7/2005 | Mastorakis | |
| 7,008,404 B2 | 3/2006 | Nakajima | |
| 7,087,047 B2 | 8/2006 | Kraus et al. | |
| 7,135,008 B2 | 11/2006 | O'Mahony et al. | |
| 7,252,654 B2 | 8/2007 | VanTassel et al. | |
| 7,311,689 B2 | 12/2007 | Levin et al. | |
| 7,316,678 B2 | 1/2008 | Nash et al. | |
| 7,462,161 B2 | 12/2008 | O'Mahony et al. | |
| 7,615,033 B2 | 11/2009 | Leong | |
| 7,625,367 B2 | 12/2009 | Adams et al. | |
| 7,662,110 B2 | 2/2010 | Flaherty | |
| 7,670,320 B2 | 3/2010 | Iwase et al. | |
| 7,685,367 B2 | 3/2010 | Ruia et al. | |
| 7,691,088 B2 | 4/2010 | Howell | |
| 7,713,250 B2 | 5/2010 | Harding et al. | |
| 7,717,882 B2 | 5/2010 | Harding | |
| 7,717,899 B2 | 5/2010 | Bowe et al. | |
| 7,762,977 B2 | 7/2010 | Porter et al. | |
| 7,766,961 B2 | 8/2010 | Patel et al. | |
| 7,771,394 B2 | 8/2010 | Shue et al. | |
| 7,892,208 B2 | 2/2011 | Schnell et al. | |
| 7,972,294 B2 | 7/2011 | Nash et al. | |
| 8,048,031 B2 | 11/2011 | Shaw et al. | |
| 8,062,226 B2 | 11/2011 | Moore | |
| 8,092,374 B2 | 1/2012 | Smith et al. | |
| 8,104,475 B2 | 1/2012 | Cheung | |
| 8,114,057 B2 | 2/2012 | Gerdts et al. | |
| 8,162,890 B2 | 4/2012 | Amisar et al. | |
| 8,211,089 B2 | 7/2012 | Winsor et al. | |
| 8,251,978 B2 | 8/2012 | Nash et al. | |
| 8,267,911 B2 | 9/2012 | Gallogly et al. | |
| 8,328,759 B2 | 12/2012 | Donawick | |
| 8,361,013 B2 | 1/2013 | Wood, Jr. | |
| 8,361,014 B2 | 1/2013 | Wood, Jr. | |
| 8,366,685 B2 | 2/2013 | Devgon | |
| 8,372,032 B2 | 2/2013 | Wood, Jr. | |
| 8,425,532 B2 | 4/2013 | Flom et al. | |
| 8,444,605 B2 | 5/2013 | Kuracina et al. | |
| 8,491,568 B2 | 7/2013 | Schertiger et al. | |
| 8,500,054 B2 * | 8/2013 | Grant | A61M 39/08 242/388.1 |
| 8,506,533 B2 | 8/2013 | Carlyon et al. | |
| 8,523,801 B2 | 9/2013 | Nash et al. | |
| 8,532,730 B2 | 9/2013 | Brister et al. | |
| 8,690,833 B2 | 4/2014 | Belson | |
| 8,696,639 B2 | 4/2014 | Smith et al. | |
| 8,702,658 B2 | 4/2014 | Spearman | |
| 8,721,546 B2 | 5/2014 | Belson | |
| 8,728,035 B2 | 5/2014 | Warring et al. | |
| 8,728,038 B2 | 5/2014 | Spearman | |
| 8,728,058 B2 | 5/2014 | Schertiger | |
| 8,753,312 B2 | 6/2014 | Bowe et al. | |
| 8,808,246 B2 | 8/2014 | Cabot | |
| 8,876,773 B2 | 11/2014 | Ishida | |
| 8,932,259 B2 | 1/2015 | Stout et al. | |
| 8,936,581 B2 | 1/2015 | Bihlmaier | |
| 8,974,411 B2 | 3/2015 | Mckinnon | |
| 9,028,425 B2 | 5/2015 | Burkholz | |
| 9,056,182 B2 | 6/2015 | Moulton et al. | |
| 9,084,851 B2 | 7/2015 | Kosinski et al. | |
| 9,089,474 B2 | 7/2015 | Cederschiöld | |
| 9,101,746 B2 | 8/2015 | Stout et al. | |
| 9,114,241 B2 | 8/2015 | Stout et al. | |
| 9,126,012 B2 | 9/2015 | McKinnon et al. | |
| 9,149,604 B2 | 10/2015 | Nishide et al. | |
| 9,155,876 B2 | 10/2015 | Sonderegger et al. | |
| 9,186,100 B2 | 11/2015 | Devgon | |
| 9,198,610 B2 | 12/2015 | Davis et al. | |
| 9,220,871 B2 | 12/2015 | Thörne et al. | |
| 9,233,208 B2 | 1/2016 | Tekeste | |
| 9,302,049 B2 | 4/2016 | Tekeste | |
| 9,314,201 B2 | 4/2016 | Burkholz et al. | |

(56) References Cited

U.S. PATENT DOCUMENTS

| | | |
|---|---|---|
| 9,352,119 B2 | 5/2016 | Burkholz et al. |
| 9,352,128 B2 | 5/2016 | Ishida |
| 9,358,335 B2 | 6/2016 | Wada et al. |
| 9,381,320 B2 | 7/2016 | Vincent et al. |
| 9,399,112 B2 | 7/2016 | Shevgoor et al. |
| 9,402,975 B2 | 8/2016 | Shevgoor |
| 9,408,569 B2 | 8/2016 | Andreae et al. |
| 9,415,185 B2 | 8/2016 | Notter |
| 9,480,794 B2 | 11/2016 | Keith et al. |
| 9,522,229 B2 | 12/2016 | Sonderegger et al. |
| 9,522,237 B2 | 12/2016 | Alheidt et al. |
| 9,549,701 B2 | 1/2017 | Peterson et al. |
| 9,579,486 B2 | 2/2017 | Burkholz et al. |
| 9,592,374 B2 | 3/2017 | Muse |
| 9,616,214 B2 | 4/2017 | Stout et al. |
| 9,636,278 B2 | 5/2017 | Sanders et al. |
| 9,737,686 B2 | 8/2017 | Trainer et al. |
| 9,744,344 B1 | 8/2017 | Devgon et al. |
| 9,750,446 B2 | 9/2017 | Devgon et al. |
| 9,750,920 B2 | 9/2017 | Vincent et al. |
| 9,750,927 B2 | 9/2017 | Ma |
| 9,750,928 B2 | 9/2017 | Burkholz et al. |
| 9,770,580 B2 | 9/2017 | Burkholz et al. |
| 9,775,972 B2 | 10/2017 | Christensen et al. |
| 9,789,279 B2 | 10/2017 | Burkholz et al. |
| 9,832,412 B2 | 11/2017 | Burkholz et al. |
| 9,839,385 B2 | 12/2017 | Burkholz |
| 9,895,092 B2 | 2/2018 | Burkholz |
| 9,907,913 B2 | 3/2018 | Kosinski et al. |
| 9,909,162 B2 | 3/2018 | Yeh |
| 9,919,826 B2 | 3/2018 | Ivosevic et al. |
| 9,943,676 B2 | 4/2018 | Tekeste |
| 9,980,878 B2 | 5/2018 | Marici et al. |
| 9,993,634 B2 | 6/2018 | Christensen et al. |
| 10,010,685 B2 | 7/2018 | Ferreri et al. |
| 10,022,530 B2 | 7/2018 | Tekeste |
| 10,039,884 B2 | 8/2018 | Ferreri et al. |
| 10,046,155 B2 | 8/2018 | Carter et al. |
| 10,076,272 B2 | 9/2018 | Devgon et al. |
| 10,086,142 B2 | 10/2018 | Tekeste |
| 10,105,085 B2 | 10/2018 | Andreae et al. |
| 10,105,494 B2 | 10/2018 | Alheidt et al. |
| 10,112,033 B2 | 10/2018 | Burkholz et al. |
| 10,143,411 B2 | 12/2018 | Cabot |
| 10,182,753 B2 | 1/2019 | Davis et al. |
| 10,219,982 B2 | 3/2019 | Weir et al. |
| 10,232,088 B2 | 3/2019 | Burkholz et al. |
| 10,232,140 B2 | 3/2019 | McKinnon |
| 10,238,325 B2 | 3/2019 | Burkholz et al. |
| 10,238,852 B2 | 3/2019 | Burkholz et al. |
| 10,245,416 B2 | 4/2019 | Harding et al. |
| 10,272,237 B2 | 4/2019 | Stout et al. |
| 10,300,247 B2 | 5/2019 | Devgon et al. |
| 10,307,571 B2 | 6/2019 | Burkholz |
| 10,350,066 B2* | 7/2019 | Cooper ............. A61M 25/0051 |
| 10,357,636 B2 | 7/2019 | Sonderegger et al. |
| 10,391,031 B2 | 8/2019 | Yevmenenko et al. |
| 10,426,929 B2 | 10/2019 | Burkholz et al. |
| 10,729,367 B1 | 8/2020 | Devgon |
| 10,773,056 B2 | 9/2020 | Funk et al. |
| 2002/0120215 A1 | 8/2002 | Crawford et al. |
| 2003/0009150 A1 | 1/2003 | Pepin |
| 2003/0083620 A1 | 5/2003 | Luther et al. |
| 2003/0122021 A1* | 7/2003 | McConnell ............. H02G 11/02 242/388.1 |
| 2003/0225369 A1 | 12/2003 | McMichael et al. |
| 2004/0092879 A1 | 5/2004 | Kraus et al. |
| 2004/0138622 A1 | 7/2004 | Palasis |
| 2004/0181192 A1 | 9/2004 | Cuppy |
| 2005/0015048 A1 | 1/2005 | Chiu et al. |
| 2005/0090801 A1 | 4/2005 | Racz et al. |
| 2005/0096609 A1 | 5/2005 | Maginot et al. |
| 2005/0119597 A1 | 6/2005 | O'Mahony et al. |
| 2005/0165355 A1 | 7/2005 | Fitzgerald |
| 2005/0192558 A1 | 9/2005 | Bernard et al. |
| 2005/0197623 A1* | 9/2005 | Leeflang ............. A61B 1/00078 604/95.04 |
| 2005/0267327 A1* | 12/2005 | Iizuka .................... A61B 17/29 600/106 |
| 2005/0273076 A1 | 12/2005 | Beasley et al. |
| 2006/0015068 A1 | 1/2006 | Amisar et al. |
| 2006/0100582 A1 | 5/2006 | Marianowicz et al. |
| 2006/0142694 A1 | 6/2006 | Bednarek et al. |
| 2006/0155209 A1 | 7/2006 | Miller et al. |
| 2006/0155244 A1 | 7/2006 | Popov |
| 2007/0088279 A1 | 4/2007 | Shue et al. |
| 2007/0100295 A1 | 5/2007 | Belley et al. |
| 2007/0219460 A1 | 9/2007 | Goldenberg |
| 2007/0282280 A1 | 12/2007 | Tennican |
| 2008/0033396 A1 | 2/2008 | Danek et al. |
| 2008/0045862 A1 | 2/2008 | Dalebout et al. |
| 2008/0097407 A1 | 4/2008 | Pishka |
| 2008/0287918 A1 | 11/2008 | Rosenman et al. |
| 2008/0300574 A1 | 12/2008 | Belson et al. |
| 2008/0319387 A1 | 12/2008 | Amisar et al. |
| 2009/0156963 A1 | 6/2009 | Noble et al. |
| 2009/0192496 A1 | 7/2009 | Suwito et al. |
| 2009/0209912 A1 | 8/2009 | Keyser et al. |
| 2010/0121218 A1 | 5/2010 | Mugan et al. |
| 2010/0160863 A1 | 6/2010 | Heuser |
| 2010/0210934 A1 | 8/2010 | Belson |
| 2010/0286657 A1 | 11/2010 | Heck |
| 2010/0305519 A1 | 12/2010 | McKinnon et al. |
| 2011/0015577 A1 | 1/2011 | Baney et al. |
| 2011/0202123 A1 | 8/2011 | Bonutti |
| 2012/0016307 A1 | 1/2012 | Burkholz et al. |
| 2012/0041392 A1 | 2/2012 | Donawick |
| 2012/0046648 A1 | 2/2012 | Scheckel |
| 2012/0053523 A1 | 3/2012 | Harding |
| 2012/0109079 A1 | 5/2012 | Asleson et al. |
| 2012/0157968 A1 | 6/2012 | Eldredge et al. |
| 2012/0191010 A1 | 7/2012 | Cabot |
| 2012/0197200 A1 | 8/2012 | Belson |
| 2012/0277627 A1 | 11/2012 | Devgon |
| 2013/0006226 A1 | 1/2013 | Hong et al. |
| 2013/0102888 A1 | 4/2013 | Slim |
| 2013/0121897 A1 | 5/2013 | Davis et al. |
| 2013/0131597 A1 | 5/2013 | Blaivas et al. |
| 2013/0281925 A1 | 10/2013 | Benscoter et al. |
| 2013/0289537 A1 | 10/2013 | Schertiger et al. |
| 2014/0012085 A1 | 1/2014 | Smith et al. |
| 2014/0107427 A1 | 4/2014 | Chow et al. |
| 2014/0107564 A1 | 4/2014 | Bullington et al. |
| 2014/0107800 A1 | 4/2014 | Flom et al. |
| 2014/0171803 A1 | 6/2014 | Van Hoven et al. |
| 2014/0180127 A1 | 6/2014 | Meyer et al. |
| 2014/0188002 A1 | 7/2014 | Close et al. |
| 2014/0188003 A1 | 7/2014 | Belson |
| 2014/0194833 A1 | 7/2014 | Andrus |
| 2014/0296745 A1 | 10/2014 | Cash |
| 2014/0358120 A1 | 12/2014 | Haarala et al. |
| 2014/0378867 A1 | 12/2014 | Belson |
| 2015/0005669 A1 | 1/2015 | Burkholz |
| 2015/0038909 A1 | 2/2015 | Christensen et al. |
| 2015/0051584 A1* | 2/2015 | Korkuch ........... A61M 25/0606 604/510 |
| 2015/0065952 A1 | 3/2015 | Pacheco et al. |
| 2015/0119859 A1 | 4/2015 | Cajamarca et al. |
| 2015/0119863 A1 | 4/2015 | Christensen et al. |
| 2015/0123398 A1 | 5/2015 | Sanders et al. |
| 2015/0148747 A1 | 5/2015 | Whitley |
| 2015/0208973 A1 | 7/2015 | Burkholz |
| 2015/0209510 A1 | 7/2015 | Burkholz et al. |
| 2015/0297456 A1 | 10/2015 | Marici et al. |
| 2015/0305981 A1 | 10/2015 | Cederschiöld |
| 2015/0306345 A1 | 10/2015 | Burkholz et al. |
| 2015/0313526 A1 | 11/2015 | Van Wieren |
| 2015/0320937 A1 | 11/2015 | Kosinski et al. |
| 2015/0360005 A1 | 12/2015 | Arellano et al. |
| 2016/0008517 A1 | 1/2016 | Burkholz et al. |
| 2016/0015945 A1 | 1/2016 | Warring et al. |
| 2016/0038067 A1 | 2/2016 | Davis et al. |
| 2016/0073937 A1 | 3/2016 | Burkholz et al. |
| 2016/0121086 A1 | 5/2016 | Castro et al. |

(56) References Cited

U.S. PATENT DOCUMENTS

| | | |
|---|---|---|
| 2016/0166772 A1 | 6/2016 | Mirzazadeh et al. |
| 2016/0206858 A1 | 7/2016 | Ishida |
| 2016/0220786 A1 | 8/2016 | Mitchell et al. |
| 2016/0220790 A1 | 8/2016 | Borowicz |
| 2016/0256667 A1 | 9/2016 | Ribelin et al. |
| 2016/0325078 A1 | 11/2016 | Burkholz |
| 2016/0367177 A1 | 12/2016 | Edelhauser et al. |
| 2017/0043066 A1 | 2/2017 | Laub |
| 2017/0056595 A1 | 3/2017 | Alheidt et al. |
| 2017/0056639 A1 | 3/2017 | Ma |
| 2017/0119997 A1 | 5/2017 | Burkholz et al. |
| 2017/0120001 A1 | 5/2017 | Hyer et al. |
| 2017/0120008 A1 | 5/2017 | Burkholz et al. |
| 2017/0120009 A1 | 5/2017 | Garrison et al. |
| 2017/0120010 A1 | 5/2017 | Burkholz et al. |
| 2017/0120012 A1 | 5/2017 | Sonderegger et al. |
| 2017/0120013 A1 | 5/2017 | Peterson et al. |
| 2017/0120017 A1 | 5/2017 | Burkholz et al. |
| 2017/0273714 A1 | 9/2017 | Harding et al. |
| 2017/0325713 A1 | 11/2017 | Burkholz et al. |
| 2017/0333676 A1 | 11/2017 | Vincent et al. |
| 2017/0368326 A1 | 12/2017 | Burkholz et al. |
| 2018/0021543 A1 | 1/2018 | Burkholz et al. |
| 2018/0093074 A1 | 4/2018 | Burkholz et al. |
| 2018/0093085 A1 | 4/2018 | Burkholz et al. |
| 2018/0272106 A1 | 9/2018 | Funk et al. |
| 2018/0272107 A1 | 9/2018 | Ehrenreich et al. |
| 2018/0280626 A1 | 10/2018 | Branson et al. |
| 2018/0289920 A1 | 10/2018 | Harding et al. |
| 2018/0289921 A1 | 10/2018 | Burkholz |
| 2018/0289922 A1 | 10/2018 | Burkholz |
| 2018/0318557 A1 | 11/2018 | Burkholz et al. |
| 2018/0353311 A1* | 12/2018 | Cummins ............... A61F 2/962 |
| 2018/0353729 A1 | 12/2018 | Hu et al. |
| 2019/0021640 A1 | 1/2019 | Burkholz et al. |
| 2019/0022324 A1 | 1/2019 | Tekeste |
| 2019/0022357 A1 | 1/2019 | Burkholz et al. |
| 2019/0022367 A1 | 1/2019 | Burkholz et al. |
| 2019/0054270 A1 | 2/2019 | Bornhoft |
| 2019/0091462 A1 | 3/2019 | Bihlmaier et al. |
| 2019/0105464 A1 | 4/2019 | Naidu et al. |
| 2019/0167855 A1 | 6/2019 | Burkholz et al. |
| 2019/0167951 A1 | 6/2019 | Harding et al. |
| 2019/0167966 A1 | 6/2019 | Burkholz et al. |
| 2019/0175088 A1 | 6/2019 | Burkholz et al. |
| 2019/0209726 A1 | 7/2019 | Ma et al. |
| 2019/0209812 A1 | 7/2019 | Burkholz et al. |
| 2019/0269889 A1 | 9/2019 | Ma et al. |
| 2019/0321590 A1 | 10/2019 | Burkholz et al. |
| 2019/0321595 A1 | 10/2019 | Spataro et al. |
| 2019/0366052 A1 | 12/2019 | Burkholz et al. |
| 2020/0016374 A1 | 1/2020 | Burkholz et al. |
| 2020/0023176 A1 | 1/2020 | Hu et al. |
| 2020/0078564 A1 | 3/2020 | Blanchard et al. |
| 2020/0078579 A1 | 3/2020 | Harding et al. |
| 2020/0094023 A1 | 3/2020 | Isaacson et al. |
| 2020/0100716 A1 | 4/2020 | Devgon et al. |
| 2020/0230358 A1 | 7/2020 | Devgon et al. |
| 2020/0246590 A1 | 8/2020 | Devgon et al. |

FOREIGN PATENT DOCUMENTS

| | | |
|---|---|---|
| EP | 2504054 B1 | 9/2013 |
| JP | S55-119739 U | 8/1980 |
| JP | 2007-029732 A | 2/2007 |
| JP | 2010-505534 A | 2/2010 |
| RU | 2271835 C2 | 3/2006 |
| WO | WO 1996/021393 A1 | 7/1996 |
| WO | WO 1998/039054 A1 | 9/1998 |
| WO | WO 1999/016496 A1 | 4/1999 |
| WO | WO 2000/041617 A1 | 7/2000 |
| WO | WO 2000/049939 A1 | 8/2000 |
| WO | WO 2004/089437 A1 | 10/2004 |
| WO | WO 2006/065949 A2 | 6/2006 |
| WO | WO 2006/090637 A1 | 8/2006 |
| WO | WO 2006/126002 A1 | 11/2006 |
| WO | WO 2008/097949 A1 | 8/2008 |
| WO | WO 2008/130077 A1 | 10/2008 |
| WO | WO 2008/138351 A1 | 11/2008 |
| WO | WO 2009/152470 A1 | 12/2009 |
| WO | WO 2010/065901 A1 | 6/2010 |
| WO | WO 2010/089154 A1 | 8/2010 |
| WO | WO 2010/107949 A1 | 9/2010 |
| WO | WO 2011/011436 A2 | 1/2011 |
| WO | WO 2011/030282 A1 | 3/2011 |
| WO | WO 2012/064786 A1 | 5/2012 |
| WO | WO 2013/174381 A1 | 11/2013 |
| WO | WO 2014/093472 A1 | 6/2014 |
| WO | WO 2016/089871 A1 | 6/2016 |
| WO | WO 2016/178974 A1 | 11/2016 |
| WO | WO 2017/074674 A1 | 5/2017 |

OTHER PUBLICATIONS

Office Action for U.S. Appl. No. 13/456,900, dated Sep. 5, 2012, 11 pgs.
Office Action for U.S. Appl. No. 13/456,900, dated Nov. 2, 2012, 6 pgs.
Office Action for U.S. Appl. No. 13/758,585, dated Jun. 10, 2015, 20 pgs.
Office Action for U.S. Appl. No. 13/758,585, dated Oct. 30, 2015, 14 pgs.
Office Action for U.S. Appl. No. 13/758,585, dated May 16, 2016, 8 pgs.
Office Action for U.S. Appl. No. 14/468,826, dated Oct. 26, 2017, 7 pgs.
Office Action for U.S. Appl. No. 16/806,949, dated Apr. 24, 2020, 7 pgs.
Office Action for U.S. Appl. No. 15/014,834, dated May 16, 2018, 33 pgs.
Office Action for U.S. Appl. No. 15/199,290, dated Dec. 7, 2016, 32 pgs.
Office Action for U.S. Appl. No. 15/680,952, dated Dec. 6, 2017, 27 pgs.
Office Action for U.S. Appl. No. 15/927,506, dated Mar. 17, 2020, 23 pgs.
Office Action for U.S. Appl. No. 16/844,730, dated May 14, 2020, 18 pgs.
International Search Report and Written Opinion for International Application No. PCT/US2012/035122, dated Feb. 14, 2014, 8 pgs.
International Search Report and Written Opinion for International Application No. PCT/US2015/046863, dated Dec. 21, 2015, 6 pgs.
International Search Report and Written Opinion for International Application No. PCT/US2010/042635, dated Feb. 25, 2011, 7 pgs.
International Search Report and Written Opinion for International Application No. PCT/US2017/016359, dated Jun. 26, 2017, 13 pgs.
International Search Report and Written Opinion for International Application No. PCT/US2018/023479, dated Aug. 3, 2018, 10 pgs.
International Search Report and Written Opinion for International Application No. PCT/US2018/023575, dated Aug. 8, 2018, 10 pgs.
International Search Report and Written Opinion for International Application No. PCT/US2018/67631, dated Mar. 29, 2019, 10 pgs.
International Search Report and Written Opinion for International Application No. PCT/US2019/053581, dated Jan. 20, 2020, 18 pgs.
Supplementary Search Report for EP Application No. 12776089.0, dated May 13, 2015, 7 pgs.
Office Action for CN Application No. 201280029672.2, dated May 26, 2015, 21 pgs.
Office Action for JP Application No. 2014-508539, dated Feb. 26, 2016, 8 pgs.
Office Action for JP Application No. 2014-508539, dated Nov. 1, 2016, 11 pgs.
Office Action for RU Application No. 2013152251, dated Feb. 24, 2016, 14 pgs.
Notice of Preliminary Rejection for KR Application No. 10-2013-7030879, dated Feb. 6, 2018, 11 pgs.
Office Action for RU Application No. 2017109889, dated Oct. 16, 2018, 23 pgs.

(56) References Cited

OTHER PUBLICATIONS

Examination Report for AU Application No. 2015306728, dated Jul. 16, 2019, 5 pgs.
Office Action for JP Application No. 2017-038135, dated Feb. 14, 2018, 9 pgs.
Office Action for JP Application No. 2019-090357, dated Mar. 18, 2020, 12 pgs.
Extended Search Report for EP Application No. 17748206.4, dated Aug. 8, 2019, 9 pgs.
"Blood Sampling Hemolysis Study for the MaxPlus™ Positive Flow Connector," Maximus Medical Products, Inc. © 2003, 1 pg.
"Connect and Protect with BD Diagnostics—Preanalytical Systems," BD Vacutainer®, Luer-Lok™, Access Device, 2006, 2 pgs.
Cox, et al. "Blood Samples Drawn from IV Catheters Have Less Hemolysis When 5-mL (vs 10-mL) Collection Tubes Are Used," J Emerg Nurs. Dec. 2004;30(6):529-33. [Retrieved from the Internet (Mar. 16, 2011)] <URL: http://www.jenonline.org/article/S0099-1767(04)00634-8/fulltext>, 2 pgs.
"Evidence-Based Practice (EBP) Guideline Drawing Labs from Peripheral IV Sites," Nursing Research Council of United Hospital—Developed Apr. 2004; Revised Mar. 2009, 3 pgs.
Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.
Himberger Jr., "Accuracy of drawing blood through infusing intravenous lines," 2001 [retrieved on Mar. 16, 2011] Retrieved from the Internet <URL: http://www.ncbi.nlm.nih.gov/pubmed/?term=Accuracy%20of%20drawing%20blood%20through%20infusing%20intravenous%20lines>.
Jagger, et al., "Drawing Venous Blood With Syringes: A Risky Use of Injection Equipment," Advances in Exposure Prevention, vol. 5, No. 3, 2000, 3 pgs.
"Needleless IV Access Devices," BD Q-Syte™, Luer Access Split-Septum, 2007, 1 pg.
"Vascular Access Procedures," Vascular Access Procedures, [Retrieved from the Internet (Mar. 16, 2011)] <URL: http://www.radiologyinfo.org/en/info.cfm?pg=vasc_access> 7 pgs.
Velano Vascular, "Introducing PIVO" [Retrieved from the Internet] <URL: http://velanovascular.com/solutions/>, 2017.
WHO guidelines on drawing blood: best practices in phlebotomy, © World Health Organization 2010, 125 pgs.
Office Action for U.S. Appl. No. 16/945,351, dated Aug. 24, 2020, 8 pgs.
Office Action for U.S. Appl. No. 15/927,509, dated Sep. 15, 2020, 23 pgs.
Office Action for U.S. Appl. No. 16/844,730, dated Dec. 8, 2020, 25 pgs.
International Search Report and Written Opinion for International Application No. PCT/US2020/047154, dated Nov. 19, 2020, 9 pgs.

\* cited by examiner

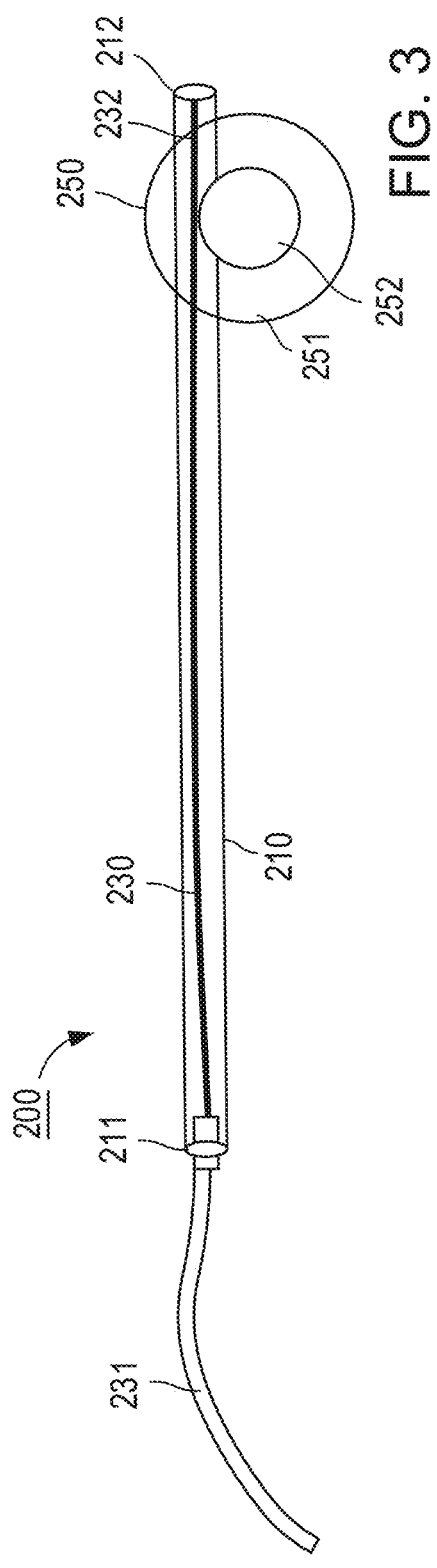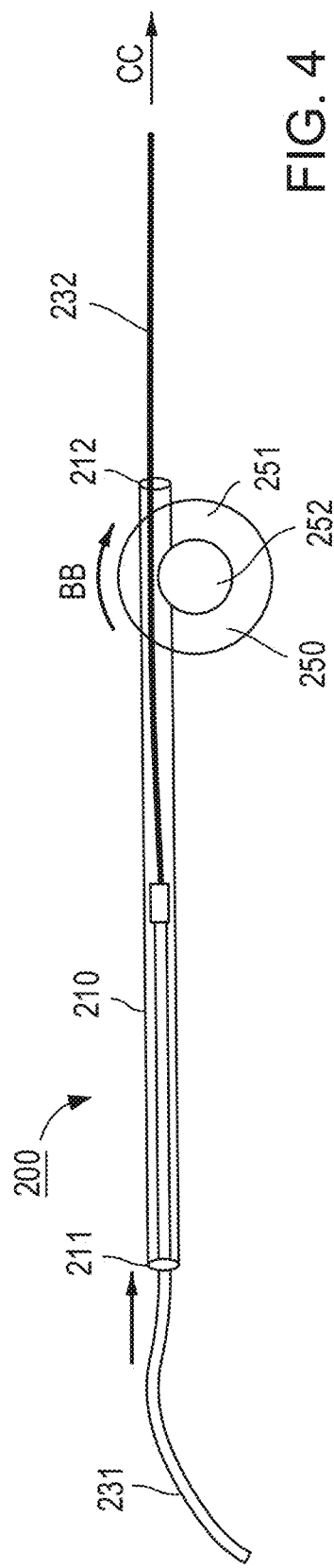

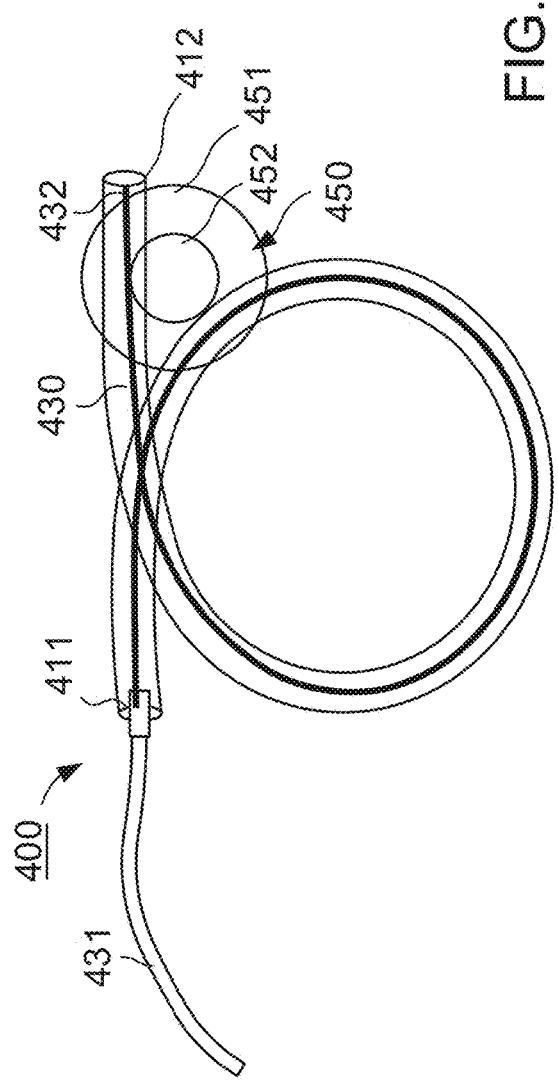
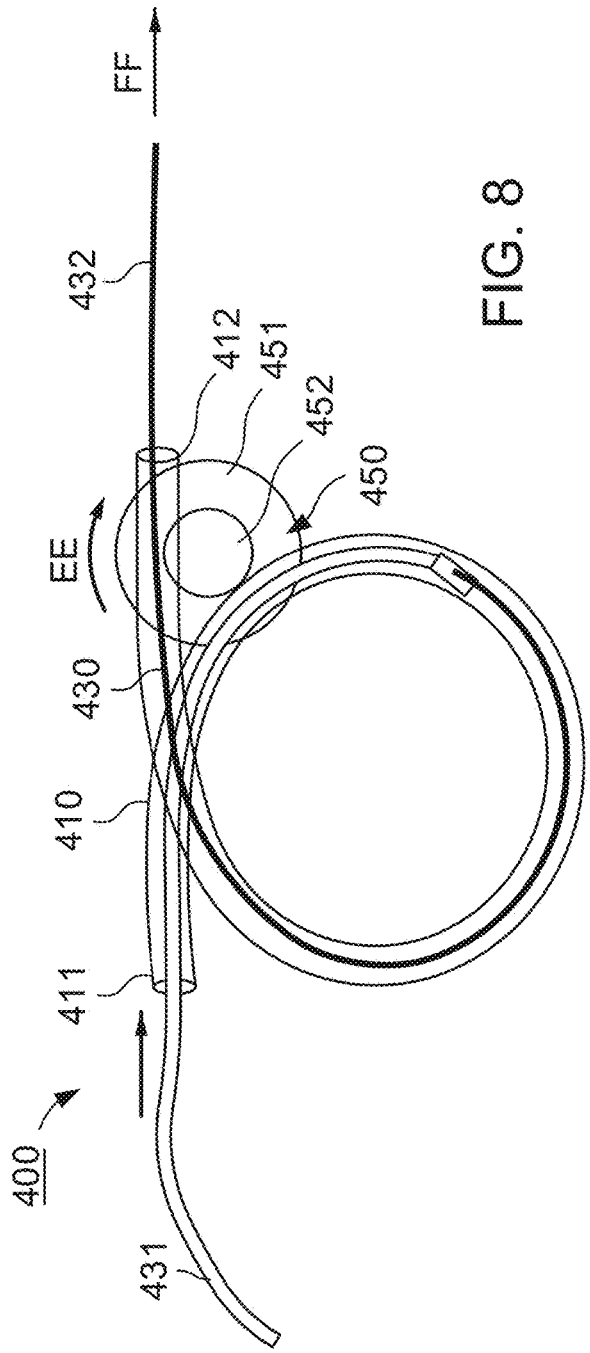

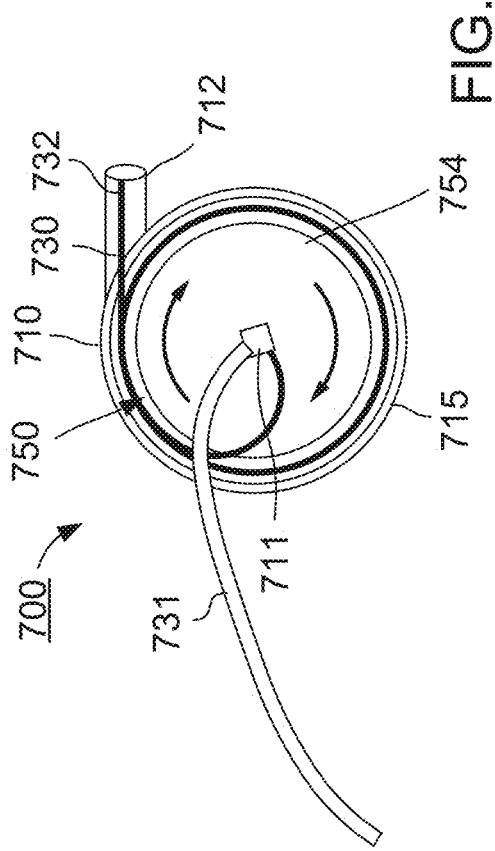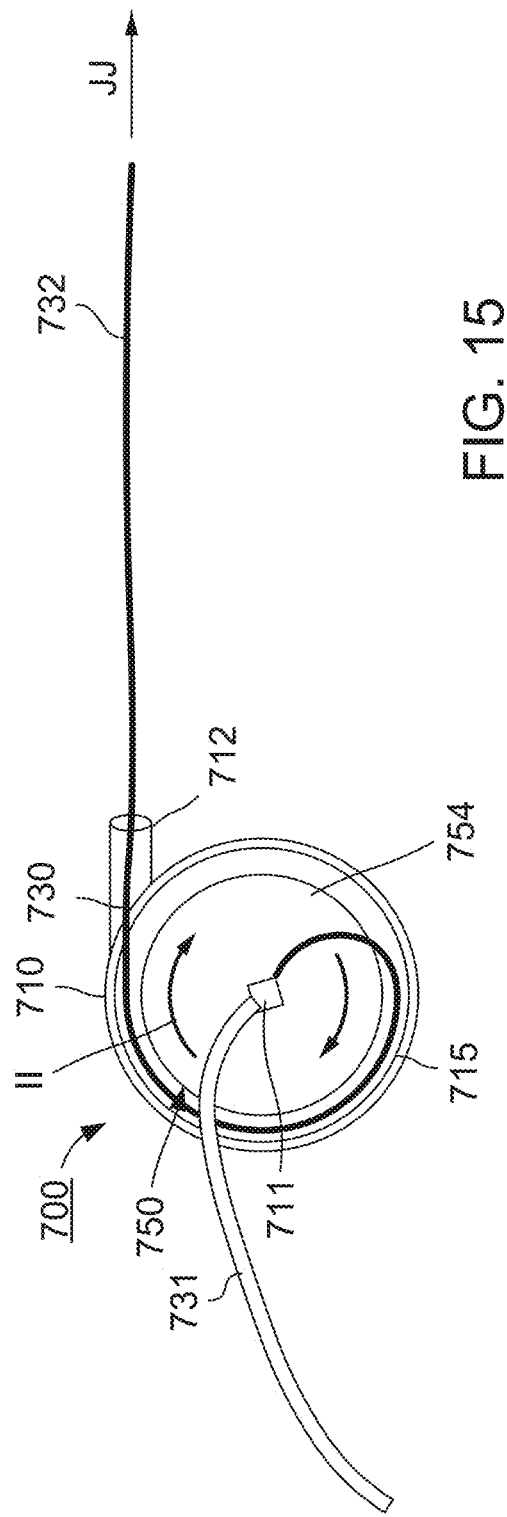

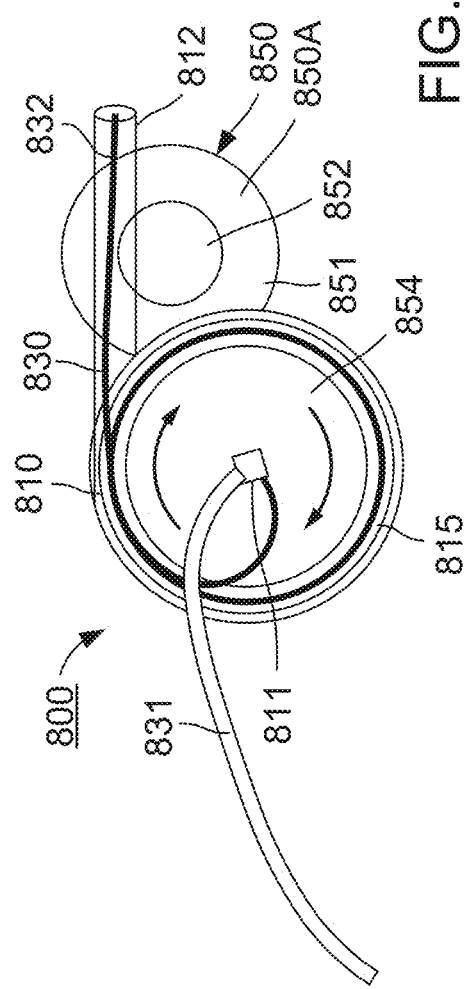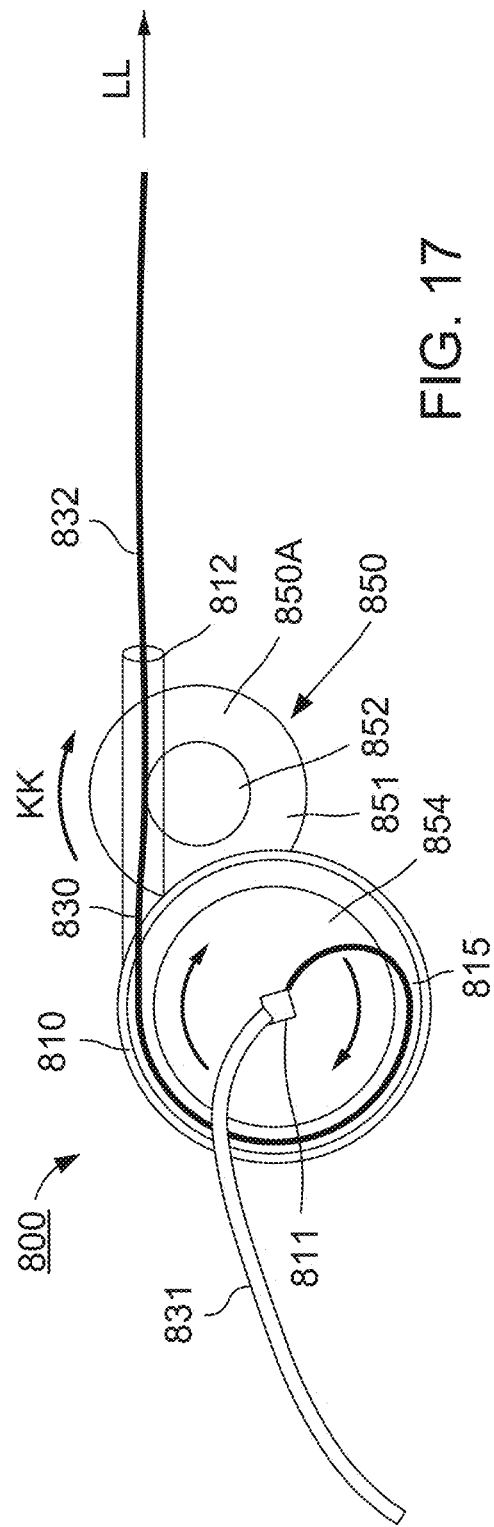

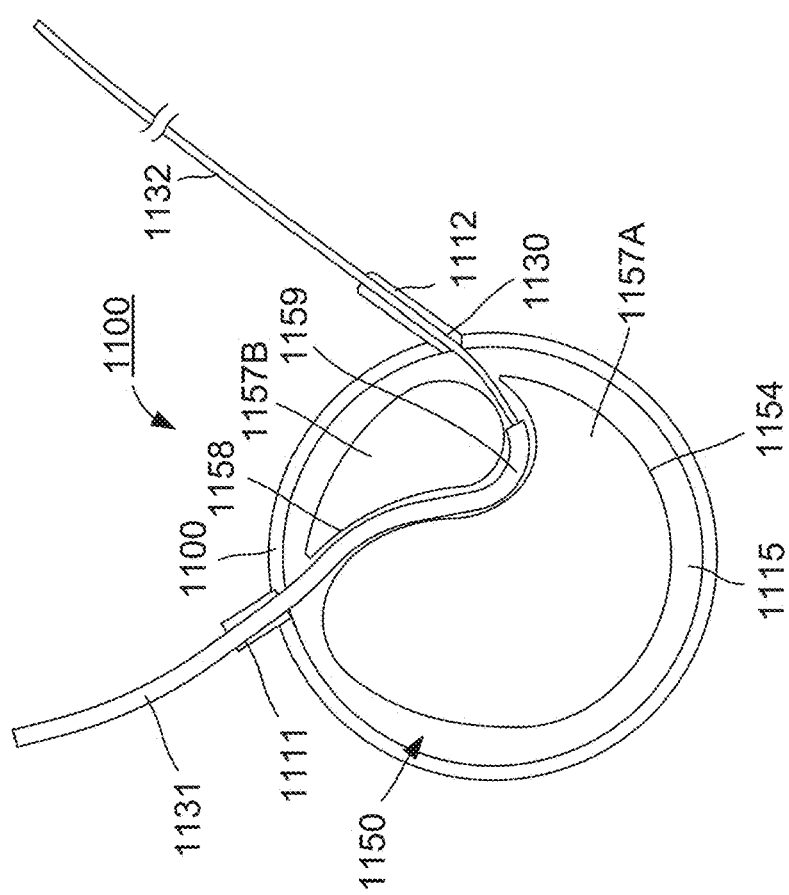
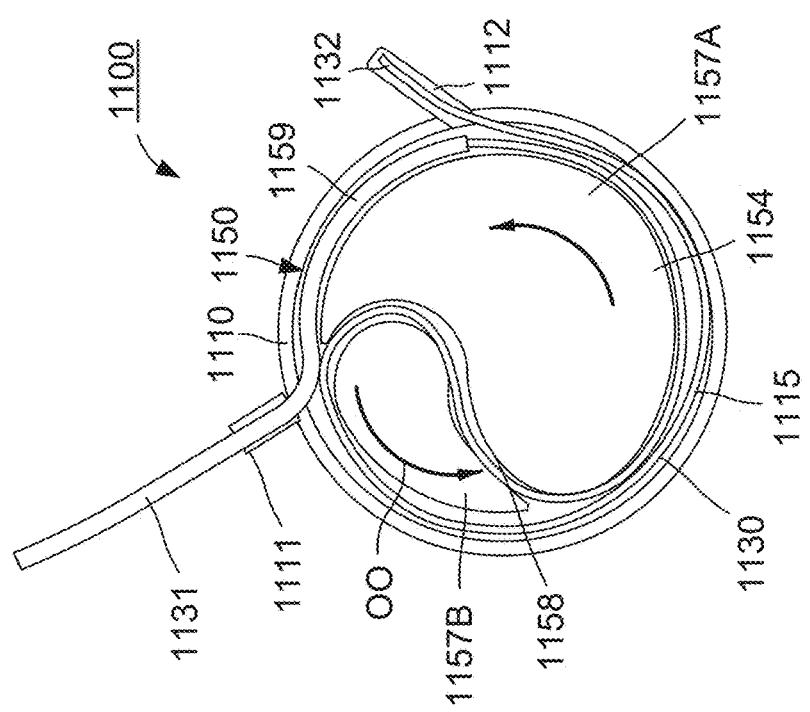

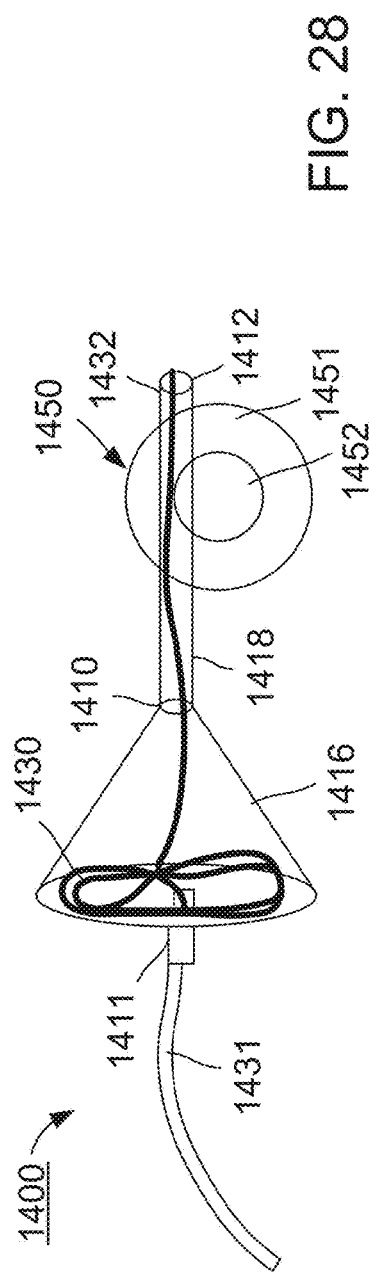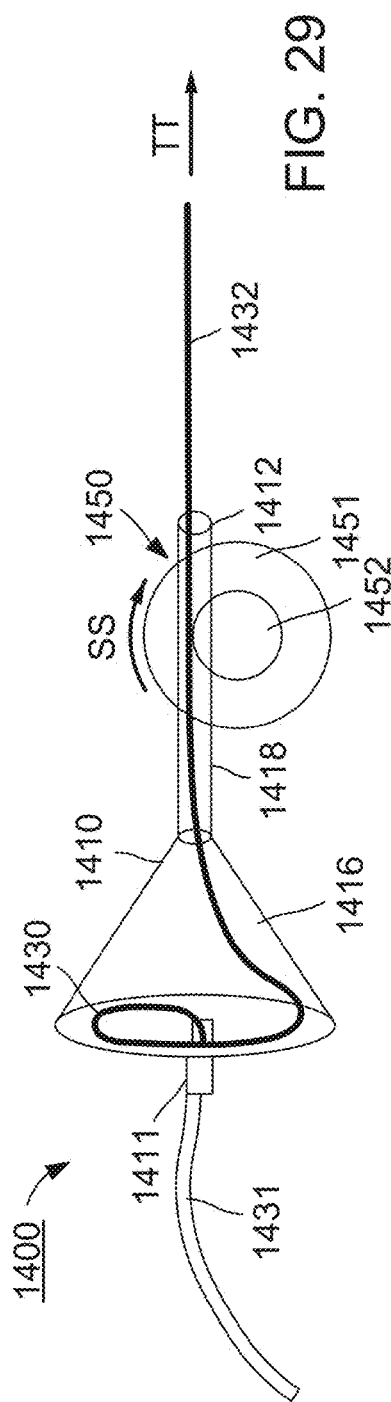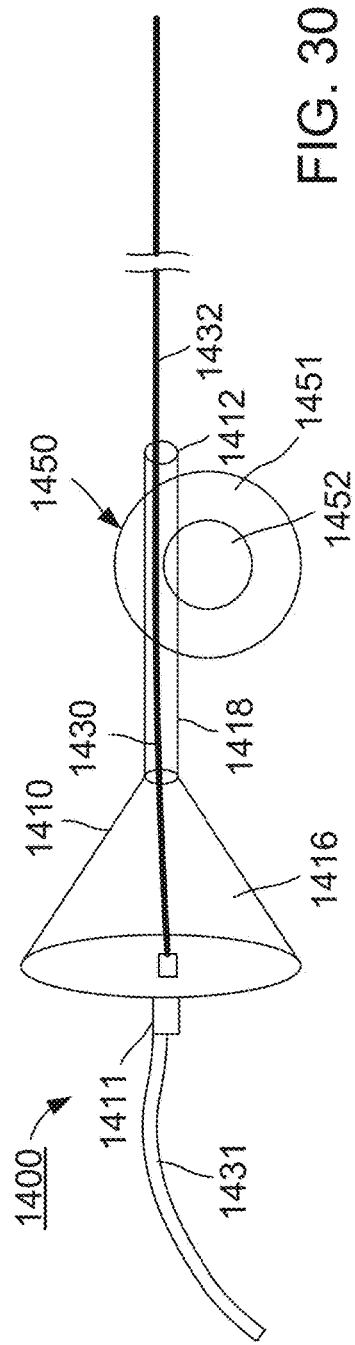

10

```
┌─────────────────────────────────────────────────────────────────────────┐
│ Couple, to an indwelling vascular access device, a second port of a     │
│ housing of a fluid transfer device having a catheter with a proximal    │
│ end portion fixedly coupled to a first port of the housing and an       │
│ actuator selectively engaging the catheter                              │
│                                   11                                    │
└─────────────────────────────────────────────────────────────────────────┘
                                    │
                                    ▼
┌─────────────────────────────────────────────────────────────────────────┐
│ Rotate the actuator of the fluid transfer device an angular distance    │
│ about a central axis defined by the housing of the fluid transfer device│
│                                   12                                    │
└─────────────────────────────────────────────────────────────────────────┘
                                    │
                                    ▼
┌─────────────────────────────────────────────────────────────────────────┐
│ Advance, in response to the rotation of the actuator, a distal end      │
│ portion of the catheter a linear distance from a first position in which│
│ the distal end portion is in the housing, to a second position in which │
│ the distal end portion is distal to the indwelling vascular access      │
│ device, the distal end portion of the catheter being advanced linearly  │
│ in a direction orthogonal to the central axis through the second port   │
│ and the indwelling vascular access device as the catheter is moved to   │
│ the second position                                                     │
│                                   13                                    │
└─────────────────────────────────────────────────────────────────────────┘
```

FLUID TRANSFER DEVICES WITH EXTENDED LENGTH CATHETERS AND METHODS OF USING THE SAME

CROSS-REFERENCE TO RELATED APPLICATIONS

This application claims priority to and the benefit of U.S. Provisional Patent Application Ser. No. 62/889,252 entitled, "Fluid Transfer Devices with Extended Length Catheters and Methods of Using the Same," filed Aug. 20, 2019, the disclosure of which is incorporated herein by reference in its entirety.

BACKGROUND

The embodiments described herein relate generally to fluid transfer devices. More particularly, the embodiments described herein relate to fluid transfer devices having a controlled size and/or catheter length.

Many medical procedures and/or surgical interventions include inserting an access device or fluid transfer device into a portion of the body. For example, catheters and/or other lumen-defining devices can be inserted into and/or through vascular structures to access portions of the body. In some instances, such catheters, access devices, and/or the like can have relatively long catheter lengths, which can present challenges during use. For example, in some instances, catheters and/or access devices used in interventional cardiology can have a length of 300 centimeters (cm) or more, which can result in the use of such devices being cumbersome and/or difficult. In addition, the length of such catheters and/or access devices can result in undesirable bending, flexing, and/or kinking.

In other instances, catheters and/or other lumen-defining devices can be used to transfer fluids from or to a patient. In some instances, it may be desirable to maintain a relatively small and/or compact form factor of such fluid transfer devices to increase ease of use and/or decrease manufacturing and/or material costs. In some such instances, however, maintaining a relatively small and/or compact form factor can result in an undesirable reduction in an effective length and/or "reach" of a catheter included in the device.

By way of example, peripheral intravenous catheters or lines (PIVs) can be inserted into a patient and used for infusing fluids and medications. In general, PIVs are not designed for blood extraction with failure rates that typically increase with indwelling times (e.g., due to obstructions, build up, debris, clots, fibrin, etc.). In some instances, however, a fluid transfer device can be coupled to a proximal portion of a PIV (e.g., the portion outside of the body) and can be used to advance a catheter through the indwelling PIV to a position in which a distal end of the catheter extends beyond a distal end of the indwelling PIV. While such devices can position the distal end of the catheter in a portion of the vein receiving a flow of blood that may otherwise be obstructed or limited due to the presence of the indwelling PIV, some such devices can have a relatively long length in order to allow for the desired placement of the catheter beyond the PIV. Moreover, the length of such devices can be further increased when the devices are configured for use with extended-dwell or midline PIVs, and/or peripherally inserted central catheters (PICCs).

Thus, a need exists for compact fluid transfer devices have a controllable size and/or catheter length.

SUMMARY

Devices and methods for transferring fluid to or from a patient through a placed peripheral intravenous catheter using a relatively compact device are described herein. In some embodiments, an apparatus includes a housing, a catheter, and an actuator. The housing has a first port and a second port that is coupleable to an indwelling vascular access device. The catheter has a proximal end portion and a distal end portion, and it is at least partially disposed in the housing such that the first port of the housing receives the proximal end portion of the catheter. The actuator is partially disposed in the housing to selectively engage a portion of the catheter in the housing. The actuator is configured to be rotated an angular distance relative to the housing to move the distal end portion of the catheter a linear distance from a first position in which the distal end portion of the catheter is disposed in the housing, to a second position in which the catheter extends through the second port such that the distal end portion of the catheter is distal to the indwelling vascular access device when the second port is coupled to the indwelling vascular access device. The linear distance is greater than the angular distance.

BRIEF DESCRIPTION OF THE DRAWINGS

FIGS. 3 and 4 are schematic illustrations of a fluid transfer device, in a first configuration and a second configuration, respectively, according to an embodiment.

FIGS. 7 and 8 are schematic illustrations of a fluid transfer device in a first configuration and a second configuration, respectively, according to an embodiment.

FIGS. 14 and 15 are schematic illustrations of a fluid transfer device in a first configuration and a second configuration, respectively, according to an embodiment.

FIGS. 16 and 17 are schematic illustrations of a fluid transfer device in a first configuration and a second configuration, respectively, according to an embodiment.

FIGS. 24 and 25 are schematic illustrations of a fluid transfer device in a first configuration and a second configuration, respectively, according to an embodiment.

FIGS. 28-30 are schematic illustrations of a fluid transfer device as the fluid transfer device transitions from a first configuration (FIG. 28) to a second configuration (FIG. 30), according to an embodiment.

FIG. 40 is a flow chart illustrating a method of using the fluid transfer device according to an embodiment.

DETAILED DESCRIPTION

Figure 1:
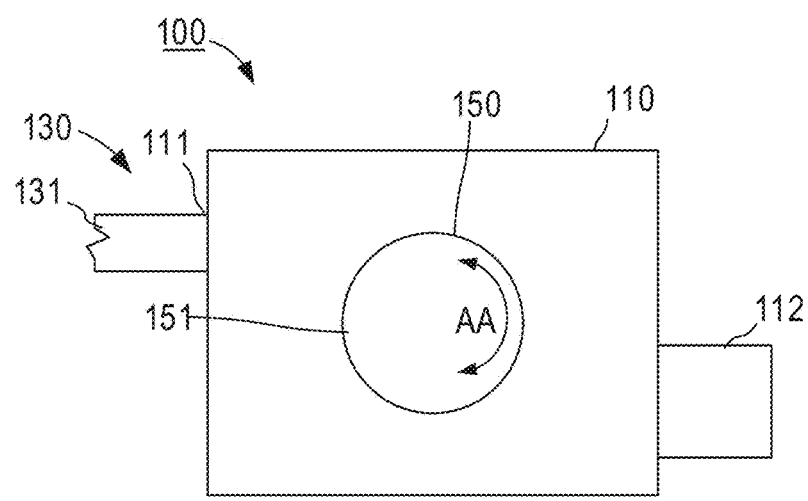
FIGS. 1 and 2 are schematic illustrations of a fluid transfer device in a first configuration and a second configuration, respectively, according to an embodiment.

The embodiments described herein can be used in any suitable medical procedure and/or surgical intervention. For example, in some embodiments, a device such as those described herein can be used as an access device or the like during surgical intervention. In other embodiments, a device such as those described herein can be used to transfer fluids between a patient and any external connection, fluid source, fluid reservoir, etc. As one example, any of the embodiments described herein can be used, for example, to transfer fluids to or from a patient via an indwelling peripheral intravenous line (PIV) (or other suitable access device or port). In such embodiments, the device can be coupled to an indwelling or placed PIV and can be manipulated to advance a catheter through the PIV to position a distal end portion of the catheter beyond a distal end of the PIV (e.g., within a target vein). In some embodiments, the devices can have a relatively compact form factor yet are arranged such that the compact form factor does not limit and/or reduce a length, "reach," or "throw" of the catheter, as described in further detail herein.

In some embodiments, an apparatus includes a housing, a catheter, and an actuator. The housing has a first port and a second port that is coupleable to an indwelling vascular access device. The catheter has a proximal end portion and a distal end portion, and it is at least partially disposed in the housing such that the first port of the housing receives the proximal end portion of the catheter. The actuator is partially disposed in the housing to selectively engage a portion of the catheter in the housing. The actuator is configured to be rotated an angular distance relative to the housing to move the distal end portion of the catheter a linear distance from a first position in which the distal end portion of the catheter is disposed in the housing, to a second position in which the catheter extends through the second port such that the distal end portion of the catheter is distal to the indwelling vascular access device when the second port is coupled to the indwelling vascular access device. The linear distance is greater than the angular distance.

In some embodiments, an apparatus includes a housing, a catheter, and an actuator. The housing has a first port and a second port that is coupleable to an indwelling vascular access device. The catheter has a proximal end portion and a distal end portion, and is at least partially disposed in the housing such that the first port of the housing receives the proximal end portion. The actuator defines and inner channel and is partially disposed in the housing such that the actuator and the housing collectively define an outer channel. The actuator is rotatable relative to the housing to move the catheter between a first position and a second position. The catheter in the first position extends within the housing from the first port, through the outer channel and the inner channel, and to the second port. The catheter in the second position extends within the housing from the first port, through the inner channel, and through the second port.

In some embodiments, an apparatus includes a catheter, a housing, and an actuator. The catheter has a proximal end portion and a distal end portion and defines a lumen extending through the proximal end portion and the distal end portion. The housing is configured to house at least a portion of the catheter. The housing has a first port configured to receive the proximal end portion of the catheter and a second port configured to couple the housing to an indwelling vascular access device such as, for example, an extended-dwell PIV and/or the like. The actuator is movably coupled to the housing. A portion of the actuator is disposed within the housing and is in contact with a portion of the catheter. The actuator is configured to be rotated an angular distance to move a distal end portion of the catheter a linear distance, where the linear distance is greater than the angular distance. The distal end portion of the catheter is disposed within the housing when in the first position and extends through the second port when in the second position such that the distal end portion of the catheter is distal to the indwelling vascular access device.

In some embodiments, an apparatus includes a catheter, a housing, and an actuator. The catheter has a proximal end portion and a distal end portion and defines a lumen extending through the proximal end portion and the distal end portion. The housing is configured to house a spool mechanism and at least a portion of the catheter. The housing has a first port configured to receive the proximal end portion of the catheter and a second port configured to couple the housing to an indwelling peripheral intravenous line. The actuator is coupled to the housing such that a portion of the actuator is disposed within the housing and in contact with the catheter. The actuator is configured to be moved relative to the housing to rotate the spool mechanism. The catheter is configured to be moved, as a result of the rotation, between a first position, in which the distal end portion of the catheter is disposed within the housing, and a second position, in which the distal end portion of the catheter extends through the second port such that the distal end portion of the catheter is distal to the second port.

In some embodiments, a fluid transfer device has a housing with a first port and a second port, a catheter that has a proximal end portion fixedly coupled to the first port, and an actuator that selectively engages the catheter. In some implementations, a method of using the fluid transfer device includes coupling the second port of the fluid transfer device to an indwelling vascular access device. The actuator is rotated an angular distance about a central axis defined by the housing. In response to rotating the actuator, a distal end portion of the catheter is advanced a linear distance from a first position to a second position. The distal end portion of the catheter is in the housing when the catheter is in the first position, and is advanced linearly in a direction orthogonal to the central axis through the second port and the indwelling vascular access device as the catheter is moved to the second position. The distal end portion of the catheter is distal to the indwelling vascular access device when the catheter is in the second position.

While at least some of the devices are described herein as being used with and/or coupled to a PIV in order to transfer fluid to or from a patient, it should be understood that such use is presented by way of example only and not limitation. For example, in other instances, the relatively compact arrangement of any of the devices described herein can allow the devices to be used with PIVs and/or other vascular access devices having an increased length relative to the length of a standard or "short" PIV (e.g., extended-dwell PIVs, midline PIVs, peripherally inserted central catheters (PICC), and/or the like), as described in further detail herein.

While described herein as being used, for example, to aspirate a volume of bodily fluid (e.g., blood) from a patient, it should be understood that the embodiments and/or devices are not limited thereto. For example, in some instances, the embodiments and/or devices can be used to aspirate bodily fluid including but not limited to, blood, cerebrospinal fluid, urine, bile, lymph, saliva, synovial fluid, serous fluid, pleural fluid, amniotic fluid, mucus, vitreous, air, and the like, or any combination thereof. In other instances, the embodiments and/or devices can be used to deliver one or more fluids from a fluid source to the patient. In still other instances, the embodiments and/or devices can be used in any suitable procedure or the like involving catheterization of a target region in the body. That is to say, the embodiments and/or devices are not limited to transferring fluids to or from a patient and can be used, for example, to provide access to a target region in the body of the patient for any suitable purpose. Moreover, it should be understood that references to "a patient" need not be limited to a human patient. For example, any of the devices described herein can be used in any suitable procedure performed on an animal (e.g., by a veterinarian and/or the like).

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "catheter" and "cannula" are used interchangeably to describe an element configured to define a passageway for accessing a portion of the body (e.g., of a human and/or animal). In some instances, the passageway defined by a catheter and/or cannula can be used for moving a bodily fluid or physical object (e.g., a stent, a punctate plug, a hyaluronic-acid-gel, etc.) from a first location to a second location. While cannulas can be configured to receive a trocar, a guide wire, or an introducer to deliver the cannula to a volume inside the body of a patient, the cannulas referred to herein need not include or receive a trocar, guide wire, or introducer.

As used herein, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the terms "about" and "approximately," when used in conjunction with values and/or ranges, generally refer to those values and/or ranges near to a recited value and/or range. In some instances, the terms "about" and "approximately" may mean within ±10% of the recited value. The terms "about" and "approximately" may be used interchangeably. By way of example, about 0.5 would include 0.45 and 0.55, about 10 would include 9 to 11, approximately 1000 would include 900 to 1100, etc. Similarly, the term "substantially" when used in conjunction with physical and/or geometric feature(s), structure(s), characteristic(s), relationship(s), etc. is intended to convey that the feature(s), structure(s), characteristic(s), relationship(s), etc. so defined is/are nominally the feature(s), structure(s), characteristic(s), relationship(s), etc. As one example, a first quantity that is described as being "substantially equal" to a second quantity is intended to convey that, although equality may be desirable, some variance can occur. Such variance can result from manufacturing tolerances, limitations, approximations, and/or other practical considerations.

The embodiments described herein and/or portions thereof can be formed or constructed of one or more biocompatible materials. In some embodiments, the biocompatible materials can be selected based on one or more properties of the constituent material such as, for example, stiffness, toughness, durometer, bioreactivity, etc. Examples of suitable biocompatible materials include metals, glasses, ceramics, or polymers. Examples of suitable metals include pharmaceutical grade stainless steel, gold, titanium, nickel, iron, platinum, tin, chromium, copper, and/or alloys thereof. A polymer material may be biodegradable or non-biodegradable. Examples of suitable biodegradable polymers include polylactides, polyglycolides, polylactide-co-glycolides, polyanhydrides, polyorthoesters, polyetheresters, polycaprolactones, polyesteramides, poly(butyric acid), poly(valeric acid), polyurethanes, biodegradable polyamides (nylons), and/or blends and copolymers thereof. Examples of non-biodegradable polymers include non-degradable polyamides (nylons), polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, and/or blends and copolymers thereof.

Figure 2:
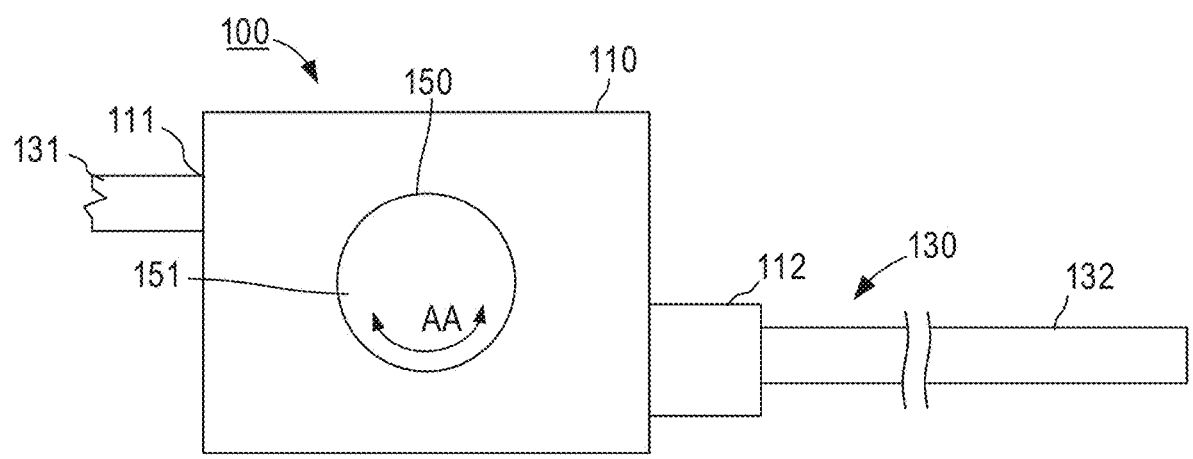

FIGS. 1 and 2 are schematic illustrations of a fluid transfer device 100 in a first configuration and second configuration, respectively, according to an embodiment. In some embodiments, the fluid transfer device 100 (also referred to herein as "device") can be configured to couple to and/or otherwise engage an access device and/or the like and can be manipulated to place a portion of a catheter in a desired position relative to the access device and/or within the body. For example, the device 100 can be coupled to an indwelling peripheral intravenous catheter (PIV) to transfer bodily fluid from and/or transfer fluid to a portion of a patient (e.g., aspirate a volume of blood or infuse a drug or substance), as described in further detail herein.

The device 100 can be any suitable shape, size, and/or configuration. As shown in FIG. 1, the device 100 includes at least a housing 110, a catheter 130 (or cannula), and an actuator 150. The housing 110 can be any suitable configuration. For example, in some embodiments, the housing 110 can be an elongate member having a substantially circular cross-sectional shape (e.g., cylindrical). In other embodiments, the housing 110 can have a square, rectangular, and/or any other polygonal cross-sectional shape. In other embodiments, the housing 110 can be a cube or the like having rounded or non-rounded edges, corners, etc. In still other embodiments, the housing 110 can have any suitable irregular shape, cross-section, and/or the like. In some embodiments, the shape of the housing 110 and/or one or more features and/or surface finishes of at least an outer surface of the housing 110 can be arranged to increase the ergonomics of the device 100, which in some instances, can allow a user to manipulate the device 100 with one hand (i.e., single-handed use). As described in further detail herein, the arrangement of the device 100 is such that the housing 110 has a relatively compact length or the like without limiting and/or reducing a length of the catheter 130. In some implementations, the housing 110 can have a length and/or size that is less than, for example, a length of the catheter 130 at least partially disposed therein.

The housing 110 has a first port 111 and a second port 112. The first port 111 (e.g., a proximal port) is configured to receive a proximal end portion 131 of the catheter 130 and the second port (e.g., a distal port) is configured to movably receive a distal end portion 132 of the catheter 130. The ports 111 and 112 can be any suitable configuration. For example, in some embodiments, the first port 111 can be a clamp, grommet, o-ring, compression member, Luer Lok™, and/or any other suitable coupler. In some implementations, the first port 111 can receive the proximal end portion 131 of the catheter 130 and can allow a portion of the catheter 130 to be disposed within the housing 110 while maintaining a fixed portion (e.g., the proximal end portion 131) of the catheter 130 outside of the housing 110, as described in further detail herein. In some embodiments, the second port 112 can be a lock mechanism and/or coupler configured to couple the housing 110 to a PIV (e.g., an indwelling or placed PIV) and/or any suitable adapter coupled to a PIV (e.g., an IV extension set or the like). For example, in some embodiments, the second port 112 can be a Luer Lok™, a "Clip-Lock-Snap" connection, and/or the like configured to physically and fluidically couple to, for example, the PIV. Moreover, the second port 112 is configured to movably receive the distal end portion 132 of the catheter 130 to allow the distal end portion 132 of the catheter 130 to be advanced through the second port 112 and the PIV (not shown in FIGS. 1 and 2) to be at least partially disposed within a vein of a patient (e.g., the vein in which the PIV is dwelling), as described in further detail herein.

While the second port 112 is described as being configured to couple to a PIV, it should be understood that the second port 112 can be configured to couple to any suitable connector, adapter, access device, and/or any other suitable device. Moreover, as described above, the PIV can be a standard or short PIV, an extended-dwell PIV, a midline PIV, a PICC line, and/or the like.

The catheter 130 includes the proximal end portion 131 and the distal end portion 132 and defines a lumen (not shown) that extends through the proximal end portion 131 and the distal end portion 132. While described as defining a lumen, in some embodiments, the catheter 130 can include and/or define multiple lumens, channels, flow paths, etc. Although not shown in FIGS. 1 and 2, the proximal end portion 131 of the catheter 130 can include and/or can be coupled to a coupler and/or lock configured to couple (e.g., physically and fluidically) the catheter 130 to any suitable device and/or reservoir (e.g., a syringe, fluid reservoir, sample reservoir, evacuated container, fluid source, etc.). The distal end portion 132 of the catheter 130 is configured to be inserted into a portion of a patient's body, as described in further detail herein.

At least a portion of the catheter 130 is movably disposed within the housing 110. In some embodiments, the catheter 130 can be moved (e.g., via movement of the actuator 150) between a first position and a second position to transition the device 100 between the first configuration and the second configuration, respectively. More specifically, the distal end portion 132 of the catheter 130 is disposed within the housing 110 when the catheter 130 is in the first position (FIG. 1) and at least a portion of the catheter 130 (e.g., the distal end portion 132) extends through the second port 112 and the PIV (not shown) to place a distal end of the catheter 130 in a distal position relative to the PIV when the catheter 130 is in the second position (FIG. 2), as described in further detail herein.

The catheter 130 can be formed from any suitable material or combination of materials such as those described above. In some embodiments, the catheter 130 can be formed from a material or combination of materials and/or can have a size, shape, diameter, thickness, etc. to result in any suitable stiffness, flexibility, hardness, and/or durometer. In some embodiments, at least a portion of the catheter 130 can be formed of a braided material or the like, which can change, modify, and/or alter a flexibility of the catheter 130 in response to a bending force or the like. In some embodiments, forming the catheter 130 of the braided material or the like can reduce a likelihood of kinking, pinching, bending, and/or otherwise deforming in an undesired manner. In addition, forming at least a portion of the catheter 130 of a braided material can result in a compression and/or deformation in response to a compression force exerted in a direction of a longitudinal centerline defined by the catheter 130 (e.g., an axial force or the like). In this manner, the catheter 130 can absorb a portion of force associated with, for example, hitting an obstruction or the like.

The catheter 130 can be any suitable shape, size, and/or configuration. In some embodiments, the catheter 130 can have a length, diameter, and/or configuration that is based at least in part on a one or more characteristics and/or aspects of the access device to which the device 100 is configured to be coupled. For example, in some embodiments, at least a portion of the catheter 130 can have an outer diameter (e.g., between 8-gauge and 33-gauge, and/or any other suitable size or range of sizes) that is substantially similar to or slightly smaller than an inner diameter defined by a portion of the second port 112 and/or an inner diameter defined by a portion of the access device to which the second port 112 is coupled (e.g., a PIV, extended-dwell PIV, midline, PICC line, etc.). In this manner, an inner surface of the second port 112 and/or PIV can guide the catheter 130, as it is moved therethrough, as described in further detail herein. In some embodiments, such an arrangement can limit and/or can substantially prevent bending, deforming, and/or kinking of a portion of the catheter 130 during use.

In some embodiments, the catheter 130 can have a length sufficient to place a distal surface of the catheter 130 in a desired position within and/or relative to the access device when the catheter 130 is in the second position. In some embodiments, the length of the catheter 130 can be sufficient to define a predetermined, desired, and/or at least a threshold distance between the distal surface of the catheter 130 and the distal surface of the PIV when the catheter 130 is in the second position. In some instances, placing the distal surface of the catheter 130 at the predetermined, desired, and/or at least the threshold distance from the distal surface of the PIV can, for example, place the distal surface of the catheter 130 in a desired position within a vein, as described in further detail herein. In some embodiments, the catheter 130 can include markings or indications that can be used to determine the distance between the distal surface of the catheter 130 and the distal surface of the PIV when the catheter 130 is in the second position. Moreover, the catheter 130 can have a length that is sufficient to place the distal surface of the catheter 130 in a desired position relative to the distal surface of an access device having a relatively long length when fully extended (e.g., in the second position) and thus, when the device 100 is coupled to an access device having a relative short length, the distal surface of the catheter 130 can be placed in the desired position relative to a distal surface of the shorter access device without being fully extended.

In some embodiments, for example, the predetermined, desired, and/or threshold (e.g., minimum) distance between the distal surface of the catheter 130 and the distal surface of the access device (e.g., PIV) can be between about 0.0 millimeters (mm) and about 50.0 mm (about 0.0 inches (in) to about 2 in). In other embodiments, the predetermined, desired, and/or threshold distance can be between about 15.0 mm and about 30.0 mm (about 0.59 in and about 1.18 in). In still other embodiments, the distal end portion 132 of the catheter 130 can be advanced, for example, through a hub of the access device while remaining proximal to the distal surface of the access device (e.g., the distal end portion 132 of the catheter 130 does not extend through the access device). For example, in some embodiments, the predetermined and/or desired distance between the distal surface of the catheter 130 and the distal surface of the access device can be when the distal surface of the catheter 130 is between about 80.0 mm and about 0.0 mm (about 3.15 in and about 0.0 in) proximal to the distal surface of the access device (e.g., −80.0 mm to about 0.0 mm).

In some embodiments, the length of the catheter 130 can be based at least in part on a desired and/or intended use. For example, in some embodiments, the device 100 can be configured for use in interventional cardiology wherein the catheter 130 can have a length of, for example, 320.0 centimeters (cm) (about 12.60 in) or more. In other embodiments, the device 100 can be configured for use in fluid transfer via a PIV (e.g., a standard or short PIV, an extended dwell PIV, a midline, etc.) and can have a length between about 1.77 cm and about 25.4 cm (about 0.5 inches (in) and about 10.0 in).

In some embodiments, the length of the catheter 130 can be greater than a length of the housing 110. Moreover, a length of a portion of the catheter 130 disposed in the housing 110 can be greater than the length of the housing 110 and/or at least a length of a line extending between the first port 111 and the second port 112 of the housing 110. For example, in some embodiments, the portion of the catheter 130 disposed in the housing 110 can form and/or can be arranged in a U-shaped configuration forming a U-bend or 180° turn in the housing. In other embodiments, the portion of the catheter 130 disposed in the housing can form and/or can be arranged in any suitable manner and/or with any suitable angle of turn from no turn (0°) to a complete turn (360°) or to more than a complete turn (e.g., can form any number of loops or any suitable portions thereof). In other embodiments, the portion of the catheter 130 disposed in the housing 110 can be arranged a spiral configuration, a coil configuration, and/or any other circuitous, tortuous, or substantially non-linear configuration.

Accordingly, the arrangement of the catheter 130 disposed in the housing 110 can result in an increased "reach" of the catheter 130 for a given length of the housing 110. In some implementations, such an arrangement can allow the device 100 to be used with access devices and/or the like having a relatively long length such as, for example, extended-dwell PIVs, midline PIVs, PICC lines, and/or the like. In other implementations, the arrangement of the catheter 130 disposed in the housing 110 can allow a length of the housing 110 to be reduced without a similar or corresponding reduction in the length or reach of the catheter 130. Moreover, the arrangement of the catheter 130 within the housing 110 can result in a shorter unsupported portion of the catheter 130 when compared to an unsupported portion of a catheter having a straight or linear configuration, which can reduce a likelihood of undesired bowing, kinking, bending, deflecting, and/or deforming, as the catheter 130 is advanced to the second position.

The actuator 150 of the device 100 can be any suitable shape, size, and/or configuration. The actuator 150 is coupled to the housing 110 and the catheter 130. More specifically, the actuator 150 can be a rotary actuator or mechanism that includes a first portion disposed outside of the housing 110 and a second portion disposed within the housing 110. In this manner, a user can engage the first portion to move the actuator 150 relative to the housing 110 by rotating the actuator 150, as indicated by the arrows AA in FIGS. 1 and 2. In some embodiments, the housing 110 can define a range of motion of the actuator 150. For example, in some embodiments, can include a structure, feature, component, and/or the like that can selectively engage a portion of the actuator 150 to limit, restrict, guide, and/or otherwise direct an amount or direction of movement of a portion of the actuator 150. That is to say, the actuator 150 can be rotated through a desired range of motion and/or through a desired angular displacement based at least in part on a size and/or arrangement of a portion of the actuator 150 and a size and/or arrangement of a portion of the actuator housing 110. As described in further detail herein, the actuator 150 can be actuated (e.g., rotated) to advance the catheter 130 between a first position (FIG. 1) and a second position (FIG. 2).

Although not show in FIGS. 1 and 2, the second portion of the actuator 150 is coupled to and/or in contact with the catheter 130. For example, in some embodiments, the second portion of the actuator 150 can be and/or can include a relatively rigid member, mechanism, sleeve, and/or the like that defines a lumen or channel configured to movably receive a portion of the catheter 130. In some embodiments, the lumen or channel of the second portion can have a U-shape configuration, a bent configuration, a spiral configuration, a coil configuration, a circuitous or tortuous configuration, and/or the like. In some embodiments, the second portion and/or the lumen or channel defined by the second portion can have any suitable radius of curvature and any suitable surface configured to engage, direct, and/or control at least a portion of the catheter 130.

In other embodiments, the second portion of the actuator 150 can be a wheel, disc, gear, sprocket, and/or the like configured to contact a portion of the catheter 130 and/or a member coupled to the catheter 130. In such embodiments, the arrangement of the second portion and the catheter 130 is such that an outer surface of the catheter 130 can contact the second portion of the actuator 150 such that a friction force resulting from the contact at least partially resists movement of the catheter 130 against the second portion of the actuator 150. In this manner, when the actuator 150 is rotated relative to the housing 110, the second portion of the actuator 150 advances the catheter 130 in a direction that is tangent (or substantially tangent) to a point (or area) of contact between the second portion of the actuator 150 and the catheter 130.

The arrangement of the device 100 can be such that rotational movement of the actuator 150 about a given axis in the housing 110 advances a portion of the catheter 130 engaged with the actuator 150 (e.g., the second portion of the actuator 150), which in turn, moves the catheter 130 between the first position and the second position. As described above, the proximal end portion 131 of the catheter 130 is coupled to and/or otherwise extends through the first port 111 while the distal end portion 132 of the catheter 130 is configured to be moved relative to the housing 110 (e.g., through the second port 112). Thus, as shown in FIG. 2, rotating the actuator 150 in a counterclockwise direction (e.g., the AA direction) advances a portion of the catheter 130 about the axis of the actuator 150 (e.g., about the second portion of the actuator 150, not shown). In response, the distal end portion 132 of the catheter 130 is moved from the first position (FIG. 1) to the second position (FIG. 2).

In some embodiments, the arrangement of the catheter 130 can be such that the proximal end portion 131 of the catheter 130 is fixedly coupled to and/or otherwise maintained in a fixed position relative to the first port 111. As such, rotating the actuator 150 through a rotational and/or angular displacement can advance, coil (or uncoil), spool (or unspool), and/or otherwise move the portion of the catheter 130 disposed within the housing 110. In other words, the proximal end position 131 can be maintained in a substantially fixed position relative to the housing 110 as the catheter 130 is moved between the first position and the second position. In other embodiments, the proximal end portion of the catheter 130 can be movably coupled to and/or movably received by the first port 111. As such, rotating the actuator through a rotational and/or angular displacement can advance, coil (or uncoil), spool (or unspool), and/or otherwise move all or substantially all of the catheter 130 relative to the housing 110 in response to actuation of the actuator 150. In this manner, whether the proximal end portion 131 of the catheter 130 is fixedly or movably coupled to the first port 111 of the housing 110, the arrangement of the device 100 can be such that the housing 110 has a relatively compact, limited, and/or reduced length while the catheter 130 has a length sufficient to extend a desired distance (e.g., at least partially into or through a standard or short PIV, an extended-dwell PIV, a midline PIV, a PICC line, and/or any other suitable access device).

FIGS. 3 and 4 illustrate a fluid transfer device 200, according to another embodiment. The fluid transfer device 200 (also referred to herein as "device") includes a housing 210, a catheter 230, and an actuator 250. As shown in FIGS. 3 and 4, the housing 210 is an elongate member, tube, housing, introducer, etc. In some embodiments, the housing 210 can be substantially straight and/or linear with a relatively small interior cross-sectional shape. As described above with reference to the housing 110, the housing 210 shown in FIGS. 3 and 4 includes a first port 211 (e.g., a proximal port) and a second port 212 (e.g., a distal port). The ports 211 and 212 can be any suitable coupling mechanism, lock, port, opening, cap, etc., and can be the same configuration or different configurations. That is to say, the first port 211 can be similar to the second port 212 or different from the second port 212. Moreover, the second port 212 is configured to be coupled to an access device such as, for example, a PIV, extended-dwell PIV, midline, PICC line, and/or the like.

The catheter 230 can be any suitable lumen-defining device. For example, in some embodiments, the catheter 230 can be similar to or substantially the same as the catheter 130 described above with reference to FIGS. 1 and 2. Accordingly, portions and/or aspects of the catheter 230 may not be described in further detail herein.

As shown in FIGS. 3 and 4, the catheter 230 is configured to be at least partially and/or temporarily disposed in the housing 210. More particularly, the catheter 230 includes a proximal end portion 231 that is coupled to, received by, and/or otherwise positioned at or near the first port 211 and a distal end portion 232 that is coupled to, received by, and/or otherwise positioned at or near the second port 212. In the embodiment shown in FIGS. 3 and 4, the proximal end portion 231 of the catheter 230 is movably coupled to and/or otherwise received by the first port 211. For example, the first port 211 can be configured to allow at least the proximal end portion 231 of the catheter 230 to move therethrough. In some embodiments, the proximal end portion 231 of the catheter 230 can be coupled to a secondary catheter or the like configured to place the catheter 230 in fluid communication with a fluid source, fluid reservoir, and/or any other suitable device. In other embodiments, the proximal end portion 231 of the catheter 231 can movably extend, at least in part, through the first port 211. As shown in FIGS. 3 and 4, the distal end portion 232 of the catheter 230 is configured to be movably coupled to and/or otherwise received by the second port 212 of the housing 210. As such, at least a portion of the catheter 230 disposed between the proximal end portion 231 and the distal end portion 232 is disposed within the housing 210.

The actuator 250 can be any suitable member, mechanism, device etc. For example, in some embodiments, the actuator 250 can be substantially similar in at least form and/or function to the actuator 150 described above with reference to FIGS. 1 and 2. As shown in FIGS. 3 and 4, the actuator 250 includes a first portion 251 and a second portion 252. The actuator 250 can be coupled to the housing 210 at or near the second port 212 of the housing 210 (e.g., at or near a distal end portion of the housing 210). In other embodiments, the actuator 250 can be coupled to the housing 210 at any suitable position along a length of the housing 210. The actuator 250 can be coupled to the housing 210 in any suitable manner that allows the actuator 250 to be rotated relative to the housing 210. Moreover, the actuator 250 can be coupled to the housing 210 such that the second portion 252 is at least partially disposed within the housing 210 and in contact with and/or otherwise allowed to engage the catheter 230.

As described above with reference to the actuator 150, the actuator 250 is configured such that rotational movement of the actuator 250, results in the second portion 252 of the actuator 250 engaging the catheter 230, thereby moving the catheter 230 in a linear direction between a first position (e.g., a proximal position as shown in FIG. 3) and a second position (e.g., a distal position as shown in FIG. 4). More specifically, in use, the device 200 can be in a first configuration and/or state in which at least the distal end portion of the catheter is 230 is disposed within the housing 210 (FIG. 3) and a user can manipulate the device 200 by engaging the first portion 251 of the actuator 250 to place the device 200 in a second configuration and/or state. For example, the user can exert a force on the first portion 251 of the actuator 250 to rotate the actuator in, for example, a clockwise direction, as indicated by the arrow BB in FIG. 4. As such, the second portion 252 of the actuator 250 rotates relative to the housing 210 and engages the catheter 230 to move the catheter 230 in the distal direction, as indicated by the arrow CC in FIG. 4. Thus, when the second port 212 of the housing 210 is coupled to an access device or the like (not shown in FIGS. 3 and 4), the catheter 230 can be advanced to a desired position relative to the access device, as described above with reference to the device 100.

In some embodiments, a ratio of angular displacement of the actuator 250 relative to linear displacement of the catheter 230 can be tuned and/or selected such that the catheter 230 is moved with a desired set of characteristics. For example, the device 200 can be preset such that a known number of turns or portions of a turn (e.g., ½ turn, 1 turn, 10 turns, etc.) can result in a known amount of advancement of the distal end portion 232 of the catheter 230. In some embodiments, the device 200 can be configured with a mechanical advantage, gearing, etc. that can result in a "length multiplying" and/or "displacement multiplying" effect such that a relatively small amount of rotation of the actuator 250 results in a relatively large amount of translation of the distal end portion 232 of the catheter 230. When accessing a vein or the like via the access device coupled to the second port 212, the linear displacement of at least the distal end portion 232 of the catheter 230 can be sufficient to place a distal surface of the catheter 230 in a desired position relative to a distal surface of the access device regardless of the type and/or length of the access device. For example, in some instances, it may be desirable to position the distal surface of the catheter 230 distal to the distal surface of the access device. In such instances, the arrangement of the device 200 can be such that the housing 210 has a compact, limited, and/or reduced length while the catheter 230 has a length sufficient to extend beyond a distal end of the access device (e.g., a PIV or the like).

In some embodiments, the arrangement of the actuator 250 and catheter 230 can also be tuned and/or selected based at least in part on an amount of force exerted on the actuator 250 to rotate the actuator 250 and/or an amount of force associated with advancing the catheter 230. For example, in some embodiments, the arrangement of the actuator 250 and catheter 230 can be such that the distal end portion 232 of the catheter 230 is advanced in response to a relatively small amount of force being applied on the actuator 250 (e.g., via a mechanical advantage, gearing, etc.). In some embodiments, an amount of a friction force between the second portion 252 of the actuator 250 and the catheter 230 can be increased or decreased to allow for a desired amount of slipping between the second portion 252 and the catheter 230 in response to the catheter hitting an obstruction or the like. In some instances, reducing an amount of force associated with advancement of the catheter 230 can reduce and/or limit damage to the catheter 230 and/or other structure (e.g., a vein wall or portion of the access device) that may otherwise result from the distal surface of the catheter 230 hitting an obstruction or the like.

Figure 5:
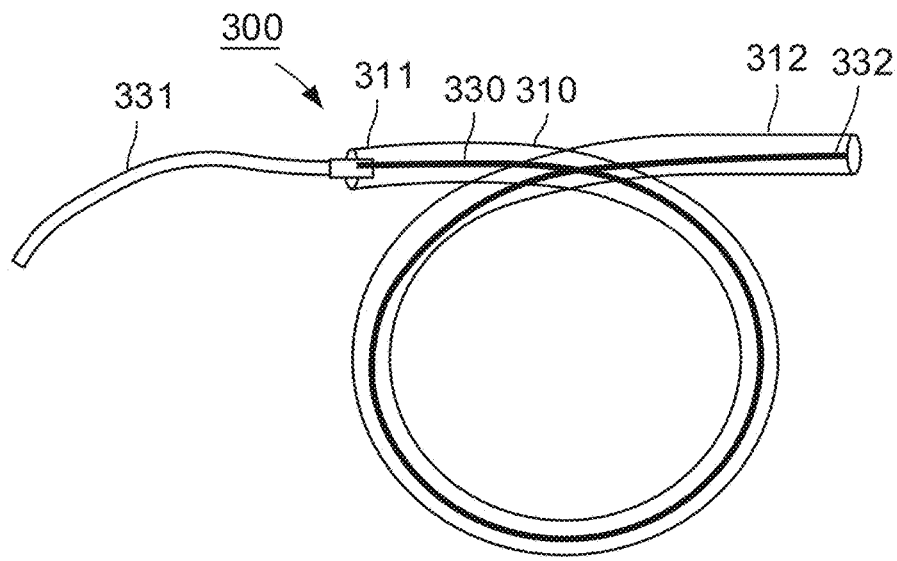
FIGS. 5 and 6 are schematic illustrations of a fluid transfer device in a first configuration and a second configuration, respectively, according to an embodiment.
Figure 6:
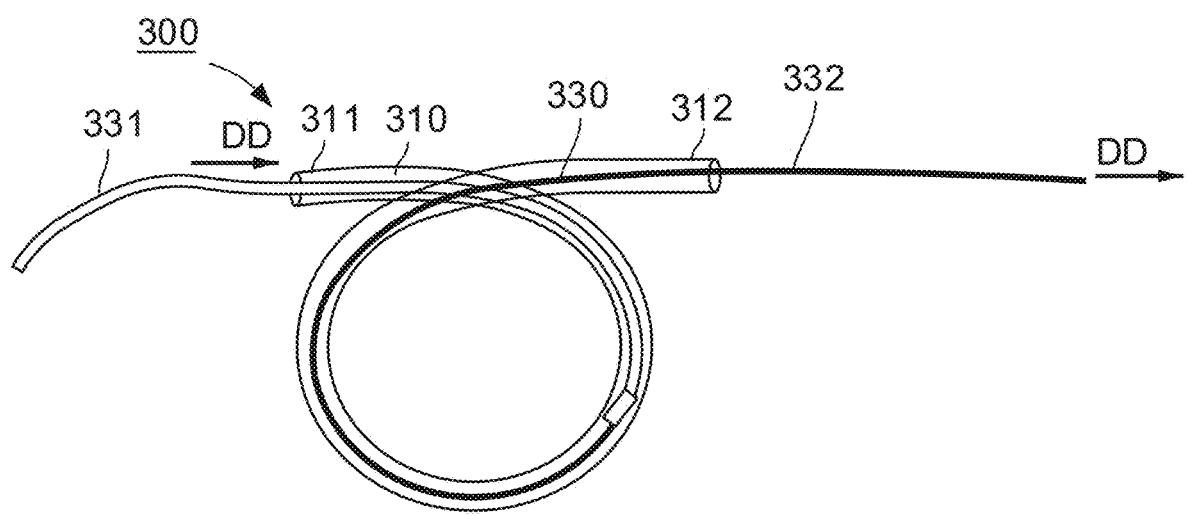

FIGS. 5 and 6 illustrate a fluid transfer device 300 according to another embodiment. The fluid transfer device 300 (also referred to herein as "device") can be substantially similar to the devices 100 and/or 200 in at least some aspects of its structure and/or function. The device 300 includes a housing 310 and a catheter 330. The housing 310 includes a first port 311 configured to receive a proximal end portion 331 of the catheter 330 and a second port 312 configured to receive a distal end portion 332 of the catheter 330, as described above with reference to the devices 100 and/or 200. As shown in FIGS. 5 and 6, the housing 310 can be an elongate member, tube, introducer, sheath, and/or the like that includes and/or forms a loop or a complete 360° turn between the first port 311 and the second port 312. For example, in some embodiments, the housing 310 can be a relatively rigid member (e.g., formed from a relatively hard plastic and/or the like) that is formed or molded into the looped shape or configuration. In other embodiments, the housing 310 can be formed from a relatively flexible material or the like that can allow the housing 310 to be bent, formed, curved, and/or otherwise reconfigured. In such embodiments, a user can manipulate the device 300 to place the housing 310 in any suitable shape and/or configuration. In some implementations, the housing 310 can be formed and/or placed into a shape or configuration that reduces, for example, an overall length and/or size of the device 300.

As described above with reference to the devices 100 and/or 200, the catheter 330 of the device 300 is configured to be at least partially disposed in the housing 300 and can be transitioned and/or moved between at least a first position (e.g., a proximal position) and a second position (e.g., a distal position). As shown, the catheter 330 includes a proximal end portion 331 that is coupled to, received by, and/or otherwise positioned at or near the first port 311 and a distal end portion 332 that is coupled to, received by, and/or otherwise positioned at or near the second port 312. In the embodiment shown in FIGS. 5 and 6, the proximal end portion 331 of the catheter 330 is movably coupled to and/or otherwise received by the first port 311, as described above with reference to the catheter 330. The distal end portion 332 of the catheter 330 is configured to be movably coupled to and/or otherwise received by the second port 312 of the housing 310. As such, at least a portion of the catheter 330 disposed between the proximal end portion 331 and the distal end portion 332 is disposed within the housing 310. In some embodiments, the turned or looped configuration of the housing 310 can be such that a length of the catheter 330 is longer than a length or distance between the first port 311 and the second port 312. Accordingly, the catheter 330 can have any desirable length or "reach" without substantially increasing an overall length of the device 300. While the housing 310 is shown as forming a single loop, circle, coil, turn, etc., it should be understood that a housing can include any number of loops or turns, thereby allowing for any suitable catheter length.

In the embodiment shown in FIGS. 5 and 6, a user can engage, for example, the proximal end portion 331 of the catheter 330 to move or transition the catheter 330 between the first position and the second position. For example, the device 300 can be in a first configuration and/or state in which the catheter 330 is in the first position (FIG. 5) and the user can exert a force on the proximal end portion 331 of the catheter 330 to move the catheter 330 in a distal direction toward the second position, as indicated by the arrows DD in FIG. 6. Similarly, the user can engage a portion of the catheter 330 to move the catheter 330 from the second position to or toward the first position (e.g., after use).

While the device 300 is shown and described above as being actuated in response to a force exerted on a portion of the catheter 330, in other embodiments, a device having a similar shape and/or configuration can include any suitable actuator configured move and/or transition the catheter 330. For example, in some embodiments, a device can include a slider or the like that can be slid and/or otherwise moved to move a catheter between a first position and a second position. In other embodiments, a device can include an actuator that is similar to the actuator 250 described above with reference to FIGS. 3 and 4.

For example, FIGS. 7 and 8 illustrate of a fluid transfer device 400 in a first configuration and second configuration, respectively, according to another embodiment. The fluid transfer device 400 (also referred to herein as "device") can be any suitable shape, size, and/or configuration. For example, at least a portion of the device 400 can be similar to and/or substantially the same as one or more portions (and/or combination of portions) of the devices 100, 200, and/or 300 described above. For example, as described in further detail herein, the device 400 can be a combination of certain portions and/or aspects of the devices 200 and 300. Thus, portions of the device 400 may not be described in further detail herein.

The device 400 includes at least a housing 410, a catheter 430, and an actuator 450. The housing 410 can be any suitable configuration. For example, in some embodiments, the housing 410 can be an elongate member having a substantially circular cross-sectional shape. The housing 410 includes a first port 411 configured to receive a proximal end portion 431 of the catheter 430 and a second port 412 configured to receive a distal end portion 432 of the catheter 430, as described above with reference to the devices 100, 200, and/or 300. In some embodiments, the housing 410 can be similar to and/or substantially the same as the housing 310 described above. For example, as shown in FIGS. 7 and 8, the housing 410 can be formed, molded, and/or otherwise placed into a bent, curved, looped, coiled, and/or spiraled shape or configuration. Thus, the housing 410 and/or aspects thereof are not described in further detail herein.

The catheter 430 of the device 400 can be any suitable shape, size, and/or configuration. For example, in some embodiments, the catheter 430 can be substantially similar to any of the catheters 130, 230, and/or 330 described above. For example, as described above with reference to the catheter 130, the catheter 430 can be formed from a material or combination of materials and can have a size, shape, diameter, thickness, and/or durometer configured to allow at least a portion of the catheter 430 to be moved from a first position to a second position (e.g., related to the housing 410) without undesirable bending, deforming, kinking, etc. Moreover, in some embodiments, the size, shape, diameter, length, and/or configuration of the catheter 430 may be based, at least in part, on one or more characteristics and/or aspects of an access device to which the device 400 is configured to be coupled, as described in detail above with reference to the catheter 130. Accordingly, such similar portions and/or aspects of the catheter 430 are not described in further detail herein.

At least a portion of the catheter 430 is movably disposed within the housing 410. In some embodiments, the catheter 430 can be moved between a first position, in which the distal end portion 432 of the catheter 430 is disposed within the housing 410 (FIG. 7), and a second position, in which at least a portion of the catheter 430 extends through the second port 412 and at least a portion of an access device (not shown) to which the second port 412 is coupled. In some embodiments, the catheter 430 can have a length sufficient to place a distal surface of the catheter 430 in a desired position relative to a distal surface of the PIV when the catheter 430 is in the second position. In some embodiments, the arrangement of the housing 410 and the catheter 430 can be substantially similar to the arrangement of the housing 310 and the catheter 330 described above with reference to FIGS. 5 and 6.

The device 400 can differ from the device 300, however, with the inclusion of the actuator 450, which can be used to move or transition the catheter 430 between the first position and the second position. The actuator 450 can be any suitable member, mechanism, device etc. For example, as shown in FIGS. 7 and 8, the actuator 450 includes a first portion 451 and a second portion 452. The actuator 450 can be coupled to the housing 410 at or near the second port 412 of the housing 410 (e.g., at or near a distal end portion of the housing 410). In other embodiments, the actuator 450 can be coupled to the housing 410 at any suitable position along a length of the housing 410. The actuator 450 can be coupled to the housing 410 in any suitable manner that allows the actuator 450 to be rotated relative to the housing 410. Moreover, the actuator 450 can be coupled to the housing 410 such that the second portion 452 is at least partially disposed within the housing 410 and in contact with and/or otherwise allowed to engage the catheter 430. In this manner, the actuator 450 can be substantially similar in at least form and/or function to the actuator 250 described above with reference to FIGS. 3 and 4.

In use, the device 400 can be in a first configuration and/or state in which at least the distal end portion of the catheter is 430 is disposed within the housing 410 (FIG. 7) and a user can manipulate the device 400 by engaging the first portion 451 of the actuator 450 to place the device 400 in a second configuration and/or state (FIG. 8). For example, the user can exert a force on the first portion 451 of the actuator 450 to rotate the actuator in, for example, a clockwise direction, as indicated by the arrow EE in FIG. 8. As such, the second portion 452 of the actuator 450 rotates relative to the housing 410 and engages the catheter 430 to move the catheter 430 in the distal direction, as indicated by the arrow FF in FIG. 8. Thus, when the second port 412 of the housing 410 is coupled to an access device or the like (not shown), the catheter 430 can be advanced to a desired position relative to the access device, as described in detail above with reference to the device 100.

Figure 9:
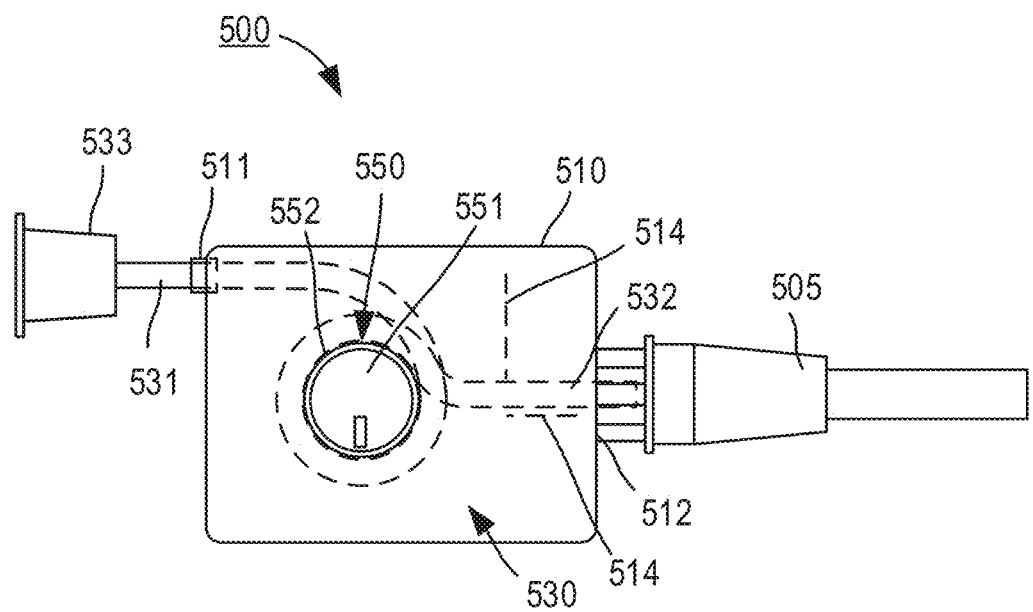
FIGS. 9 and 10 are schematic illustrations of a fluid transfer device in a first configuration and a second configuration, respectively, according to an embodiment.
Figure 10:
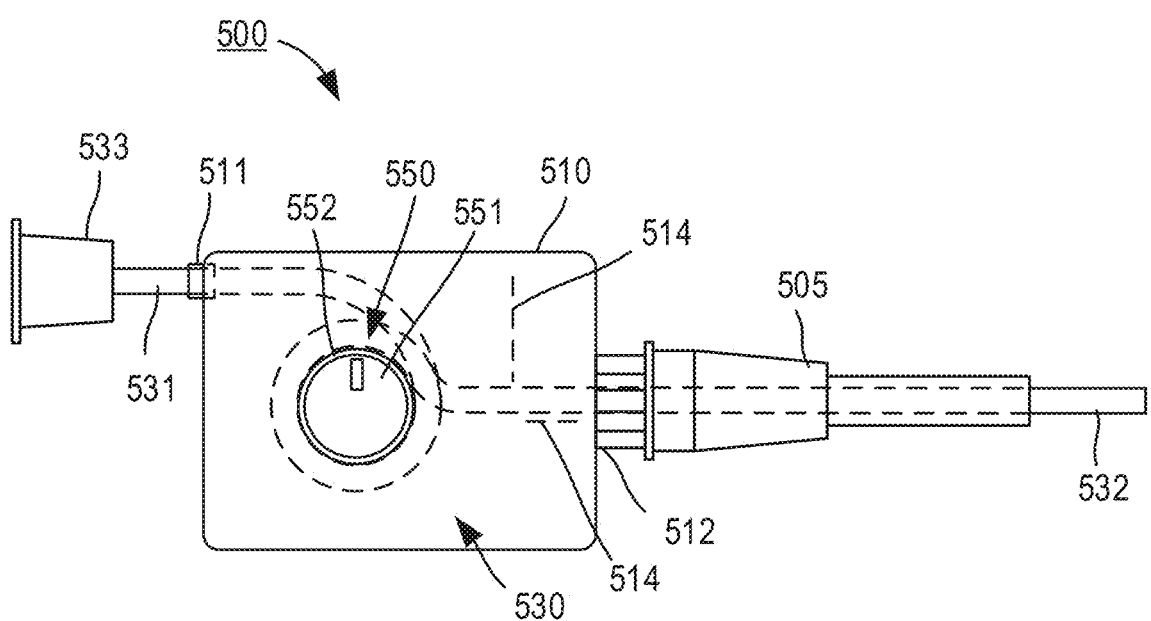

FIGS. 9 and 10 are schematic illustrations of a fluid transfer device 500 in a first configuration and second configuration, respectively, according to another embodiment. The fluid transfer device 500 (also referred to herein as "device") can be any suitable shape, size, and/or configuration. For example, at least a portion of the device 500 can be similar to and/or substantially the same as one or more portions (and/or combination of portions) of the devices 100, 200, 300, and/or 400 described above. Thus, portions of the device 500 may not be described in further detail herein.

The device 500 includes at least a housing 510, a catheter 530, and an actuator 550. The housing 510 can be any suitable configuration. In some embodiments, the shape of the housing 510 and/or one or more features and/or surface finishes of at least an outer surface of the housing 510 can be arranged to increase the ergonomics of the device 500, which in some instances, can allow a user to manipulate the device 500 with one hand (i.e., single-handed use). In some embodiments, portions and/or aspects of the housing 510 can be substantially similar to portions and/or aspects of the housings 110, 210, 310, and/or 410. Thus, such portions and/or aspects of the housing 510 may not be described in further detail herein.

The housing 510 has a first port 511 and a second port 512. The ports 511 and 512 can be any suitable configuration such as those described above with reference to the first port 111 and the second port 112, respectively. In the embodiment shown in FIGS. 9 and 10, the first port 511 extends, for example, from a proximal end or side of the housing 510 and the second port 512 extends, for example, from a distal end or side of the housing 510 (e.g., opposite the proximal end or side). The first port 511 is configured to fixedly or movably receive and/or couple to a proximal end portion 531 of the catheter 530. The second port 512 is configured to movably receive a distal end portion 532 of the catheter 530. Moreover, the second port 512 can be a lock mechanism and/or coupler configured to couple the device 500 to an access device or the like such as, for example, a PIV 505 (e.g., an indwelling PIV), as described above.

The catheter 530 of the device 500 can be any suitable shape, size, and/or configuration. For example, in some embodiments, the catheter 530 can be substantially similar in at least form and/or function to any of the catheters 130, 230, 330, and/or 430 described above. Thus, such similar portions and/or aspects of the catheter 530 may not described in further detail herein. For example, as described above with reference to the catheter 130, in the embodiment shown in FIGS. 9 and 10, the catheter 530 can be formed from any suitable material such as those described herein. Similarly, the catheter 530 can have any suitable diameter configured to allow at least a portion of the catheter 530 to be moved through the second port 512 without undesirable bending, deforming, kinking, etc., and can have any suitable length that can be at least partially based on one or more characteristics of the access device (e.g., the PIV 505) to which the device 500 is coupled, as described above with reference to the catheter 130.

Although not shown in FIGS. 9 and 10, the catheter 530 defines a lumen that extends through the proximal end portion 531 and the distal end portion 532. The proximal end portion 531 of the catheter 530 includes and/or is coupled to a coupler 533 (e.g., a Luer Lok™ or the like) configured to physically and fluidically couple the catheter 530 to any suitable device and/or reservoir (e.g., a syringe, fluid reservoir, sample reservoir, evacuated container, fluid source, etc.). The distal end portion 532 of the catheter 530 is configured to be inserted into and/or through at least a portion of the indwelling PIV 505 and, in some instances, into a portion of a patient's body, as described in further detail herein.

At least a portion of the catheter 530 is movably disposed within the housing 510. In some embodiments, the catheter 530 or a portion thereof can be moved (e.g., via rotational movement of the actuator 550) between a first position, in which the distal end portion 532 of the catheter 530 is disposed within the housing 510 (FIG. 9) and/or the second port 512, and a second position, in which at least a portion of the catheter 530 extends through the second port 512 and at least a portion of the PIV 505 (FIG. 10). In some embodiments, the catheter 530 can have a length sufficient to place a distal surface of the catheter 530 in a distal position relative to a distal surface of the PIV 505 when the catheter 530 is in the second position. In other words, the length of the catheter 530 can be sufficient to define a predetermined, desired, and/or threshold distance between the distal surface of the catheter 530 and the distal surface of the PIV 505 when the catheter 530 is in the second position. In some instances, placing the distal surface of the catheter 530 at the predetermined, desired, and/or threshold distance from the distal surface of the PIV 505 can, for example, place the distal surface of the catheter 530 in a desired position within a vein, as described in detail above with reference to the catheter 130.

In some embodiments, the length of the catheter 530 can be greater than a length of the housing 510 and/or at least a length of a line or axis defined between the first port 511 and the second port 512 of the housing 510. In some embodiments, the length of the catheter 530 can be many times greater than a length of the housing 510. For example, as described above with reference to the catheter 130, the catheter 530 can be disposed in the housing 510 in a wound or coiled arrangement including one or more complete coils (e.g., 360° turns) of the catheter 530 around at least a portion of the actuator 550 disposed within the housing 510. Although not shown in FIGS. 9 and 10, in some embodiments, one or more portions, sections, ends, etc. of the catheter 530 can be coupled to a portion of the actuator 550, which can allow at least a portion of the catheter 530 to be wound, spooled, coiled, etc. around the portion of the actuator 550, as described in further detail herein. In some embodiments, the housing 510 can include, form, and/or define a circular portion around a shaft associated with the actuator 550 within which at least a portion of the catheter 530 can be wound or coiled around the shaft in the circular portion to form one or more 360° turns (e.g., one complete turn, at least one complete turn and any suitable fraction of a complete turn, or multiple complete turns).

The portion of the catheter 530 disposed in the housing 510 can be of any suitable length. For example, in some embodiments, the length of the catheter 530 can be several times the length of the housing 510 without increasing a length of the housing 510, as described above with reference to the device 100 shown in FIGS. 1 and 2. Moreover, in some embodiments, the wound or coiled configuration of the catheter 530 can result in the catheter 530 being in a taut or supported configuration, which can reduce a portion of the catheter 530 that is unsupported within the housing 510. Such an arrangement can, for example, reduce a likelihood of undesired kinking, bending, bowing, deflecting, deforming, etc. of a portion of the catheter 530 as the catheter 530 is moved between the first position and the second position. In other words, reducing an unsupported length of the catheter 530 can result in the catheter 530 being more "pushable" (e.g., able to be advanced without undesired reconfiguration) from the first position to the second position. Moreover, in some embodiments, the housing 510 can include one or more internal structures 514 such as one or more walls, partitions, protrusions, ridges, ribs, channels, rollers, etc. configured to support and/or guide the catheter 530, as shown in FIGS. 9 and 10. While the internal structure 514 is particularly shown in FIGS. 9 and 10, a housing and/or any other portion of a device can include support structures that can act as a fence, post, rib, bumper, etc. configured to support the catheter as it is "pushed" and/or otherwise moved (e.g., advanced, retracted, etc.). In some embodiments, the support structures can be arranged in a direction of an axial force exerted along the catheter. In some embodiments, the support structures can be, for example, tangential to an exerted force and/or a movement or rotation of the catheter (or portion(s) thereof).

The actuator 550 of the device 500 can be any suitable shape, size, and/or configuration. As shown in FIGS. 9 and 10, the actuator 550 is movably coupled to the housing 510. The actuator 550 includes a first portion 551 (e.g., an engagement portion) disposed outside of the housing 510 and a second portion 552 (e.g., a shaft portion) disposed within the housing 510 and configured to engage and/or otherwise contact a portion of the catheter 530. The first portion 551 of the actuator 550 can be arranged as a rotary switch, rotary button, tab, knob, dial, etc. The second portion 552 of the actuator 550 can be, for example, a relatively rigid sleeve, tube, rod, shaft, drum, spool, and/or the like. The second portion 552 can be substantially cylindrical and/or can have a circular cross-sectional shape and can have any suitable radius of curvature. In some embodiments, the second portion 552 of the actuator 550 can include and/or can define a channel, conduit, and/or the like within or along which a portion of the catheter 530 can be wound.

In some embodiments, the catheter 530 is wound around the second portion 552 (e.g., the shaft portion) in or along a path formed or defined, at least in part, by the second portion 552 of the actuator 550. In some embodiments, a portion of the catheter 530 is disposed in a conduit and/or lumen that is operatively coupled to the second portion 552 of the actuator 550 such that a rotational movement of the actuator 550 results in a rotational movement of at least a portion of the catheter 530 that is wound or coiled around the second portion 552. Such an arrangement, in turn, results in a spooling (or unspooling), coiling (or uncoiling), winding (or unwinding), etc. of at least a portion of the catheter 530, thereby moving and/or transitioning the catheter 530 between the first position (FIG. 9) and the second position (FIG. 10). In some embodiments, the catheter 530 can have two sections (or the device can include two catheters), which can allow the catheter 530 to be coupled to the second portion 552 of the actuator 550. For example, in some embodiments, the proximal end portion 531 of the catheter 530 can be a first section or first catheter that is fixedly coupled to the first port 511 of the housing 510 and coupled to a port or the like (not shown) of the actuator 550. A medial portion of the catheter 530 (or an end portion of a second catheter) similarly can be coupled to a port of the actuator 550 and in fluid communication with the proximal end portion 531 of the catheter 530. In such embodiments, coupling the medial portion of the catheter 530 to the actuator 550 can allow a section of the catheter 530 to be spooled or coiled around the second portion 552 of the actuator 550. Moreover, distal end portion 532 of the catheter 530 can extend from the second portion 552 of the actuator 550 to the second port 512, as shown in FIG. 9.

In some implementations, the distal end portion 532 of the catheter 530 can be at least partially disposed within and/or otherwise aligned with the second port 512 such that the rotation of the actuator 550 and the portion of the catheter 530 spooled and/or coiled about the second portion 552 of the actuator 550 results in a substantially linear movement of the distal end portion 532 of the catheter 530 relative to, within, and/or through the second port 512. Moreover, the one or more internal structures 514 of the housing 510 can support and/or guide at least a portion of the catheter 530 as the catheter 530 is moved and/or transitioned between the first position and the second position. In some embodiments, the radius of curvature of the second portion 552 can be such that the portion of the catheter 530 can move and/or transition between the first position and the second position without kinking, binding, binding, and/or otherwise undesirably deforming.

Although not shown in FIGS. 9 and 10, in some embodiments, an outer surface of the housing 510 and/or a surface defining at least a portion thereof can include and/or can form a set of ribs, ridges, bumps, notches, etc. configured to be in contact with a surface of the actuator 550. In such embodiments, the surface of the actuator 550 can move along the ribs or the like as the actuator 550 is rotated relative to the housing 510. As such, the movement can result in a haptic and/or audible output that can provide a user with an indicator or the like associated with a relative amount of rotation of the actuator 550 and/or a corresponding relative movement (e.g., linear movement) of the catheter 530. In some embodiments, the arrangement of the ribs or the like and the actuator 550 can act as a friction system or the like that can, for example, retain the actuator 550 (and thus, the catheter 530) in a substantially fixed rotational and/or angular position in the absence of an external force being applied on the actuator 550 (e.g., a torque or turning force applied by the user).

The arrangement of the device 500 is such that moving the actuator 550 (e.g., the first portion 551 and the second portion 552, collectively) about an axis defined in the housing 510 and/or otherwise relative to the housing 510 advances a portion of the catheter 530 along and/or through a path defined within the housing 510. For example, when the device 500 is in a first configuration or state (FIG. 9), rotation of the actuator 550 in a clockwise direction moves the catheter 530 from the first position and the second position (FIG. 10). In some implementations, the proximal end portion 531 of the catheter 530 coupled between the first port 511 and the second portion 552 of the actuator 550 and the medial portion (and/or any other suitable portion) of the catheter 550 also being coupled to the second portion 552 of the actuator 550 and at least partially spooled or coiled thereabout, rotating the actuator 550, for example, advances a portion of the catheter 530 along and/or through the path (not shown) defined within the housing 510, which in turn, moves the distal end portion 532 of the catheter 530 relative to the second port 512 and/or the access device coupled thereto (e.g., the PIV 505).

As described above, the arrangement of the device 500 is such that moving the actuator 550 an angular amount or distance (e.g., an amount of rotation) results in the distal end portion 532 of the catheter 530 being moved a linear amount or distance. In other words, linear displacement (e.g., translation) of the distal end portion 532 of the catheter 530 is achieved with the angular displacement (e.g., rotation) of the actuator 550. In some embodiments, the ratio of angular displacement to linear displacement can be predetermined. For example, the device 500 can be preset such that a known number of turns or portions of a turn (e.g., ½ turn, 1 turn, 10 turns, etc.) can result in a known amount of advancement of the distal end portion 532 of the catheter 530. In some embodiments, the device 500 can be configured with a mechanical advantage, gearing, etc. that can result in a "length multiplying" and/or "displacement multiplying" effect such that a relatively small amount of rotation of the actuator 550 results in a relatively large amount of translation of the distal end portion 532 of the catheter 530. When accessing a vein or the like via the PIV 505, the linear displacement of at least the distal end portion 532 of the catheter 530 can be sufficient to place a distal surface of the catheter 530 in a desired position relative to a distal surface of the PIV 505 regardless of the type and/or length of the PIV 505. For example, in some instances, it may be desirable to position the distal surface of the catheter 530 distal to the distal surface of the PIV 505. In such instances, the arrangement of the device 500 can be such that the housing 510 has a compact, limited, and/or reduced length while the catheter 530 has a length sufficient to extend beyond a distal end of the PIV 505.

While the arrangement of the actuator 550 and catheter 530 is described above as being used, for example, to multiply an amount displacement of the distal end portion for a given angular displacement of the actuator, in some embodiments, the arrangement can also reduce an amount of force associated with advancing the distal end portion 532 of the catheter 530. For example, in some embodiments, the mechanical advantage, gearing, etc. can be such that the distal end portion 532 of the catheter 530 is advanced in response to a reduced amount of force being applied on the actuator 550. In some instances, reducing an amount of force associated with advancement of the catheter 530 can reduce and/or limit damage to the catheter 530 and/or other structure (e.g., a vein wall or portion of the PIV 505) that may otherwise result from the distal surface of the catheter 530 hitting an obstruction or the like.

Figure 11:
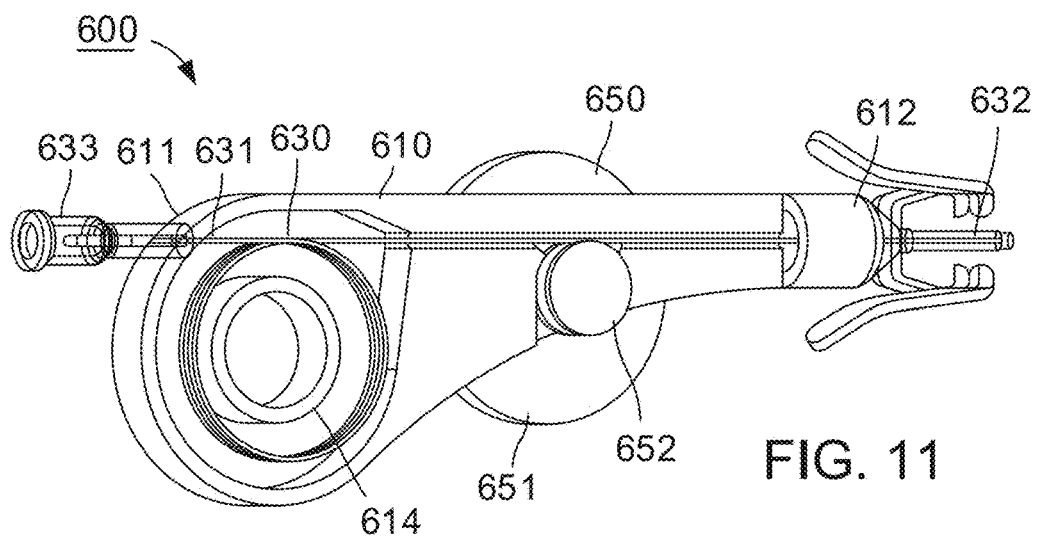
FIG. 11 is a partial cross-sectional perspective view of a fluid transfer device according to an embodiment.
Figure 12:
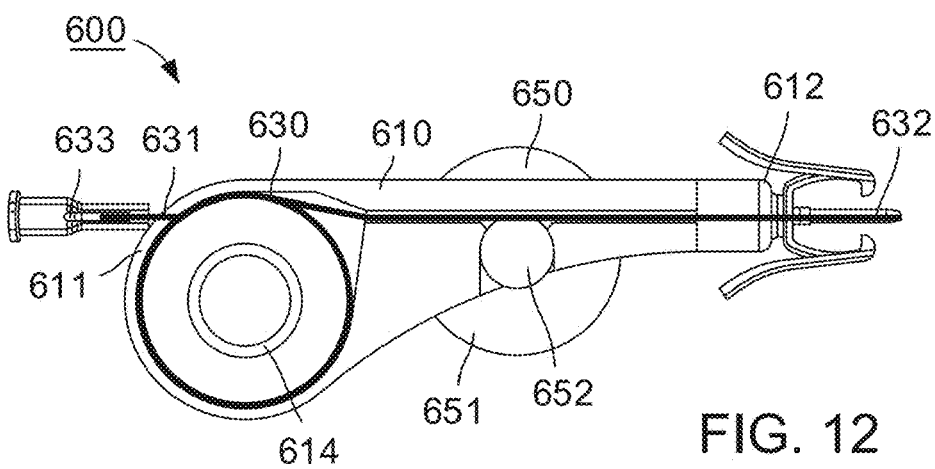
FIGS. 12 and 13 are partial cross-sectional side views of the fluid transfer device of FIG. 11 in a first configuration and a second configuration, respectively.
Figure 13:
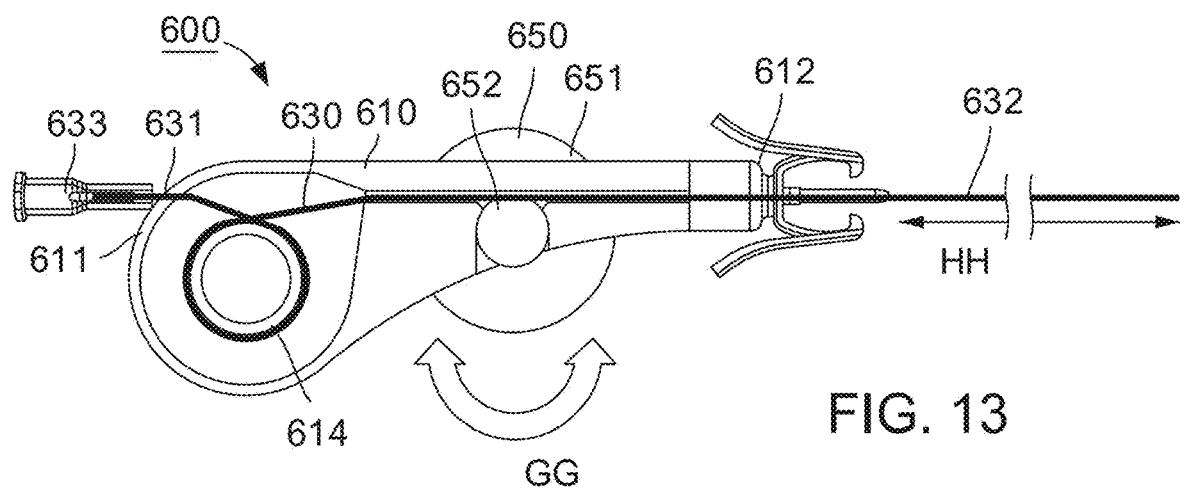

While the housing 510 is shown in FIGS. 9 and 10 as including the one or more internal structures 514 configured to support, guide, and/or direct at least a portion of the catheter 530 as the catheter 530 is moved between the first position and the second position, in other embodiments, a device can include a housing having any suitable internal structure that can support, guide, and/or direct at least a portion of a catheter. For example, FIGS. 11-13 illustrate a fluid transfer device 600 according to another embodiment. The fluid transfer device 600 (also referred to herein as "device") can be any suitable shape, size, and/or configuration. For example, at least a portion of the device 600 can be similar to and/or substantially the same as one or more portions (and/or combination of portions) of the devices 100, 200, 300, 400, and/or 500 described above. Accordingly, portions of the device 600 may not be described in further detail herein.

The device 600 includes a housing 610, a catheter 630, and an actuator 650. The housing 610 includes and/or houses at least a portion of the catheter 630 disposed, at least partially, in a wound, looped, and/or coiled configuration. The housing 610 includes a first port 611 configured to fixedly receive a proximal end portion 631 of the catheter 630 and a second port 612 configured to movably receive a distal end portion 632 of the catheter 630. The ports 611 and 612 can be any suitable configuration such as any of those described above.

As described above with reference to the housing 510, the housing 610 can include one or more internal structures 614 configured to support, guide, and/or direct at least a portion of the catheter 630 disposed in the housing 610. More particularly, in the embodiment shown in FIGS. 11-13, the internal structure 614 can be, for example, a cylindrical wall, drum, protrusion(s), ridge(s), and/or the like. The internal structure 614 can be configured to provide a structure and/or an axis about which at least a portion of the catheter 630 can be wound, looped, and/or coiled, thereby supporting at least the portion of the catheter 630 as the catheter 630 is moved between a first position and a second position, as described in further detail herein.

The catheter 630 of the device 600 can be any suitable shape, size, and/or configuration. For example, in some embodiments, the catheter 630 can be substantially similar in at least form and/or function to any of the catheters 130, 230, 330, 430, and/or 530 described above. Thus, such similar portions and/or aspects of the catheter 630 may not described in further detail herein. For example, in the embodiment shown in FIGS. 11-13, the catheter 630 can be formed from any suitable material and can have any suitable length, diameter, and/or configuration such as those described above with reference to the catheter 130.

As described above, the catheter 630 or a portion thereof can be moved (e.g., via rotational movement of the actuator 650) between the first position (FIGS. 11 and 12), in which the distal end portion 632 of the catheter 630 is disposed within the housing 610 and/or the second port 612, and a second position (FIG. 13), in which at least a portion of the catheter 630 extends through the second port 612 and at least a portion of an access device coupled to the second port 612. In some embodiments, the catheter 630 can have a length sufficient to place a distal surface of the catheter 630 a predetermined, desired, and/or at least a threshold distance beyond a distal surface of the access device when the catheter 630 is in the second position, as described in detail above with reference to the catheter 130.

The actuator 650 of the device 600 can be any suitable shape, size, and/or configuration. For example, as shown in FIGS. 11-13, the actuator 650 includes a first portion 651 and a second portion 652. The actuator 650 can be coupled to the housing 610 at or near the second port 612 of the housing 610 (e.g., at or near a distal end portion of the housing 610). In other embodiments, the actuator 650 can be coupled to the housing 610 at any suitable position along a length of the housing 610. The actuator 650 can be coupled to the housing 610 in any suitable manner that allows the actuator 650 to be rotated relative to the housing 610. Moreover, the actuator 650 can be coupled to the housing 610 such that the second portion 652 is at least partially disposed within the housing 610 and in contact with and/or otherwise allowed to engage the catheter 630. In this manner, the actuator 650 can be substantially similar in at least form and/or function to the actuator 250 described above with reference to FIGS. 3 and 4.

In use, the device 600 can be in a first configuration and/or state in which the distal end portion of the catheter is 630 is disposed within the housing 610 and/or the second port 612 (FIGS. 11 and 12) and a user can manipulate the device 600 by engaging the first portion 651 of the actuator 650 to place the device 600 in a second configuration and/or state (FIG. 13). For example, the user can exert a force on the first portion 651 of the actuator 650 to rotate the actuator 650 in, for example, a clockwise direction, as indicated by the arrow GG in FIG. 13. As such, the second portion 652 of the actuator 650 rotates relative to the housing 610 and engages the catheter 630 to move the catheter 630 in the distal direction from the first position to the second position, as indicated by the arrow HH in FIG. 13. Thus, when the second port 612 of the housing 610 is coupled to an access device or the like (not shown), the catheter 630 can be advanced to a desired position relative to the access device, as described in detail above with reference to the device 100. Moreover, in some instances, the catheter 630 can be configured to transfer a volume of fluid (e.g., bodily fluid, medicament, saline, etc.) through the catheter 630 between the patient and a fluid source or fluid reservoir connected to the proximal end portion 631 of the catheter 630 via a coupler 633 or the like. In some instances, once a desired volume of fluid has been transferred through the catheter 630, the user can rotate the actuator 650, for example, in a counterclockwise direction to retract and/or move the catheter 630 from the second position to the first position.

FIGS. 14 and 15 are schematic illustrations of a fluid transfer device 700 in a first configuration and second configuration, respectively, according to another embodiment. The fluid transfer device 700 (also referred to herein as "device") can be any suitable shape, size, and/or configuration. For example, at least a portion of the device 700 can be similar to and/or substantially the same as one or more portions (and/or combination of portions) of the devices 100, 200, 300, 400, 500, and/or 600 described above. More specifically, the device 700 can be substantially similar in at least form and/or function to the device 500 described above with reference to FIGS. 9 and 10. Thus, portions of the device 700 may not be described in further detail herein.

The device 700 includes at least a housing 710, a catheter 730, and an actuator 750. The housing 710 can be any suitable configuration. For example, in some embodiments, the housing 710 can have a substantially circular cross-sectional shape. In some embodiments, the housing 710 can be substantially similar in form and/or function to the housing 510 described above. For example, the housing 710 includes a first port 711 and a second port 712. The ports 711 and 712 can be any suitable configuration such as those described above with reference to the first port 511 and the second port 512, respectively. In the embodiment shown in FIGS. 14 and 15, the first port 711 is configured to fixedly receive and/or couple to a proximal end portion 731 of the catheter 730. The second port 712 is configured to movably receive a distal end portion 732 of the catheter 730. Moreover, the second port 712 can be a lock mechanism and/or coupler configured to couple the device 700 to an access device or the like such as, for example, a PIV 705 (e.g., an indwelling PIV), as described above.

The housing 710 can differ from the housing 510, however, in the arrangement and/or placement of the first port 711. For example, as shown in FIGS. 14 and 15, the first port 711 can be disposed in a center or central portion of the housing 710. In other embodiments, however, the first port 711 can be disposed at any other suitable position along the housing 710. Moreover, the housing 710 can be configured to receive at least a portion of the actuator 750 such that the housing 710 and the portion of the actuator 750 collectively define a channel 715 configured to receive at least a portion of the catheter 730, as described in further detail herein. While the channel 715 is shown in FIGS. 14 and 15 as being substantially circular and disposed adjacent to an exterior wall of the housing 710, it should be understood that the channel 715 can be any suitable shape, size, and/or configuration.

The catheter 730 of the device 700 can be any suitable shape, size, and/or configuration. For example, in some embodiments, the catheter 730 can be substantially similar in at least form and/or function to any of the catheters 130, 230, 330, 430, 530, and/or 630 described above. Thus, such similar portions and/or aspects of the catheter 730 may not described in further detail herein. For example, in the embodiment shown in FIGS. 14 and 15, the catheter 730 can be formed from any suitable material and can have any suitable length, diameter, and/or configuration such as those described above with reference to the catheter 130.

At least a portion of the catheter 730 is movably disposed within the housing 710. In some embodiments, the catheter 730 or a portion thereof can be moved (e.g., via rotational movement of the actuator 750) between a first position (FIG. 14), in which the distal end portion 732 of the catheter 730 is disposed within the housing 710 and/or the second port 712, and a second position (FIG. 15), in which at least a portion of the catheter 730 extends through the second port 712 and at least a portion of an access device coupled to the second port 712. In some embodiments, the catheter 730 can have a length sufficient to place a distal surface of the catheter 730 a predetermined, desired, and/or at least a threshold distance beyond a distal surface of the access device when the catheter 730 is in the second position, as described in detail above. In some embodiments, at least a portion of the catheter 730 can be disposed within the housing 710 and can engage at least a portion of the actuator 750 in a manner similar to that of the catheter 530 described in detail above. Thus, the arrangement of the catheter 730 is not described in further detail herein.

The actuator 750 of the device 700 can be any suitable shape, size, and/or configuration. In the embodiment shown in FIGS. 14 and 15, the actuator 750 is movably coupled to the housing 710 and has a spool structure 754 that is movably coupled to the housing 710. The spool structure 754 is at least partially disposed within the housing 710 and is configured to define the channel 715 with a portion of the housing 710, as described above. Moreover, the spool structure 754 is coupled to at least a portion of the catheter 730 (e.g., the proximal end portion 731 of the catheter 730). Although not shown in FIGS. 14 and 15, in some embodiments the spool structure 754 can include a portion disposed outside of the housing 710 and configured to be engaged by a user to rotate the spool structure 754 (and/or the actuator 750) relative to the housing 710. Accordingly, the actuator 750 can be substantially similar in at least form and/or function to the actuator 550 described in detail above with reference to FIGS. 9 and 10. Thus, the actuator 750 is not described in further detail herein.

In some embodiments, the catheter 730 is disposed within the channel 715 and wound around the spool structure 754 of the actuator 750. As such, a rotational movement of the actuator 750 results in a rotational movement of at least a portion of the catheter 730 that is wound or coiled around the spool structure 754. Such an arrangement, in turn, results in a spooling (or unspooling), coiling (or uncoiling), winding (or unwinding), etc. of at least a portion of the catheter 730, thereby moving and/or transitioning the catheter 730 between the first position and the second position. In some implementations, the distal end portion 732 of the catheter 730 can be at least partially disposed within and/or otherwise aligned with the second port 712 such that the rotation of the actuator 750 and the portion of the catheter 730 results in a substantially linear movement of the distal end portion 732 of the catheter 730 relative to, within, and/or through the second port 712.

In use, the device 700 can be in a first configuration or state (FIG. 14) and the user can engage and/or manipulate the device 700 by rotating the actuator 750, thereby transitioning the device from the first configuration or state to the second configuration or state (FIG. 15). More specifically, user can rotate the actuator 750 (and thus, the spool structure 754) in a clockwise direction, as indicated by the arrows II in FIG. 15. The rotation of the actuator 750 moves the catheter 730 from the first position and the second position. With the proximal end portion 731 of the catheter 730 fixedly coupled to the first port 711 and the distal end portion 732 of the catheter 730 configured to move relative to the housing 710, rotating the actuator 750, for example, advances a portion of the catheter 730 along and/or through the channel 715, which in turn, moves the distal end portion 732 of the catheter 730 relative to the second port 712 and/or the access device coupled thereto, as indicated by the arrow JJ in FIG. 15. Thus, the device 700 can be substantially similar in at least form and/or function to the device 500 described in detail above.

While the device 700 shown in FIGS. 14 and 15 is described as being actuated and/or used by turning the actuator 750, and more specifically, the spool structure 754, in other embodiments, a device can include any number of actuators and/or actuator portions which can collectively act to move and/or transition the catheter 730 between the first position and the second position. For example, FIGS. 16 and 17 illustrate a fluid transfer device 800 according to another embodiment in a first configuration and a second configuration, respectively. In this embodiment, the device 800 can be substantially similar in structure and/or function to the device 700 except for the inclusion of one or more additional actuators and/or actuator portions.

The fluid transfer device 800 (also referred to herein as "device") can be any suitable shape, size, and/or configuration. For example, at least a portion of the device 800 can be similar to and/or substantially the same as one or more portions (and/or combination of portions) of the devices 100, 200, 300, 400, 500, 600, and/or 700 described above. For example, as described in further detail herein, the device 800 can be a combination of certain portions and/or aspects of the devices 200 and 700. Thus, portions of the device 800 may not be described in further detail herein.

The device 800 includes at least a housing 810, a catheter 830, and an actuator 850. The housing 810 can be any suitable configuration. For example, in some embodiments, the housing 810 can have a substantially circular cross-sectional shape. In some embodiments, the housing 810 can be substantially similar in form and/or function to the housing 710 described above. For example, the housing 810 includes a first port 811 configured to be fixedly coupled to a proximal end portion 831 of the catheter 830 and a second port 812 configured to receive a distal end portion 832 of the catheter 830, as described above with reference to the device 700. Thus, the housing 810 and/or aspects thereof are not described in further detail herein.

The catheter 830 of the device 800 can be any suitable shape, size, and/or configuration. For example, in some embodiments, the catheter 830 can be substantially similar in at least form and/or function to any of the catheters 130, 230, 330, 430, 530, 630, and/or 730 described above. Thus, such similar portions and/or aspects of the catheter 830 may not described in further detail herein. For example, in the embodiment shown in FIGS. 16 and 17, the catheter 630 can be formed from any suitable material and can have any suitable length, diameter, and/or configuration such as those described above with reference to the catheter 130.

At least a portion of the catheter 830 is movably disposed within the housing 810. In some embodiments, the catheter 830 or a portion thereof can be moved (e.g., via rotational movement of the actuator 850) between a first position (FIG. 16), in which the distal end portion 832 of the catheter 830 is disposed within the housing 810 and/or the second port 812, and a second position (FIG. 17), in which at least a portion of the catheter 830 extends through the second port 812 and at least a portion of an access device coupled to the second port 812. In some embodiments, the catheter 830 can have a length sufficient to place a distal surface of the catheter 830 a predetermined, desired, and/or at least a threshold distance beyond a distal surface of the access device when the catheter 830 is in the second position, as described in detail above. In some embodiments, at least a portion of the catheter 830 can be disposed within the housing 810 and can engage at least a portion of the actuator 850 in a manner similar to that of the catheter 730 described in detail above. Thus, the arrangement of the catheter 830 is not described in further detail herein.

The actuator 850 of the device 800 can be any suitable shape, size, and/or configuration. In the embodiment shown in FIGS. 16 and 17, the actuator 850 is movably coupled to the housing 810 and has a spool structure 854 that is movably coupled to the housing 810. The spool structure 854 is at least partially disposed within the housing 810 and is configured to define a channel 815 with a portion of the housing 810. Moreover, the spool structure 854 is coupled to at least a portion of the catheter 830 (e.g., the proximal end portion 831 of the catheter 830). In this manner, the spool structure 854 can be substantially similar to the spool structure 754 described above with reference to FIGS. 14 and 15.

The actuator 850 can differ from the actuator 750, however, by including a second actuator 850A. The second actuator 850A includes a first portion 851 and a second portion 852. In the embodiment shown in FIGS. 16 and 17, the second actuator 850 can be used to move or transition the catheter 830 between the first position and the second position. The second actuator 850A can be coupled to the housing 810 at or near the second port 812 of the housing 810 (e.g., at or near a distal end portion of the housing 810). The second actuator 850A can be coupled to the housing 810 in any suitable manner that allows the second actuator 850A to be rotated relative to the housing 810. Moreover, the second portion 852 of the second actuator 850A is at least partially disposed within the housing 810 and in contact with and/or otherwise allowed to engage the catheter 830. In this manner, the second actuator 850A can be substantially similar in at least form and/or function to the actuator 250 described above with reference to FIGS. 3 and 4.

In use, the second actuator 850A can be rotated relative to the housing 810 to advance the catheter 830 from the first position to the second position. The rotation of the first portion 851 of the actuator 850 in the clockwise direction (indicated by the arrow KK in FIG. 17) advances the portion of the catheter 850 engaged with the second portion 852 of the actuator 850 (e.g., in response to a friction force therebetween). The advancement of the portion of the catheter 850 in turn results in a tugging force of the portion of the catheter 850 disposed within the portion of the channel 815 defined by the spool structure 854 and the housing 810. As such, the spool structure 854 is similarly rotated in the clockwise direction, thereby resulting in a gradual release of the portion of the catheter 850 disposed in the portion of the channel 815. Accordingly, actuating and/or rotating the second actuator 850A advances at least the distal end portion 832 of the catheter 830 in or along a linear path through the second port 812 of the housing 810, as indicated by the arrow LL in FIG. 17.

Figure 18:
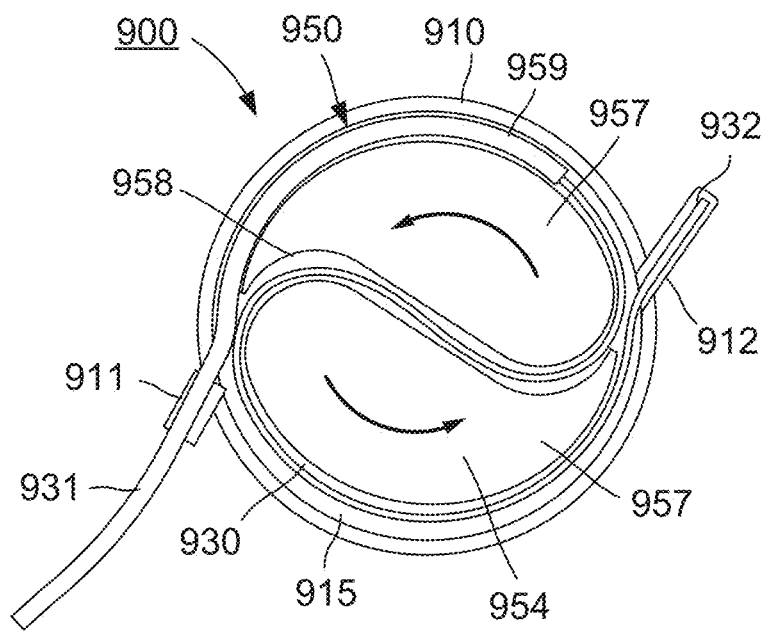
FIGS. 18-20 are schematic illustrations of a fluid transfer device as the fluid transfer device transitions from a first configuration (FIG. 18) to a second configuration (FIG. 20), according to an embodiment.
Figure 19:
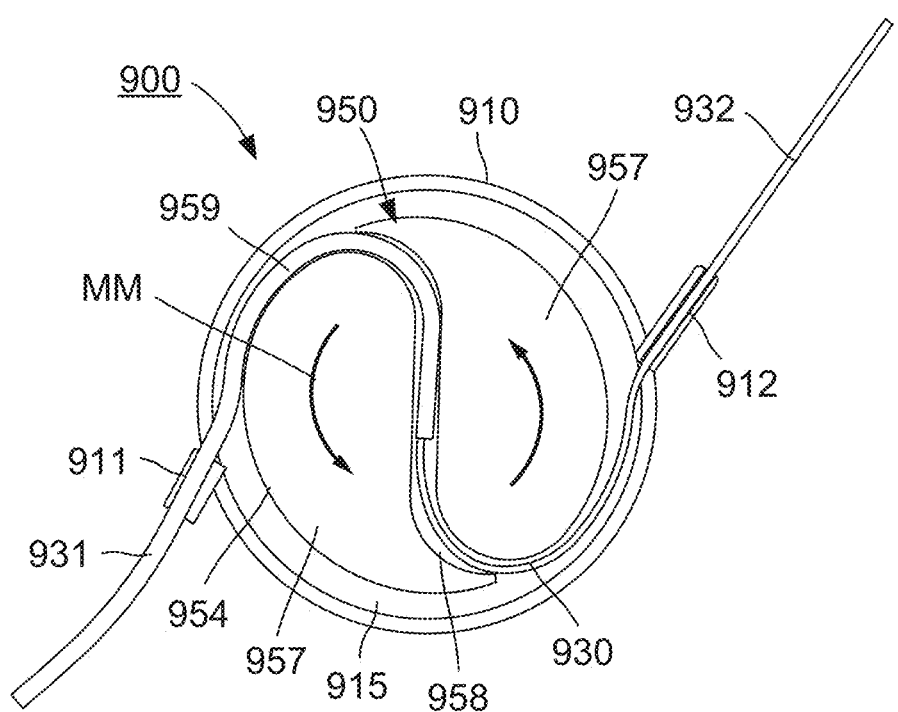
Figure 20:
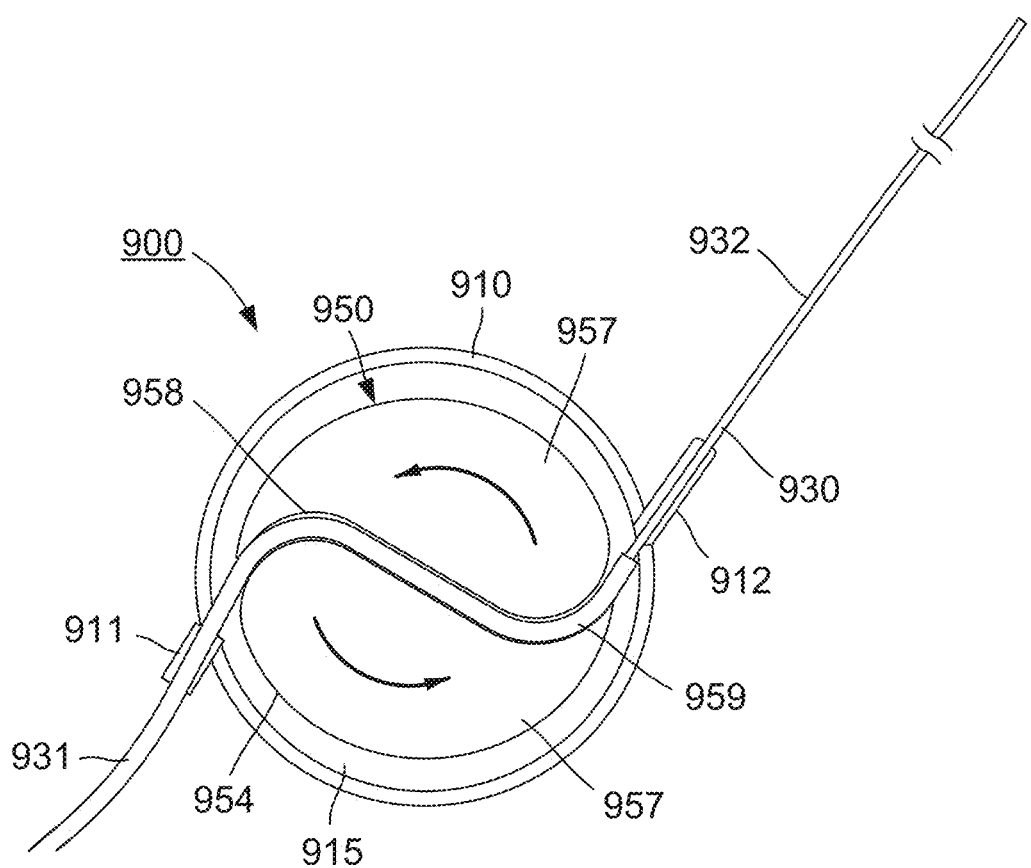

While the catheter 830 is shown in FIGS. 16 and 17 as being at least partially spooled or wound around the spool structure 854 (e.g., around an exterior of the spool structure 854), in other embodiments, a device can include an actuator that has a spool structure configured to engage a catheter in any suitable manner. For example, FIGS. 18-20 illustrate a device 900 according to another embodiment. The fluid transfer device 900 (also referred to herein as "device") can be any suitable shape, size, and/or configuration. For example, at least a portion of the device 900 can be similar to and/or substantially the same as one or more portions (and/or combination of portions) of the devices 100, 200, 300, 400, 500, 600, 700, and/or 800 described above. Thus, portions of the device 900 may not be described in further detail herein.

The device 900 includes at least a housing 910, a catheter 930, and an actuator 950. The housing 910 can be any suitable configuration. For example, in some embodiments, the housing 910 can have a substantially circular cross-sectional shape. In some embodiments, the housing 910 can be substantially similar in at least form and/or function to the housings 710 and/or 810 described above. For example, the housing 910 includes a first port 911 configured to be coupled to and/or to otherwise receive a proximal end portion 931 of the catheter 930 and a second port 912 configured to receive a distal end portion 932 of the catheter 930. In some embodiments, the first port 911 can be configured to fixedly couple to the proximal end portion 931 of the catheter 930, as described above with reference to the devices 700 and/or 800. Thus, the housing 910 and/or aspects thereof are not described in further detail herein.

The catheter 930 of the device 900 can be any suitable shape, size, and/or configuration. For example, in some embodiments, the catheter 930 can be substantially similar in at least form and/or function to any of the catheters 130, 230, 330, 430, 530, 630, 730, and/or 830 described above. Thus, such similar portions and/or aspects of the catheter 930 may not described in further detail herein. For example, in the embodiment shown in FIGS. 18-20, the catheter 930 can be formed from any suitable material and can have any suitable length, diameter, and/or configuration such as those described above with reference to the catheter 130.

At least a portion of the catheter 930 is movably disposed within the housing 910. In some embodiments, the catheter 930 or a portion thereof can be moved (e.g., via rotational movement of the actuator 950) between a first position (FIG. 18), in which the distal end portion 932 of the catheter 930 is disposed within the housing 910 and/or the second port 912, and a second position (FIG. 20), in which at least a portion of the catheter 930 extends through the second port 912 and at least a portion of an access device (not shown) coupled to the second port 912. In some embodiments, the catheter 930 can have a length sufficient to place a distal surface of the catheter 930 a predetermined, desired, and/or at least a threshold distance beyond a distal surface of the access device when the catheter 930 is in the second position, as described in detail above. In some embodiments, at least a portion of the catheter 930 can be disposed within the housing 910 and can engage at least a portion of the actuator 950, as described in further detail herein.

The actuator 950 of the device 900 can be any suitable shape, size, and/or configuration. In the embodiment shown in FIGS. 18-20, the actuator 950 has a spool structure 954 that is movably coupled to the housing 910. The spool structure 954 can be coupled to, can receive, and/or otherwise can engage at least a portion of the catheter 930 (e.g., the proximal end portion 931 of the catheter 930) to move the catheter 930 between a first position and a second position, as described in further detail herein. As shown, for example, in FIG. 18, the spool structure 954 is at least partially disposed within the housing 910 such that the spool structure 954 and the housing 910 collectively define an outer channel 915. More specifically, the spool structure 954 can be sized and positioned within the housing 910 such that an exterior or outer portion and/or surface of the spool structure 954 is spaced apart from an interior or inner portion and/or surface of the housing 910 (e.g., an inner perimeter). The space, in turn, forms and/or defines the outer channel 915, which is configured to receive at least a portion of the catheter 930, as described in further detail herein.

The spool structure 954 includes a set of engagement structures 957 configured to selectively engage a portion of the catheter 930 within the housing 930. More specifically, in the embodiment shown in FIGS. 18-20, the set of engagement structures 957 includes a pair of engagement structures 957 that can have any suitable size, shape, and/or configuration. For example, the engagement structures 957 can have substantially the same size and/or shape such as, for example, a teardrop-shape, as shown in FIGS. 18-20. The engagement structures 957 can be disposed in a mirrored arrangement relative to each other such that the spool structure 954 defines an inner channel 958 or pathway between the pair of engagement structures 957 that is configured to movably receive a portion of the catheter 930. The inner channel 958 can be, for example, a serpentine, circuitous, tortuous, and/or otherwise curved or non-linear channel or pathway that at least partially corresponds to a size and/or shape of a portion of the engagement structures 957.

The catheter 930 is disposed within the housing 910 such that a portion of the catheter 930 is disposed within at least one of the outer channel 915 and/or the inner channel 958 and is configured to be advanced therethrough (e.g., through the housing 910) in response to actuation of the actuator 950. For example, FIG. 18 illustrates the device 900 in a first configuration and/or state in which the catheter 930 is in the first position. As shown, when the catheter 930 is in the first position, a portion of the catheter 930 can extend from the first port 911, through at least a portion of the outer channel 915, through the inner channel 958, and at least partially into the second port 912. As shown in FIGS. 18-20, rotating the spool structure 954 rotates the engagement structures 957 (and the inner channel 958) relative to the first port 911 and the second port 912 of the housing 910.

As shown in FIG. 18, the arrangement of the catheter 930 when the device 900 is in the first configuration and/or state is such the proximal end portion 931 of the catheter 930 extends from the first port 911 and is disposed within and/or passes through a first portion the outer channel 915, a medial portion of the catheter 930 is disposed within and passes through the inner channel 958, and a third portion of the catheter 930 is disposed within and passes through a second portion of the outer channel 915 such that the distal end portion 932 of the catheter 930 is at least partially disposed within the second port 912 of the housing 910. As such, while the inner channel 958 is at least partially aligned with at least one of the first port 911 and/or the second port 912, the catheter 930 passes around one of the engagement structures 957 prior to entering and/or being disposed within the inner channel 958. In this position and/or orientation, the path through which the catheter 930 extends between the first port 911 and the second port 912 is, for example, the longest or substantially the longest path between the first port 911 and the second port 912. Thus, the largest or substantially the largest portion of the catheter 930 is disposed within the housing 910 when the device 900 is in the first configuration and/or state (e.g., when the catheter 930 is in the first position).

As shown in FIG. 19, the device 900 can be transitioned from the first configuration and/or state by rotating the actuator 950 in a counterclockwise direction, as indicated by the arrow MM in FIG. 19. The rotation of the actuator 950 results in a rotation of the engagement structures 957, which in turn, changes a portion of the outer channel 915 that is disposed between the first port 911 and a first end portion of the inner channel 958 and a portion of the outer channel 915 that is disposed between the second port 912 and a second end portion of the inner channel 958 opposite the first end portion. More specifically, the portions of the outer channel 915 are reduced, which in turn, is operable to advance the catheter 930 through a serpentine, circuitous, tortuous, and/or otherwise curved or non-linear path collectively formed and/or defined by the outer channel 915 and the inner channel 958 from its first position toward its second position.

As shown in FIG. 20, the actuator 950 can be actuated (e.g., rotated) a predetermined and/or desired amount to place the device 900 in a second configuration and/or state in which the catheter 930 is in the second position. More specifically, in some implementations, the device 900 can be in the second configuration and/or state when rotation of the actuator 950 results in the end portions of the inner channel 958 being at least partially aligned with the first port 911 or the second port 912. In this position and/or orientation, the inner channel 958 can define, for example, the shortest path through the housing 910 between the first port 911 and the second port 912. As shown, the catheter 930 extends along the path when the device 900 is in the second configuration and/or state such that the smallest or substantially the smallest portion of the catheter is disposed in the housing 910. As described in detail above with reference to previous embodiments, the arrangement of the device 900 can allow the catheter 930 to have a length or "reach" that can be longer than, for example, the housing 910 and/or a length of the housing 910 between the first port 911 and the second port 912. Thus, when the second port 912 of the housing 910 is coupled to an access device or the like (not shown), the catheter 930 can be advanced to a desired position relative to the access device regardless of a type and/or length of the access device, as described in detail above with reference to the device 100.

Figure 21:
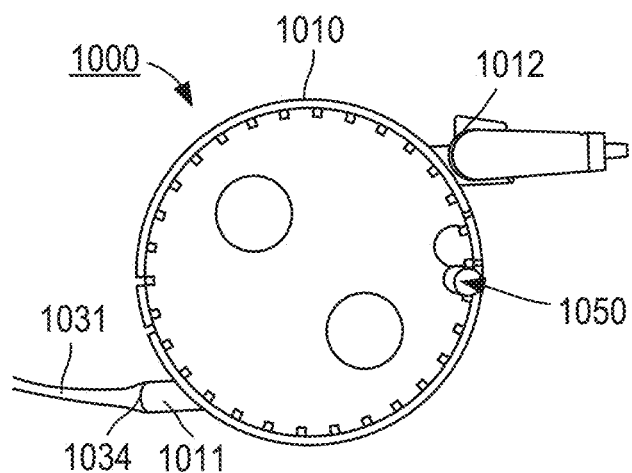
FIGS. 21 and 22 are side view illustrations of a fluid transfer device in a first configuration and a second configuration, respectively, according to an embodiment.
Figure 22:
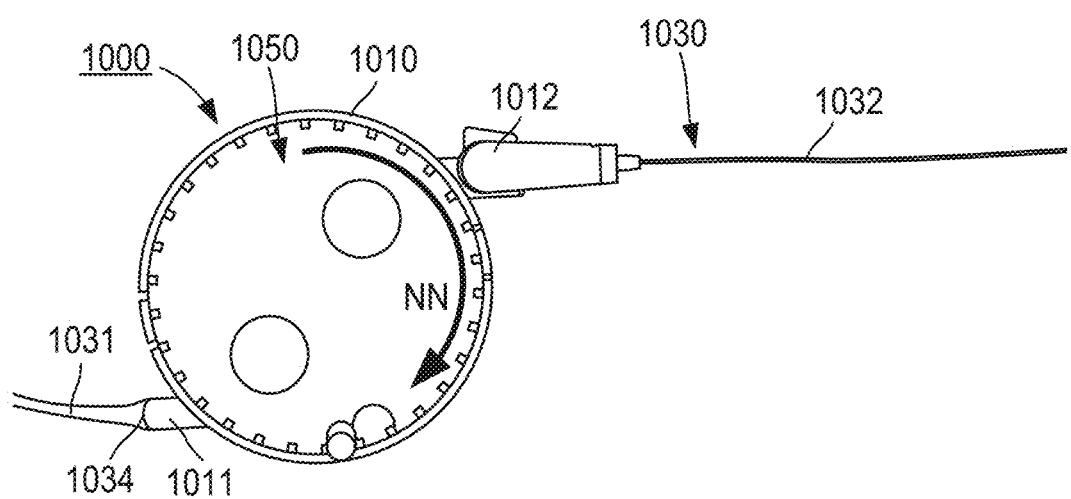
Figure 23:
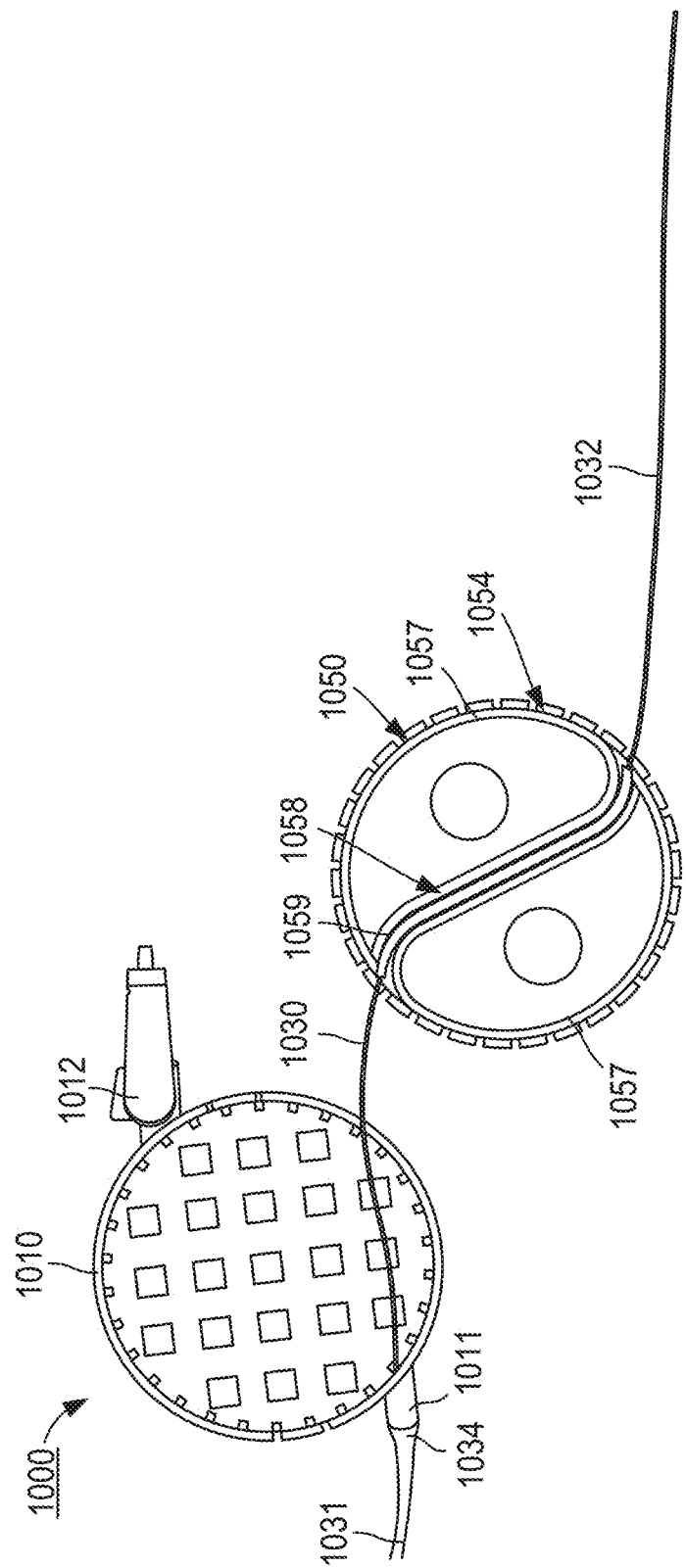
FIG. 23 is a partially exploded side view of the fluid transfer device of FIGS. 21 and 22.

FIGS. 21-23 illustrate a fluid transfer device 1000 according to another embodiment. The fluid transfer device 1000 (also referred to herein as "device") can be similar to and/or substantially the same as the device 900 described above with reference to FIGS. 18-20. Accordingly, while portions and/or aspects of the device 1000 are identified below such portions and/or aspects may not be described in further detail.

As shown, the device 1000 includes a housing 1010, a catheter 1030, and an actuator 1050. The housing 1010 can be substantially similar to the housing 910 described in detail above. For example, the housing 1010 includes a first port 1011 that can be fixedly coupled to a proximal end portion 1031 of the catheter 1030 and includes a second port 1012 that can movably receive a distal end portion 1032 of the catheter 1030. The catheter 1030 can be substantially similar to the catheter 930 described in detail above. For example, as shown in FIG. 23, the catheter 1030 is at least partially disposed within the housing 1010 and is configured to be engaged by at least a portion of the actuator 1050 and/or is configured to be disposed within a space, one or more channels, one or more lumens, one or more volumes, etc. defined by the housing 1010, the actuator 1050, and/or collectively defined by the housing 1010 and actuator 1050, as described in further detail herein.

In some embodiments the catheter 1030 can be formed of a single material and can have a predetermined length, diameter, and/or configuration such as those described above with respect to the catheter 130. In other embodiments, the catheter 1030 can be formed of different materials and/or can have different size, shape, diameter, thickness, etc. to result in any suitable stiffness, flexibility, hardness, and/or durometer. For example, the proximal end portion 1031 of the catheter 1030 can be formed from a relatively flexible material which can deform in response to a sudden change in pressure reducing the likelihood of collapsing the catheter 1030 at a location downstream to the proximal end portion. The distal end portion of the catheter 1032 can be formed from a relatively rigid material or a material having a stiffness and/or rigidity that is at least greater than stiffness and/or rigidity of the proximal end portion 1031 and can have a diameter smaller than that of the proximal end portion 1031 to facilitate advancing the catheter 1030 to and from a desired position relative to a PIV. In some embodiments, the proximal end portion 1031 and the distal end portion 1032 of the catheter 1030 can be separate components having a different length, diameter, stiffness, flexibility, material, and/or configuration, which can be mechanically and fluidically connected using adapter 1034 located within the first port 1011, as shown in FIGS. 21-23.

The actuator 1050 can be substantially similar to the actuator 950 described in detail above. For example, the actuator 1050 includes a spool structure 1054 having a pair of engagement structures 1057 that are disposed in a mirrored orientation relative to each other such that an inner channel 1058 or path is defined therebetween. In some embodiments, the actuator 1050 can include a tube, introducer, sheath, and/or the like disposed within the inner channel 1058 and configured to support and guide the catheter 1030, limiting and/or substantially preventing undesired deformation and/or deflection of a portion of the catheter 1030 as the device is transitioned between a first configuration to a second configuration. In some embodiments, one or more surfaces of the actuator 1050 and/or spool structure 1054 can selectively contact and/or otherwise support the catheter 1030 as a portion of the catheter is moved through the housing.

As described above with reference to the device 900, the device 1000 is configured to be transitioned from a first configuration and/or state (FIG. 21) in response to rotation of the actuator 1050, as indicated by the arrow NN. The catheter 1030 is configured to be in a first position when the device 1000 is in the first configuration and/or state such that a largest or substantially the largest portion or length of the catheter 1030 is disposed within the housing 1010 between the first port 1011 and the second port 1012.

In some instances, the user can rotate the actuator 1050 to place the device 1000 in a second configuration and/or state (FIG. 22). The catheter 1030 is configured to be in a second position when the device 1000 is in the second configuration and/or state such that a smallest or substantially the smallest portion or length of the catheter 1030 is disposed within the housing 1010 between the first port 1011 and the second port 1012. Moreover, as described in detail above, the distal end portion 1032 of the catheter 1030 can be placed in a desired position (e.g., a distal position) relatively to the second port 1012 and/or an access device coupled to the second port 1012 when the catheter 1030 is in the second position.

While the engagement structures 957 and/or 1057 are shown and described above as being substantially the same size, shape, and/or configuration and arranged in a mirrored orientation relative to each other, in other embodiments, a spool structure can include a set of engagement structures in which each engagement structure can have any suitable shape, size, and/or configuration. For example, FIGS. 24 and 25 a fluid transfer device 1100 according to another embodiment. The fluid transfer device 1100 (also referred to herein as "device") can be any suitable shape, size, and/or configuration. For example, at least a portion of the device 1100 can be similar to and/or substantially the same as one or more portions (and/or combination of portions) of the devices 100, 200, 300, 400, 500, 600, 700, 800, 900, and/or 1000 (or any suitable combinations thereof) described above. Thus, portions of the device 1100 may not be described in further detail herein.

The device 1100 includes at least a housing 1110, a catheter 1130, and an actuator 1150. The housing 1110 can be any suitable configuration. For example, in some embodiments, the housing 1110 can have a substantially circular cross-sectional shape. In some embodiments, the housing 1110 can be substantially similar in at least form and/or function to the housings 910 and/or 1010 described above. For example, the housing 1110 includes a first port 1111 configured to be coupled to and/or to otherwise receive a proximal end portion 1131 of the catheter 1130 and a second port 1112 configured to receive a distal end portion 1132 of the catheter 1130. In some embodiments, the first port 1111 can be configured to fixedly couple to the proximal end portion 1131 of the catheter 1130, as described above with reference to the device 900. Thus, the housing 1110 and/or aspects thereof are not described in further detail herein.

The catheter 1130 of the device 1100 can be any suitable shape, size, and/or configuration. For example, in some embodiments, the catheter 1130 can be substantially similar in at least form and/or function to any of the catheters 130, 230, 330, 430, 530, 630, 730, 830, 930, and/or 1030 described above. Thus, such similar portions and/or aspects of the catheter 1130 may not described in further detail herein. For example, in the embodiment shown in FIGS. 24 and 25, the catheter 1130 can be formed from any suitable material and can have any suitable length, diameter, and/or configuration such as those described above with reference to the catheter 130.

At least a portion of the catheter 1130 is movably disposed within the housing 1110. In some embodiments, the catheter 1130 or a portion thereof can be moved (e.g., via rotational movement of the actuator 1150) between a first position (FIG. 24), in which the distal end portion 1132 of the catheter 1130 is disposed within the housing 1110 and/or the second port 1112, and a second position (FIG. 25), in which at least a portion of the catheter 1130 extends through the second port 1112 and at least a portion of an access device (not shown) coupled to the second port 1112. In some embodiments, the catheter 1130 can have a length sufficient to place a distal surface of the catheter 1130 a predetermined, desired, and/or at least a threshold distance beyond a distal surface of the access device when the catheter 1130 is in the second position, as described in detail above.

The actuator 1150 of the device 1100 can be any suitable shape, size, and/or configuration. In some embodiments, the actuator 1150 can be substantially similar in at least form and/or function to the actuator 950 described in detail above. For example, in the embodiment shown in FIGS. 24 and 25, the actuator 1150 has a spool structure 1154 that is movably coupled to the housing 1110. The spool structure 1154 includes a first engagement structure 1157A and a second engagement structure 1157B configured to selectively engage a portion of the catheter 1130 within the housing 1110. As described above with reference to the actuator 950, the spool structure 1154 can be at least partially disposed within the housing 1110 such that the spool structure 1154 and the housing 1110 collectively define an outer channel 1115. The spool structure 1154 can be configured to guide, direct, and/or engage at least a portion of the catheter 1130 that is disposed within the housing 1110, as described in further detail herein. Moreover, the catheter 1130 can be spooled, wound, and/or wrapped around the spool structure 1154 in a manner substantially similar to the manner in which the catheter 930 is spooled, wound, and/or wrapped around the spool structure 954. Accordingly, rotation of the actuator 1150 in a counterclockwise direction (indicated as arrow OO in FIG. 24) is operable to move the catheter 1130 from the first position (FIG. 24) to the second position (FIG. 25).

While the engagement structures 957 and 1057 are described above as being substantially the same shape, size, and/or configuration, in the embodiment shown in FIGS. 24 and 25, the engagement structures 1157A and 1157B are different shapes, sizes, and/or configurations. For example, the arrangement of the spool structure 1154 is such that the first engagement structure 1157A is larger than the second engagement structure 1157B. The engagement structures 1157 can be disposed in a mirrored arrangement relative to each other such that the spool structure 1154 defines an inner channel 1158 or pathway between the engagement structures 1157A and 1157B that is configured to movably receive a portion of the catheter 1130.

In some embodiments, the size and/or shape of the engagement structures 1157A and 1157B, and thus, the position of the inner channel 1158 can be based at least in part on a location or position of at least one of the first port 1111 or the second port 1112 of the housing 1110. For example, as shown in FIGS. 24 and 25, a size of at least the second engagement portion 1158 can be based in a part on and/or can substantially correspond to a distance between the first port 1111 and the second port 1112. In some embodiments, the size and/or shape of the engagement structures 1157A and/or 1157B can be such that each end portion of the inner channel 1158 is substantially aligned with at least one of the first port 1111 or the second port 1112 when the device 1100 is in each of the first configuration and/or state and the second configuration and/or state, as shown in FIGS. 24 and 25, respectively. In some embodiments, increasing or decreasing the size or shape of the engagement structures 1157A and 1157B can, for example, increase or decrease, respectively, a length or "reach" of the catheter 1130. For example, a path at least partially defined by the inner channel 1158 between the first port 1111 and the second port 1112 of the housing 1110 can be shorter than the path at least partially defined by the inner channel 958 between the first port 911 and the second port 912. Accordingly, one means of tuning a length and/or reach of a catheter can be increasing and/or decreasing a size and/or shape of the engagement structures.

Figure 26:
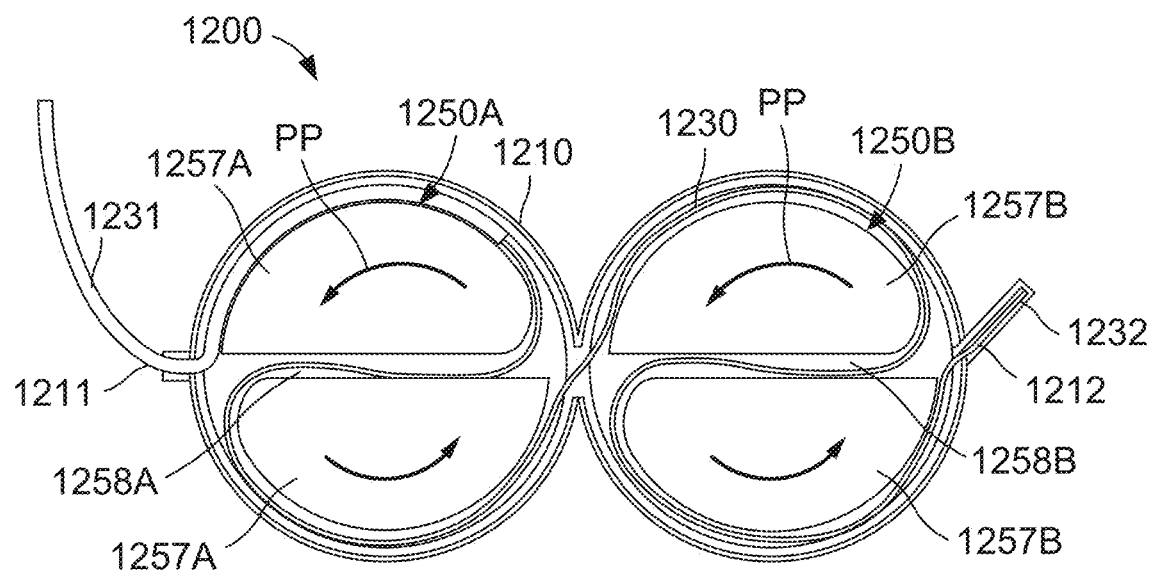
FIG. 26 is a schematic illustration of a fluid transfer device according to an embodiment.

FIG. 26 illustrates a fluid transfer device 1200 according to another embodiment. The fluid transfer device 1200 (also referred to herein as "device") can be any suitable shape, size, and/or configuration. For example, at least a portion of the device 1200 can be similar to and/or substantially the same as one or more portions (and/or combination of portions) of the devices 100, 200, 300, 400, 500, 600, 700, 800, 900, 1000, and/or 1100 (or any suitable combinations thereof) described above. More specifically, at the device 1200 can be substantially similar in at least form and/or function to the device 900, 1000, and/or 1100 described in detail above. Thus, portions of the device 1200 may not be described in further detail herein.

The device 1200 can differ from the device 900, however, in that the device 1200 is, for example, two devices coupled together with a single catheter passing therethrough. As shown, the device 1200 includes at least a housing 1210, a catheter 1230, a first actuator 1250A and a second actuator 1250B. The housing 1210 can be any suitable configuration. In some embodiments, the housing 1210 and/or portions thereof can be substantially similar in at least form and/or function to the housings 910, 1010, and/or 1110 described above. The housing 1210 can differ from the housings 910, 1010, and/or 1110 in that the housing 1210 is, for example, two housings coupled together. For example, the housing 1210 can include a first portion configured to receive the first actuator 1250A and a second portion configured to receive the second actuator 1250B. The first portion of the housing 1210 includes and/or is coupled to a first port 1211 that can be fixedly coupled to a proximal end portion 1231 of the catheter 1230. The second portion of the housing 1210 includes and/or is coupled to a second port 1212 that can movably receive a distal end portion 1232 of the catheter 1230. Accordingly, a portion of the catheter 1230 is configured to be disposed within the first and second portions of the housing 1210 (e.g., along a path inside the housing 1210 defined between the first port 1211 and the second port 1212).

The catheter 1230 of the device 1200 can be any suitable shape, size, and/or configuration. For example, in some embodiments, the catheter 1230 can be substantially similar in at least form and/or function to any of the catheters 130, 230, 330, 430, 530, 630, 730, 830, 930, 1030, and/or 1130 described above. As shown in FIG. 26, the catheter 1230 is at least partially disposed within the housing 1210 and is configured to engage or be engaged by at least a portion of the one or more actuators. For example, in some embodiments, the form and/or arrangement of the catheter 1230 within the housing 1210 can be substantially similar to the form and/or arrangement to the catheter 930 described in detail above.

The first actuator 1250A is disposed within the first portion of the housing 1210 and includes a set of engagement structures 1257A. More specifically, the first actuator 1250A includes a pair of engagement structures 1257A that are disposed in a mirrored orientation relative to each other such that a first inner channel 1258A or path is defined there between, as described in detail above with reference to the actuator 950. In the embodiment shown in FIG. 26, the engagement structures 1257A can have, for example, a hemispherical shape. In other embodiments, the engagement structures can be any suitable shape and/or size such as, for example, teardrop-shaped and/or any other suitable shape. The second actuator 1250B is disposed with in the second portion of the housing 1210 and includes a set of engagement structures 1257B. The engagement structures 1257B can be substantially similar in shape, size, and/or configuration to the engagement structures 1257A. Accordingly, the engagement structures 1257B define a second inner channel 1258B therebetween.

As described above with reference to the devices 900, 1000, and/or 1100, the device 1200 is configured to be transitioned from a first configuration and/or state to a second configuration and/or state in response to rotation of the actuator 1250, as indicated by the arrow PP. The catheter 1230 is configured to be in a first position when the device 1200 is in the first configuration and/or state such that a largest or substantially the largest portion or length of the catheter 1230 is disposed within the housing 1210 between the first port 1211 and the second port 1212 (e.g., within one or more lumen (e.g., an outer channel or portion thereof) defined by the housing 1210 and/or the inner channels 1258A and 1258B). The catheter 1230 is configured to be in a second position when the device 1200 is in the second configuration and/or state such that a smallest or substantially the smallest portion or length of the catheter 1230 is disposed within the housing 1210 between the first port 1211 and the second port 1212. Although not shown, in the embodiment shown in FIG. 26, the device 1200 can be configured such that the catheter 1230 extends along a substantially straight path at least partially defined by the inner channels 1258A and 1258B between the first port 1211 and the second port 1212 when the device 1200 is in the second configuration and/or state. Moreover, as described in detail above, the distal end portion 1232 of the catheter 1230 can be placed in a desired position (e.g., a distal position) relatively to the second port 1212 and/or an access device coupled to the second port 1212 when the catheter 1230 is in the second position. In some implementations, the arrangement and/or configuration of the device 1200 can allow the catheter 1230 to have an increased length relative to, for example, the catheter lengths of the devices 900, 1000, and/or 1100.

Figure 27:
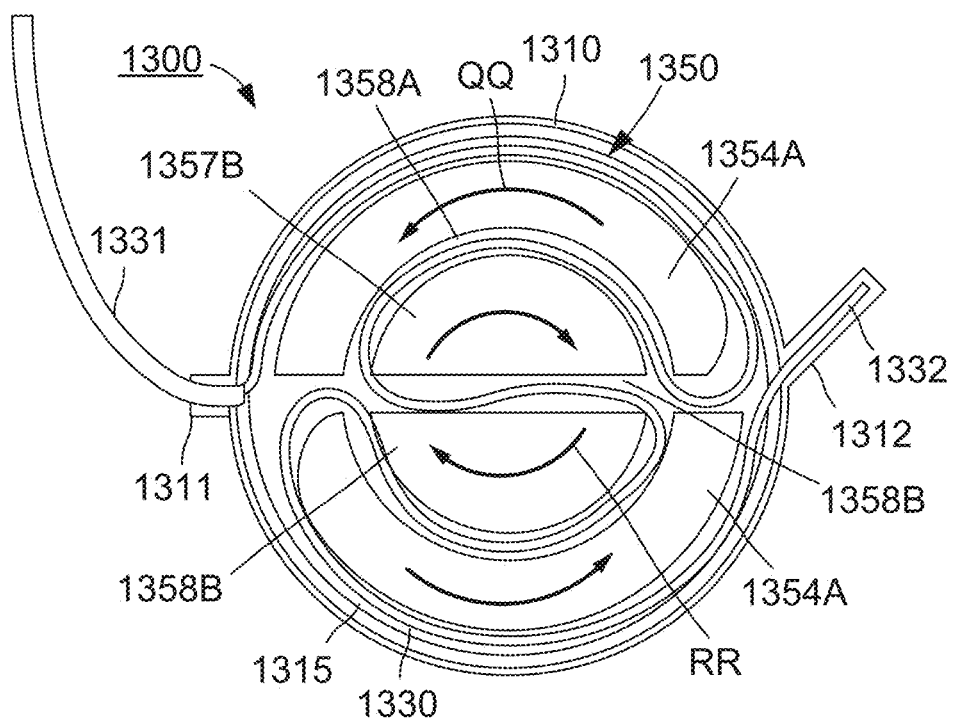
FIG. 27 is a schematic illustration of a fluid transfer device according to an embodiment.

FIG. 27 illustrates a fluid transfer device 1300 according to another embodiment. The fluid transfer device 1300 (also referred to herein as "device") can be any suitable shape, size, and/or configuration. For example, at least a portion of the device 1300 can be similar to and/or substantially the same as one or more portions (and/or combination of portions) of the devices 100, 200, 300, 400, 500, 600, 700, 800, 900, 1000, 1100, and/or 1200 described above. More specifically, the device 1300 can be substantially similar in at least form and/or function to the devices 900, 1000, 1100, and/or 1200 (or any suitable combinations thereof) described in detail above. Thus, portions of the device 1300 may not be described in further detail herein.

As shown, the device 1300 includes at least a housing 1310, a catheter 1330, and an actuator 1350. The housing 1310 can be any suitable configuration. In some embodiments, the housing 1310 and/or portions thereof can be substantially similar in at least form and/or function to the housings 910, 1010, and/or 1110 described above. For example, the housing 1310 includes a first port 1311 configured to fixedly receive a proximal end portion 1331 of the catheter 1330 and a second port 1312 configured to receive a distal end portion 1332 of the catheter 1330. Thus, portions and/or aspects of the housing 1310 may not described in further detail herein.

The catheter 1330 of the device 1300 can be any suitable shape, size, and/or configuration. For example, in some embodiments, the catheter 1330 can be substantially similar in at least form and/or function to any of the catheters 130, 230, 330, 430, 530, 630, 730, 830, 930, 1030, 1130, and/or 1230 described above. As shown in FIG. 27, the catheter 1330 is at least partially disposed within the housing 1310 and is configured to engage or be engaged by at least a portion of the actuator 1350. For example, in some embodiments, the form and/or arrangement of the catheter 1330 within the housing 1310 can be substantially similar to the form and/or arrangement to the catheter 930 described in detail above.

The actuator 1350 of the device 1300 can be any suitable shape, size, and/or configuration. In some embodiments, the actuator 1350 can be substantially similar in at least form and/or function to the actuators 950, 1050, 1150, and/or 1250 described in detail above. The actuator 1350 can differ from the actuators 950, 1050, 1150, and/or 1250, however, by including a first spool structure 1354A and a second spool structure 1354B. Each of the spool structures 1354A and 1354B includes a pair of engagement structures 1357A and 1357B, respectively. The engagement structures 1357A and 1357B can be any suitable shape, size, and/or configuration. Moreover, the engagement structures 1357A collectively define at least a portion of a first inner channel 1358A and the engagement structures 1357B collectively define at least a portion of a second inner channel 1358B, as described above with reference to the devices 900, 100, 1100, and/or 1200.

As shown in FIG. 27, the spool structures 1354A and 1354B are configured to be disposed in the housing 1310 in a concentric arrangement. For example, the first spool structure 1354A can be disposed in the housing 1310 such that an outer channel 1315 is collectively defined by an outer surface of the first spool structure 1354A and an inner surface of the housing 1310, as described above with reference to the device 900. The second spool structure 1354B is at least partially disposed within the first spool structure 1354A (e.g., between the pair of engagement structures 1357A). Moreover, the arrangement of the second spool structure 1354B within the first spool structure 1357A is such that at least a portion of the first inner channel 1358A is collectively defined by an inner surface of the engagement structures 1357A of the first spool structure 1354A and an outer surface of the engagement structures 1357B of the second spool structure 1354B.

As described above with reference to the actuator 950, the spool structure 1354A and 1354B can be at least partially disposed within the housing 1310 and configured to guide, direct, and/or engage at least a portion of the catheter 1330 that is disposed within the housing 1310. For example, the catheter 1330 can be spooled, wound, and/or wrapped around the spool structure 1354A and 1354B such that when the catheter 1330 is in a first configuration and/or position, a portion of the catheter 1330 extends from the first port 1311 of the housing 1310, through at least a first portion of the outer channel 1315, through the first inner channel 1358A and the second inner channel 1358B, through at least a second portion of the outer channel 1315, and into the second port 1312. In this manner, the catheter 1330 can be spooled, wound, and/or wrapped around the spool structure 1354 in a similar manner as described above with reference to the catheter 930 and spool structure 954 (e.g., minus the second inner channel 1358B).

As described above with reference to the devices 900, 1000, 1100, and/or 1200, the device 1300 is configured to be transitioned from a first configuration and/or state to a second configuration and/or state in response to rotation of the actuator 1350. For example, in some implementations, a user can rotate the actuator in a counterclockwise direction, which in turn, rotates the first spool structure 1354A in the counterclockwise direction, as indicated by the arrow QQ in FIG. 27. The arrangement of the spool structures 1354A and 1354B and/or the arrangement of the catheter 1330 passing through the inner channels 1358A and 1358B can be such that the counterclockwise rotation of the first spool structure 1354A results in a rotation of the second spool structure 1354B in a clockwise direction, as indicated by the arrow RR in FIG. 27. The catheter 1330 is configured to be in a first position when the device 1300 is in the first configuration and/or state such that a larger or substantially the largest portion or length of the catheter 1330 is disposed within the housing 1310 between the first port 1311 and the second port 1312 (e.g., within one or more lumen or channel defined by the housing 1310 and/or the inner channels 1358A and 1358B). The catheter 1330 is configured to be in a second position when the device 1300 is in the second configuration and/or state such that a smallest or substantially the smallest portion or length of the catheter 1330 is disposed within the housing 1310 between the first port 1311 and the second port 1312. Although not shown, in the embodiment shown in FIG. 27, the device 1300 can be configured such that the catheter 1330 extends along a substantially straight path at least partially defined by the inner channels 1358A and 1358B between the first port 1311 and the second port 1312 when the device 1300 is in the second configuration and/or state. Moreover, as described in detail above, the distal end portion 1332 of the catheter 1330 can be placed in a desired position (e.g., a distal position) relatively to the second port 1312 and/or an access device coupled to the second port 1312 when the catheter 1330 is in the second position. In some implementations, the arrangement and/or configuration of the device 1300 can allow the catheter 1330 to have an increased length relative to, for example, the catheter lengths of at least the devices 900, 1000, and/or 1100.

While the portion of the catheter 1330 is shown in FIG. 27 as being wound, looped, and/or coiled around and/or through the spool structures 1354A and 1354B of the actuator 1350, in other embodiments, a device can include a catheter configured to be at least partially disposed in a housing of the device in any suitable configuration. For example, FIGS. 28-30 illustrate a device 1400 according to another embodiment. The fluid transfer device 1400 (also referred to herein as "device") can be any suitable shape, size, and/or configuration. For example, at least a portion of the device 1400 can be similar to and/or substantially the same as one or more portions (and/or combination of portions) of the devices 100, 200, 300, 400, 500, 600, 700, 800, 900, 1000, 1100, 1200, and/or 1300 described above. Thus, portions of the device 1400 may not be described in further detail herein.

The device 1400 includes at least a housing 1410, a catheter 1430, and an actuator 1450. The housing 1410 can be any suitable configuration. As described above with reference to previous embodiments, the housing 1410 includes a first port 1411 configured to be fixedly coupled to a proximal end portion 1431 of the catheter 1430 and a second port 1412 configured to receive a distal end portion 1432 of the catheter 1430. The housing 1410 can differ, however, by having a cavity structure 1416 and an extension structure 1418. As shown in FIGS. 28-30, the cavity structure 1416 can be disposed at or near a proximal end portion of the housing 1410 and can be coupled to and/or otherwise can include the first port 1411 (e.g., a proximal port). The extension structure 1416 is coupled to the cavity structure 1416 and can be disposed at or near a distal end portion of the housing 1410. The extension structure 1416 can be coupled to and/or can otherwise include the second port 1412 (e.g., a distal port).

As shown in FIGS. 28-30, the cavity structure 1416 can be substantially conical or the like with a base end or surface (e.g., a larger end or surface) forming a proximal surface of the housing 1410 and an apex end (e.g., a smaller end) coupled to the extension structure 1418. Accordingly, in this embodiment, the housing 1410 can have a substantially funnel-like shape. The cavity structure 1416 is configured to hold at least a portion of the catheter 1410. More particularly, prior to placing the catheter 1430 in the second position, the cavity structure 1416 can hold and/or house at least a portion of the catheter 1430 in a spooled, coiled, wound, and/or looped configuration and/or arrangement, as shown in FIGS. 28 and 29. The extension portion 1418 can be configured to hold and/or receive at least the distal end portion 1432 of the catheter 1430 in, for example, a linear, straight, and/or substantially non-coiled configuration and/or arrangement.

The catheter 1430 of the device 1400 can be any suitable shape, size, and/or configuration. For example, in some embodiments, the catheter 1430 can be substantially similar in at least form and/or function to any of the catheters 130, 230, 330, 430, 530, 630, 730, 830, 930, 1030, 1130, 1230, and/or 1330 described above. Thus, such similar portions and/or aspects of the catheter 1430 may not described in further detail herein. For example, in the embodiment shown in FIGS. 28-30, the catheter 1430 can be formed from any suitable material and can have any suitable length, diameter, and/or configuration such as those described above with reference to the catheter 130.

At least a portion of the catheter 1430 is movably disposed within the housing 1410. In some embodiments, the catheter 1430 or a portion thereof can be moved (e.g., via rotational movement of the actuator 1450) between a first position (FIG. 28), in which a portion of the catheter 1430 is spooled and/or wound in the cavity structure 1416 and the distal end portion 1432 of the catheter 1430 is disposed within the extension structure 1418 and/or the second port 1412, and a second position (FIG. 30), in which at least a portion of the catheter 1430 extends through the second port 1412 and at least a portion of an access device coupled to the second port 1412 (not shown). In some embodiments, the catheter 1430 can have a length sufficient to place a distal surface of the catheter 1430 a predetermined, desired, and/or at least a threshold distance beyond a distal surface of the access device when the catheter 1430 is in the second position, as described in detail above.

The actuator 1450 of the device 1400 can be any suitable shape, size, and/or configuration. For example, as shown in FIGS. 28-30, the actuator 1450 includes a first portion 1451 and a second portion 1452. The actuator 1450 can be coupled to the extension structure 1418 of the housing 1410 at or near the second port 1412. In other embodiments, the actuator 1450 can be coupled to the housing 1410 at any suitable position along a length of the housing 1410. The actuator 1450 can be coupled to the housing 1410 in any suitable manner that allows the actuator 1450 to be rotated relative to the housing 1410. Moreover, the actuator 1450 can be coupled to the housing 1410 such that the second portion 1452 is at least partially disposed within the housing 1410 and in contact with and/or otherwise allowed to engage the catheter 1430. In this manner, the actuator 1450 can be substantially similar in at least form and/or function to the actuator 250 described above with reference to FIGS. 3 and 4.

In use, the device 1400 can be in a first configuration and/or state in which the portion of the catheter 1430 (e.g., the proximal end portion 1431) is spooled and/or wound in the cavity structure 1416 and the distal end portion 1432 of the catheter 1430 is disposed within the extension structure 1418 and/or the second port 1412 (FIG. 28) and a user can manipulate the device 1400 by engaging the first portion 1451 of the actuator 1450 to transition the device 1400 to a second configuration and/or state (FIG. 30). For example, the user can exert a force on the first portion 1451 of the actuator 1450 to rotate the actuator 1450 in, for example, a clockwise direction, as indicated by the arrow SS in FIG. 29. As such, the second portion 1452 of the actuator 1450 rotates relative to the housing 1410 and engages the catheter 1430 to move the catheter 1430 in the distal direction from the first position toward the second position, as indicated by the arrow TT in FIG. 29. The movement and/or transitioning of the catheter 1430 from the first position toward the second position is such that the catheter 1430 unspools and/or uncoils within the cavity structure 1416 and allowed to advance (e.g., in a linear direction) through the extension structure 1418. In some instances, the funnel shape of the housing 1410 can be such that the catheter 1430 contacts and/or is otherwise guided or directed by an internal surface of the housing 1410 (e.g., an internal surface of the cavity structure 1416). As shown in FIG. 30, in some instances, the catheter 1430 can be fully extended (e.g., substantially straight or linear) when the catheter 1430 is in the second position. In some implementations, when the second port 1412 of the housing 1410 is coupled to an access device or the like (not shown), the catheter 1430 can be advanced to a desired position relative to the access device, as described in detail above with reference to the device 100.

Figure 31:
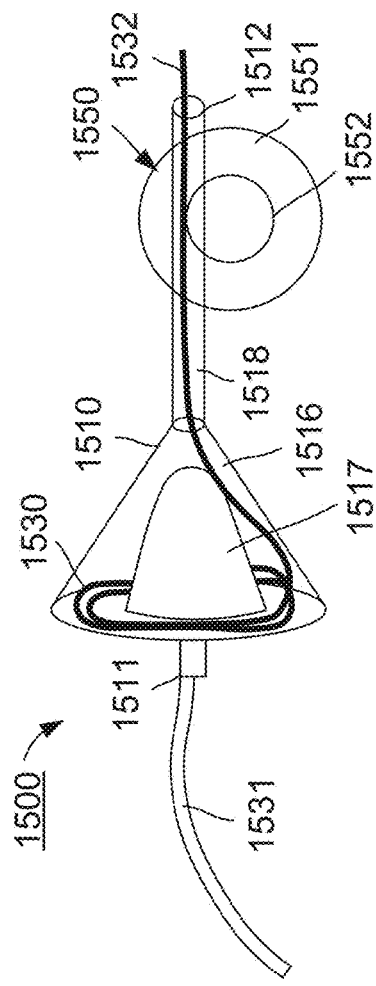
FIGS. 31-33 are schematic illustrations of a fluid transfer device as the fluid transfer device transitions from a first configuration (FIG. 31) to a second configuration (FIG. 33), according to an embodiment.
Figure 32:
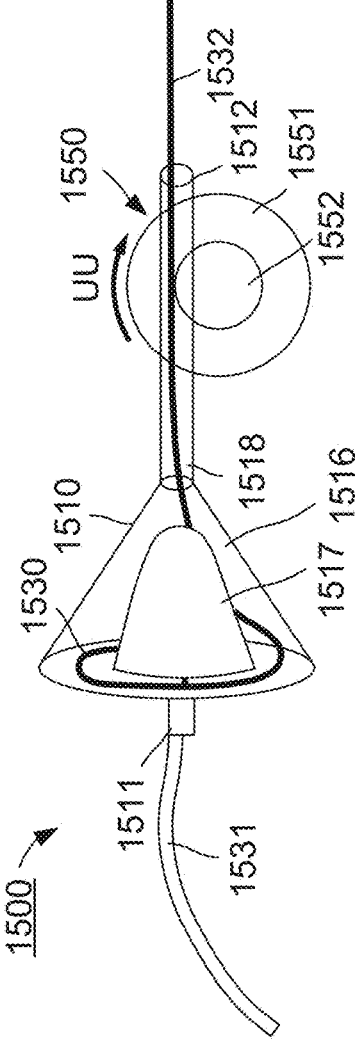
Figure 33:
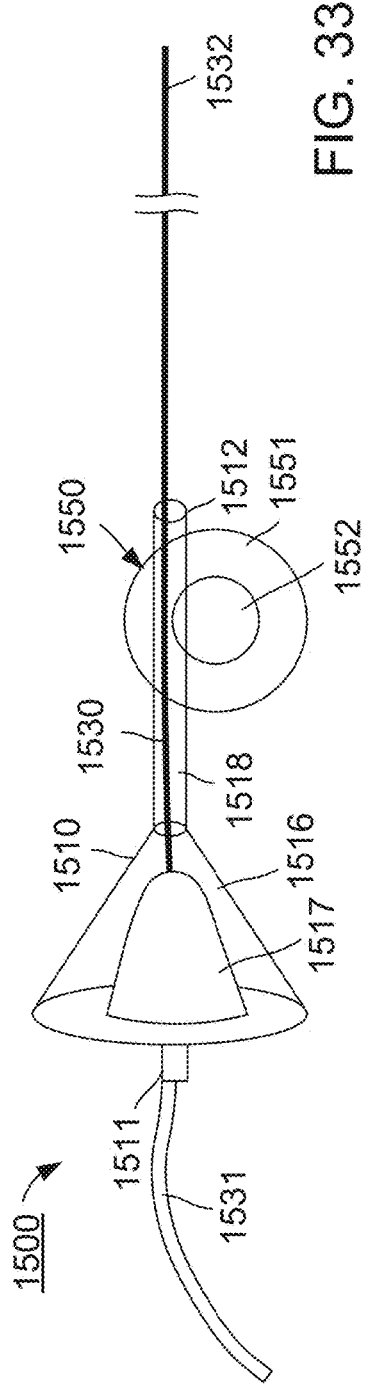

Although not shown in FIGS. 28-30, in some embodiments, the housing 1410 and/or the cavity structure 1416 further include one or more internal structures within the cavity structure 1416 configured to guide and/or direct the spooling (or unspooling), winding (or unwinding), coiling (or uncoiling), etc. of the catheter 1430. For example, FIGS. 31-33 illustrate a fluid transfer device 1500 according to another embodiment. The fluid transfer device 1500 (also referred to herein as "device") can be any suitable shape, size, and/or configuration. For example, at least a portion of the device 1500 can be similar to and/or substantially the same as one or more portions (and/or combination of portions) of the devices 100, 200, 300, 400, 500, 600, 700, 800, 900, 1000, 1100, 1200, 1300, and/or 1400 described above. More particularly, the device 1500 can be substantially similar in at least form and/or function to the device 1400 described above with reference to FIGS. 28-30. Thus, portions of the device 1500 may not be described in further detail herein.

The device 1500 includes at least a housing 1510, a catheter 1530, and an actuator 1550. The housing 1510 can be substantially similar in at least form and/or function to the housing 1410 described above with reference to FIGS. 28-30. For example, the housing 1510 includes a cavity structure 1516 disposed at or near a proximal end portion of the housing 1510 and an extension structure 1518 coupled to the cavity structure 1516 and disposed at or near a distal end portion of the housing 1510. The cavity structure 1516 can be coupled to and/or otherwise can include a first port 1511 (e.g., a proximal port) and the extension structure 1516 can be coupled to and/or otherwise can include the second port 1512 (e.g., a distal port). The first port 1511 is configured to be fixedly coupled to a proximal end portion 1531 of the catheter 1530 and the second port 1512 is configured to receive a distal end portion 1532 of the catheter 1530, as described in detail above with reference to the housing 1410.

The housing 1510 can differ from the housing 1410, however, by including an internal structure 1517 disposed within the cavity structure 1516. As shown, the internal structure 1517 can be, for example, a conical internal structure that is adjacent to and/or extends from a proximal end or surface of the housing 1510. The internal structure 1517 is configured to support and/or guide at least a portion of the catheter 1530 that is disposed within the cavity structure 1516 as the catheter 1530 is moved between a first position (FIG. 31) and a second position (FIG. 33). For example, in some embodiments, the internal structure 1517 and an internal surface of the cavity structure 1516 can collectively define a relatively small space and/or volume that can receive at least a portion of the catheter 1530, as described in further detail herein. Moreover, the internal structure 1516 and/or the internal surface of the cavity structure 1516 can selectively contact, support, and/or guide the catheter 1530 as it is advanced through the housing 1510. In some embodiments, all or nearly all of the catheter 1530 disposed in the housing 1510 can be supported by a portion of the housing 1510 and/or actuator 1550. Although not shown in FIGS. 31-33, the arrangement of the internal structure 1517 can include an opening, coupler, and/or any other suitable feature configured to allow the first port 1511 to be fixedly coupled to the proximal end portion 1531 of the catheter 1530.

The catheter 1530 of the device 1500 can be any suitable shape, size, and/or configuration. For example, in some embodiments, the catheter 1530 can be substantially similar in at least form and/or function to any of the catheters 130, 230, 330, 430, 530, 630, 730, 830, 930, 1030, 1130, 1230, 1330, and/or 1430 described above. Thus, such similar portions and/or aspects of the catheter 1530 may not described in further detail herein. For example, in the embodiment shown in FIGS. 31-33, the catheter 1530 can be formed from any suitable material and can have any suitable length, diameter, and/or configuration such as those described above with reference to the catheter 130.

At least a portion of the catheter 1530 is movably disposed within the housing 1510. In some embodiments, the catheter 1530 or a portion thereof can be moved (e.g., via rotational movement of the actuator 1550) between a first position and a second position. For example, as shown in FIG. 31, when the catheter 1530 is in the first position, a portion of the catheter 1530 is spooled and/or wound about the internal structure 1517 within the cavity structure 1516 and the distal end portion 1532 of the catheter 1530 is disposed within the extension structure 1518 and/or the second port 1512. As shown in FIG. 33, when the catheter 1530 is in the second position, at least a portion of the catheter 1530 extends through the second port 1512 and at least a portion of an access device coupled to the second port 1512 (not shown). In some embodiments, the catheter 1530 can have a length sufficient to place a distal surface of the catheter 1530 a predetermined, desired, and/or at least a threshold distance beyond a distal surface of the access device when the catheter 1530 is in the second position, as described in detail above.

The actuator 1550 of the device 1500 can be any suitable shape, size, and/or configuration. For example, as shown in FIGS. 31-33, the actuator 1550 includes a first portion 1551 and a second portion 1552. The actuator 1550 can be coupled to the extension structure 1518 of the housing 1510 at or near the second port 1512. In other embodiments, the actuator 1550 can be coupled to the housing 1510 at any suitable position along a length of the housing 1510. The actuator 1550 can be coupled to the housing 1510 in any suitable manner that allows the actuator 1550 to be rotated relative to the housing 1510. Moreover, the actuator 1550 can be coupled to the housing 1510 such that the second portion 1552 is at least partially disposed within the housing 1510 and in contact with and/or otherwise allowed to engage the catheter 1530. In this manner, the actuator 1550 can be substantially similar in at least form and/or function to the actuator 250 described above with reference to FIGS. 3 and 4.

In use, the device 1500 can be in a first configuration and/or state in which the portion of the catheter 1530 (e.g., the proximal end portion 1531) is spooled and/or wound about the internal structure 1517 within the cavity structure 1516 and the distal end portion 1532 of the catheter 1530 is disposed within the extension structure 1518 and/or the second port 1512 (FIG. 31) and a user can manipulate the device 1500 by engaging the first portion 1551 of the actuator 1550 to transition the device 1500 to or toward a second configuration and/or state (FIG. 33). For example, the user can exert a force on the first portion 1551 of the actuator 1550 to rotate the actuator 1550 in, for example, a clockwise direction, as indicated by the arrow UU in FIG. 32. As such, the second portion 1552 of the actuator 1550 rotates relative to the housing 1510 and engages the catheter 1530 to move the catheter 1530 in the distal direction from the first position toward the second position. The movement and/or transitioning of the catheter 1530 is such that the catheter 1530 unspools and/or uncoils within the cavity structure 1516 and is allowed to advance (e.g., in a linear direction) through the extension structure 1518. In some instances, the conical shape of the internal structure 1517 and the conical shape of the interior surface of the cavity structure 1516 can be such that the catheter 1530 contacts and/or is otherwise guided or directed as the catheter 1530 is moved from the first position toward the second position. As shown in FIG. 33, in some instances, the catheter 1530 can be fully extended (e.g., substantially straight or linear) when the catheter 1530 is in the second position. In some implementations, when the second port 1512 of the housing 1510 is coupled to an access device or the like (not shown), the catheter 1530 can be advanced to a desired position relative to the access device, as described in detail above with reference to the device 150.

FIGS. 34-39 illustrate a fluid transfer device 1600 according to another embodiment. The fluid transfer device 1600 (also referred to herein as "device") can be any suitable shape, size, and/or configuration. For example, at least a portion of the device 1600 can be similar to and/or substantially the same as one or more portions (and/or combination of portions) of the devices 100, 200, 300, 400, 500, 600, 700, 800, 900, 1000, 1100, 1200, 1300, 1400, and/or 1500 described above. More specifically, the device 1600 can be substantially similar in at least form and/or function to the devices 900, 1000, and/or 1100 (or any suitable combinations thereof) described in detail above. Thus, portions of the device 1600 may not be described in further detail herein.

The device 1600 includes at least a housing 1610, a catheter 1630, and an actuator 1650. The housing 1610 can be substantially similar to the housing 910, 1010, and 1110, described in detail above. For example, the housing 1610 includes a first port 1611 that can be configured to be coupled to and/or to otherwise receive a proximal end portion 1631 of the catheter 1630 and a second port 1612 configured to receive a distal end portion 1632 of the catheter 1630. In some embodiments, the first port 1611 can be configured to fixedly couple to the proximal end portion 1631 of the catheter 1630, as described above with reference to the devices 700, 800, 900, 1000, and 1100. The housing 1610 can be any suitable shape, size, or configuration. In some embodiments, the housing 1610 or portions thereof can have a circular cross-sectional shape defined with respect to a top view plane. In some embodiments, each of the first port 1611 and the second port 1612 can extend from a circumferential edge or surface of the housing 1610 (e.g., the circumferential surface along the perimeter of the housing), as shown for example in FIGS. 34-36 and. The first port 1611 and the second port 1612 can be positioned along the circumferential edge of the housing such that an axis defined by a lumen of the first port 1611 is substantially parallel to an axis defined by a lumen of the second port 1612. In some embodiments, the first port 1611 of the housing 1610 can be enclosed by a cover 1619 configured to receive at least a portion of the catheter 1630 to protect the at least the portion of the catheter 1630 from undesirable bending, flexing, and/or kinking. In some embodiments, the cover 1619 includes and/or forms a stopper 1620 configured to limit, restrict, and/or otherwise at least partially define a range of motion associated with the movement of the actuator 1650 (e.g., a rotational range of motion).

The catheter 1630 of the device 1600 can be any suitable shape, size, and/or configuration. For example, in some embodiments, the catheter 1630 can be substantially similar in at least form and/or function to any of the catheters 130, 230, 330, 430, 530, 630, 730, 830, 930, 1030, 1130, 1230, 1330, 1430, and/or 1530 described above. Thus, such similar portions and/or aspects of the catheter 1630 may not be described in further detail herein. For example, in some embodiments, the catheter 1630 can be formed of a single material and can have a predetermined length, diameter(s), and/or configuration such as those described above with reference to the catheter 130.

In other embodiments, the catheter 1630 can be formed of different materials and/or can have different size, shape, diameter, thickness, etc. to result in any suitable stiffness, flexibility, hardness, and/or durometer. For example, the proximal end portion 1631 of the catheter 1630 can be formed from a flexible material which can deform in response to a bending force or a sudden change in pressure. In some instances, the proximal end portion 1631 of the catheter 1630 can deform in response to a negative pressure having a magnitude that exceeds a threshold amount or magnitude of negative pressure, which in turn, can reduce the likelihood of collapsing a portion of the catheter 1630 at a location downstream of the proximal end portion 1631

(e.g., the distal end portion 1632 and/or any other suitable portion). The distal end portion 1632 of the catheter 1630 can be formed from a relatively rigid material or a material having a stiffness or rigidity that is at least greater than the stiffness or rigidity of the proximal end portion 1631 of the catheter 1630. In some embodiments, the distal end portion 1632 can have a diameter smaller than a diameter of the proximal end portion 1631 to facilitate advancing at least a portion of the catheter 1630 to and/or from a desired position relative to a PIV. In some embodiments, the proximal end portion 1631 and the distal end portion 1632 of the catheter 1630 can be separate components having different length, length, diameter and/or configuration, which can be mechanically and fluidically connected at or within, for example, the first port 1611, the cover 1619, and/or any other suitable portion of the housing 1610. For example, in some embodiments, a secondary catheter or an external catheter can be disposed outside of the housing 1610 and can include a distal end portion that is at least partially disposed in the first port 1611 and/or the cover 1619 and coupled to the proximal end portion of the catheter 1630 using any suitable coupler, adapter, connector, and/or the like.

Figure 34:
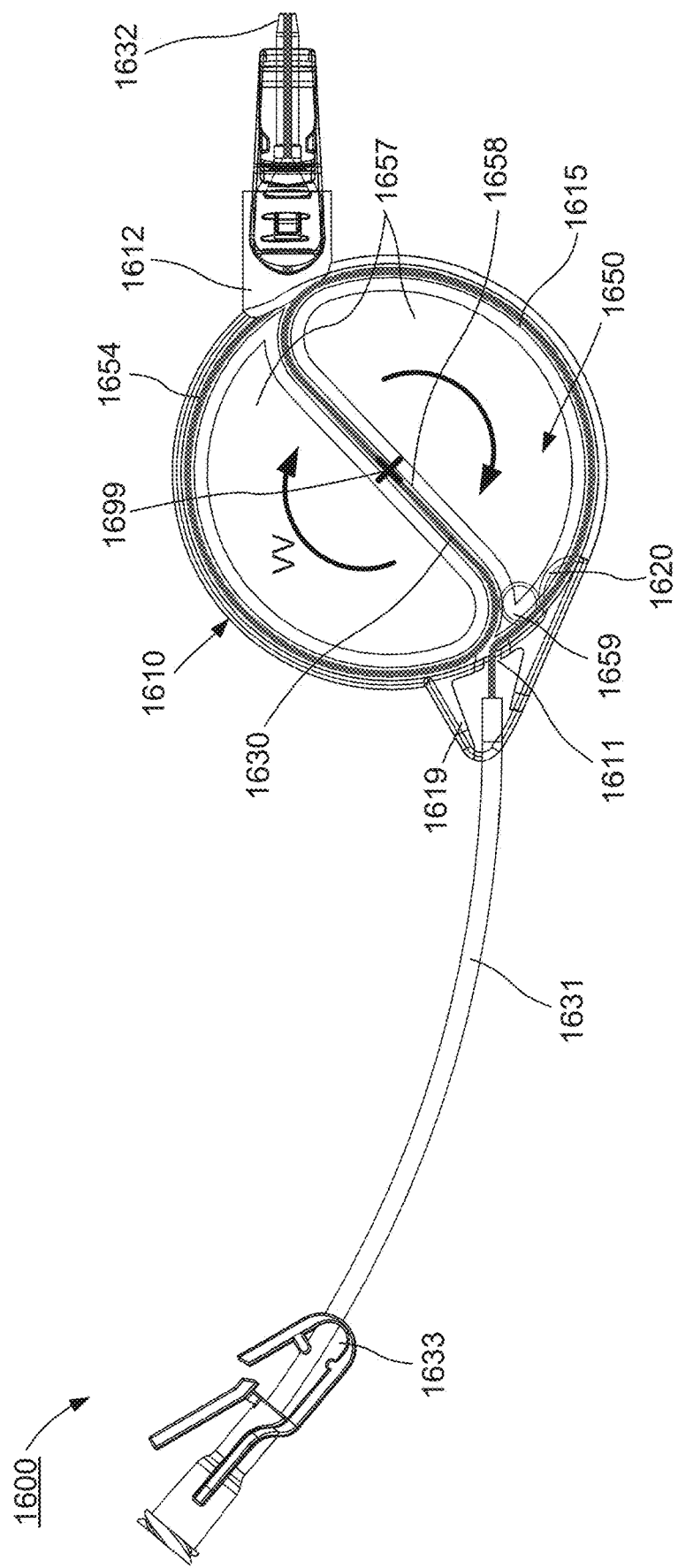
FIGS. 34 and 35 are top view illustrations of a fluid transfer device in a first configuration and a second configuration, respectively, according to an embodiment.
Figure 35:
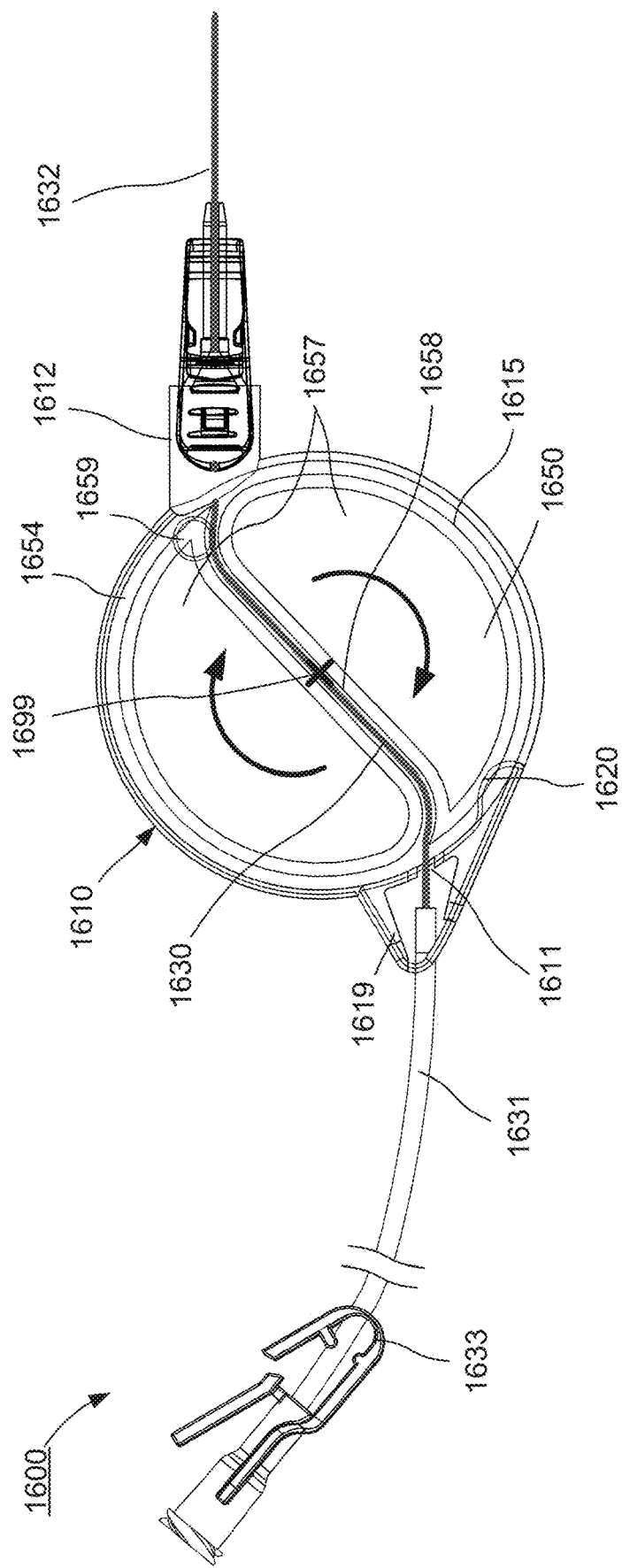
Figure 36:
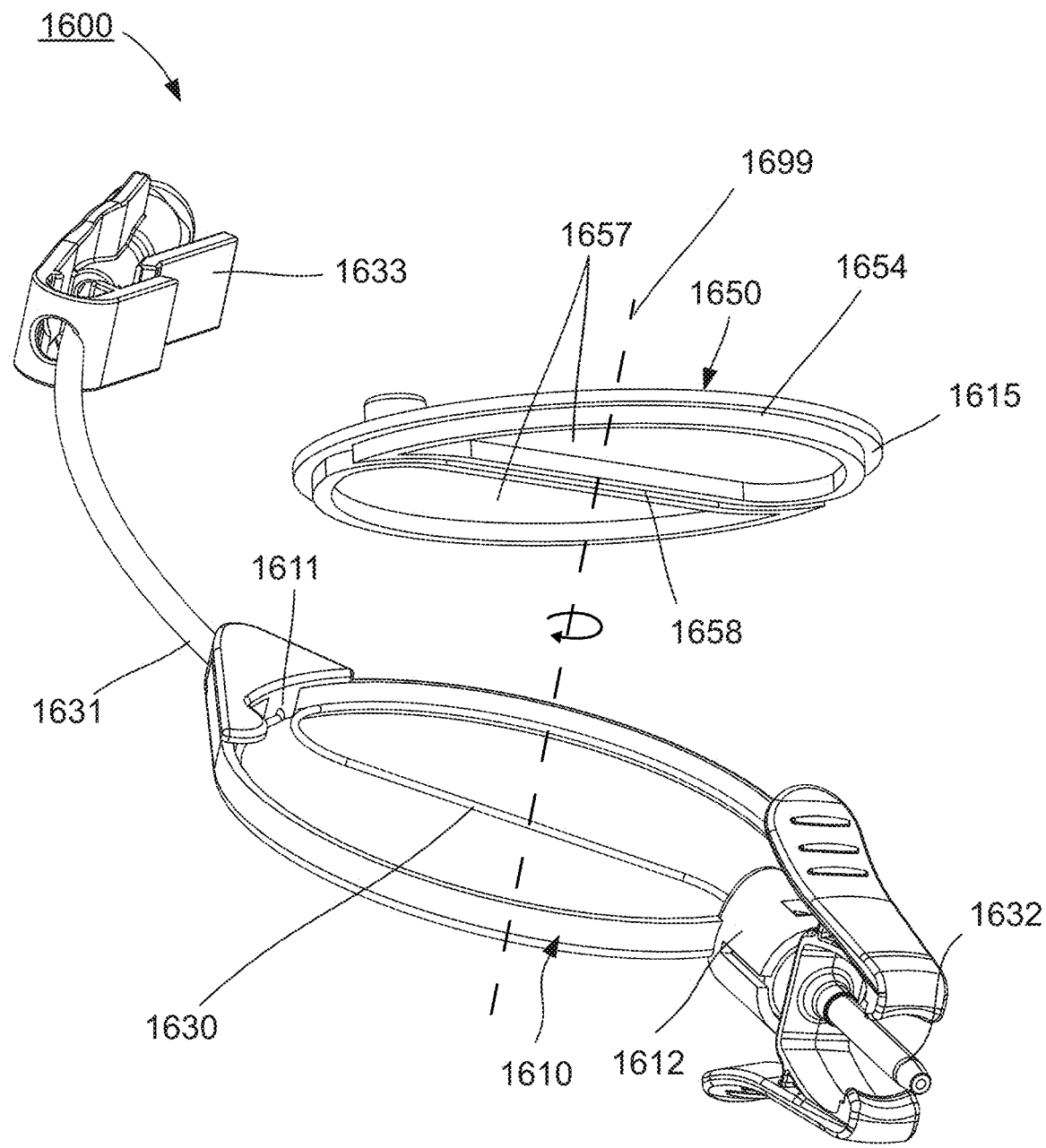
FIG. 36 is a partially exploded perspective illustration of the fluid transfer device of FIG. 34.

As described with reference to the device 100, in some instances, the proximal end portion 1631 of the catheter 1630 can include a clamp 1633, which can be configured to physically and/or fluidically couple to a fluid source and/or fluid reservoir (e.g., a sample bottle). As such, a volume of fluid (e.g., bodily fluid, medicament, saline, etc.) can be transferred between the catheter 1630 (and, in turn, a patient) and a fluid source or fluid reservoir via the coupler 1633. In some embodiments, the coupler 1633 can be a clamp, grommet, o-ring, compression member, Luer Lok™, and/or any other suitable coupler. For example, FIGS. 34-36 show the connector 1633 can be a female Luer Lok™ with an integrated clamp.

Figure 37:
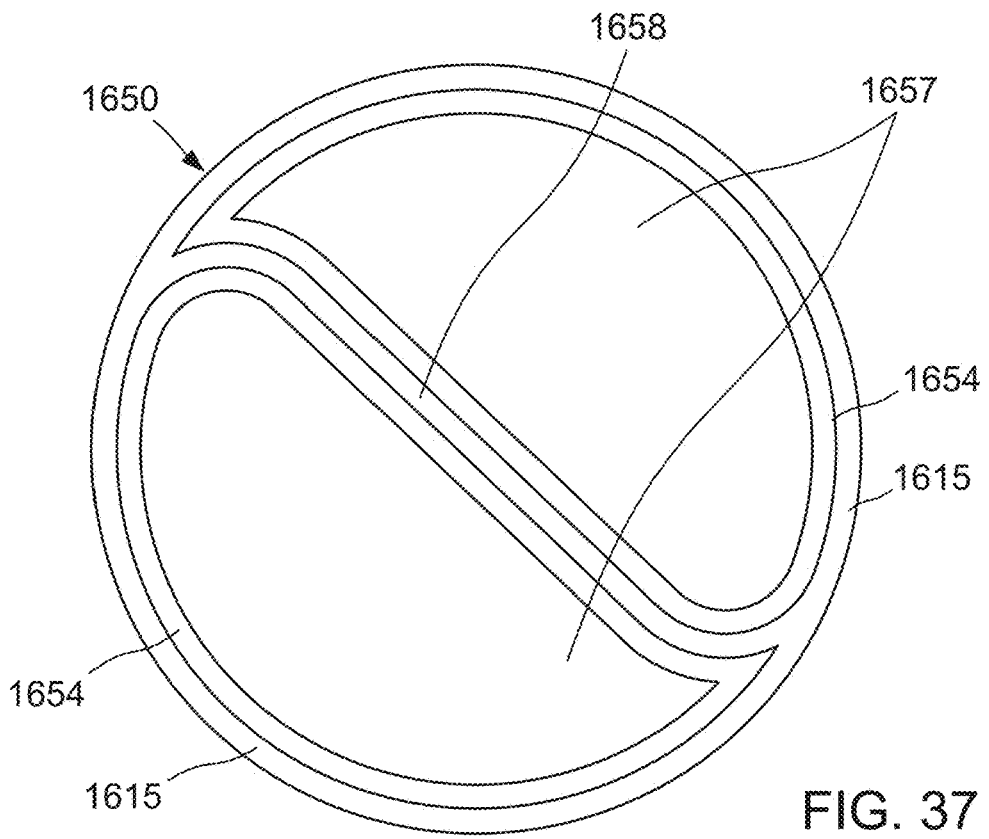
FIGS. 37 and 38 are a bottom view and a top view, respectively, of the actuator 1650 of the fluid transfer device of FIG. 34.
Figure 38:
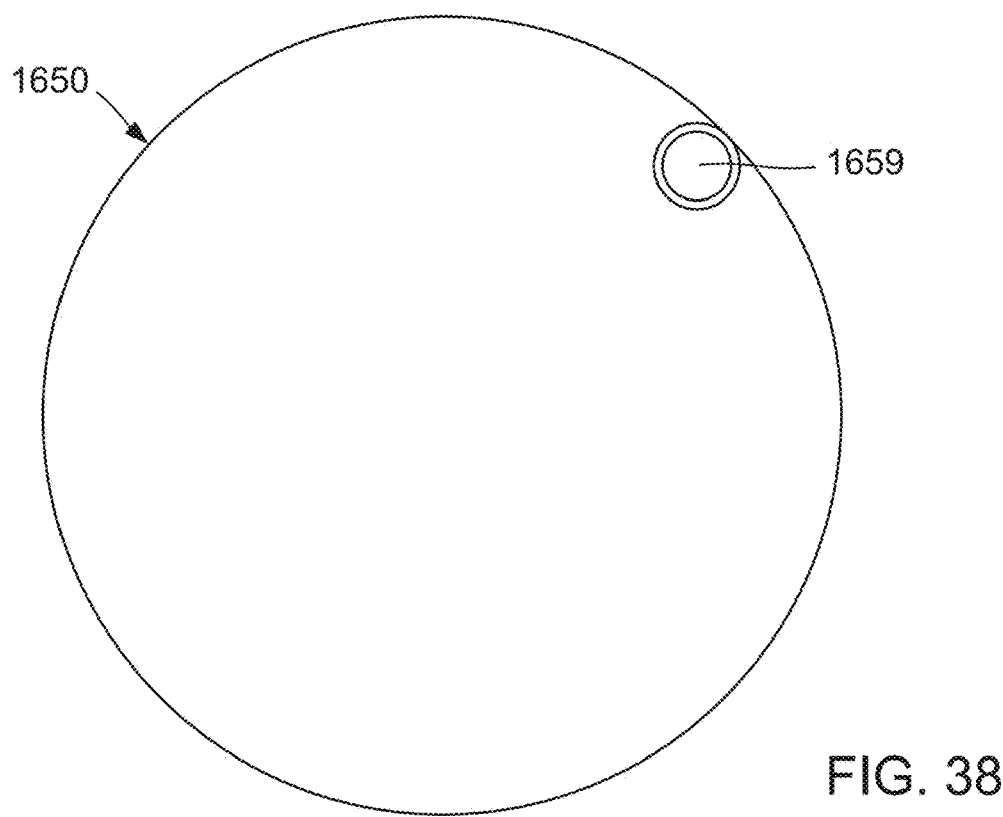

The actuator 1650 of the device 1600 can be any suitable shape, size, and/or configuration. In some embodiments, the actuator 1650 can be substantially similar to the actuators 950 and/or 1050 described in detail above. For example, as shown in FIGS. 34-37, the actuator 1650 is at least partially disposed within the housing 1610 and has a spool structure 1654 that is movably coupled to the housing 1610. As shown in FIGS. 34, 36 and 37, the spool structure 1654 includes a pair of engagement structures 1657 that are disposed in a mirrored orientation relative to each other and that define (1) an inner channel or path 1658 between interior, inner, and/or adjacent portions thereof, and (2) an outer channel 1615 defined between the exterior or outer portion and/or surface of the spool structure 1654 and an interior or inner portion and/or surface of the housing 1610 (e.g., an inner perimeter).

As shown, the actuator 1650 includes an engagement feature 1659 disposed on the outside of the actuator 1650 (e.g., outside of the housing 1610). In some implementations, a user can engage, contact, and/or exert a force on the engagement feature 1659 to move the actuator 1650 relative to the housing 1610 (e.g., in a rotational motion about the axis 1699 shown in FIGS. 34 and 35). As described above with reference to the devices 900, 1000, and/or 1100, the movement of the actuator 1650 results in and/or otherwise causes at least a portion of the catheter 1630 that is wound or coiled inside the housing 1610 to be advanced through one or more portions of the housing 1610. Moreover, as shown, the engagement feature 1659 is disposed at or near a circumference or edge of the actuator 1650. To prevent extending the winding (or unwinding) of the catheter 1630 beyond predetermined positions, the cover 1619 can include a stopper feature 1620 positioned in the path of the engaging feature 1659 along the circumference of the actuator 1650 (or housing 1610), thereby restricting or at least partially defining the movement of the engagement feature 1659, and thus the actuator 1650, relative to the housing 1610.

Figure 39:
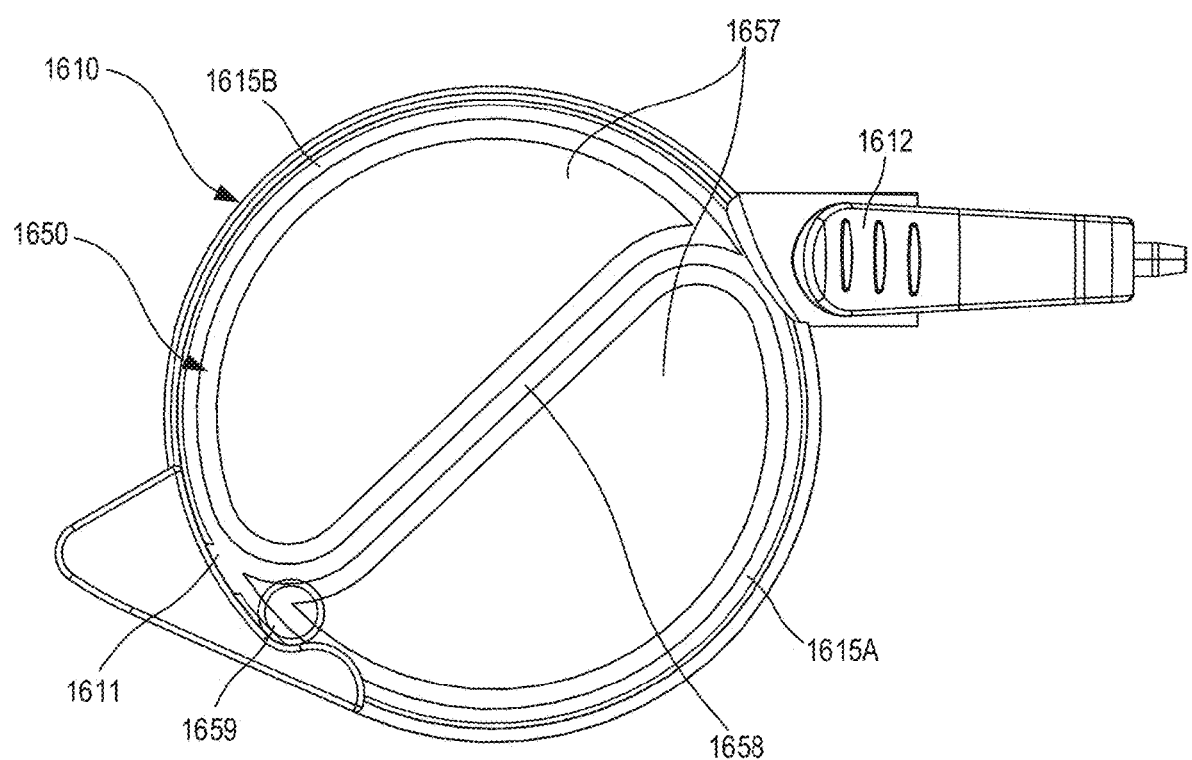
FIG. 39 is a top view of the housing 1610 of the fluid transfer device of FIG. 34.

The catheter 1630 is disposed within the housing 1610 such that a portion of the catheter 1630 is disposed within at least one of the outer channel 1615 and/or the inner channel 1658 and is configured to be advanced therethrough (e.g., through the housing 1610) in response to actuation of the actuator 1650. For example, FIGS. 34, 36 and 39 illustrate the device 1600 in a first configuration and/or state in which the catheter 1630 is in a first position. When the catheter 1630 is in the first position, a portion of the catheter 1630 can extend from the first port 1611, through a first portion 1615A of the outer channel 1615, through the inner channel 1658, through a second portion 1615B of the outer channel 1615 and into the second port 1612. As shown in FIG. 39, when the device 1600 is in the first configuration and/or state, the catheter 1630 can pass through the first portion 1615A of the outer channel 1615 to a position near the second port 1612. Rather than extending from the first portion 1615A of the outer channel 1615 into the second port 1612, the catheter 1630 extends through the inner channel 1658 from a position near the second port 1612 to a position near the first port 1611. As such, the catheter 1630 substantially wraps around one of the engagement structures 1657. From the position at or near the first port 1611, the catheter 1630 further extends through the second portion 1615B of the outer channel 1615 (e.g., defined at least in part by the other engagement structure 1657) and to a position at, near, or at least partially within the second port 1612. In this position and/or orientation, the path along the outer channel 1615 and the inner channel 1658 through which the catheter 1630 extends between the first port 1611 and the second port 1612 is, for example, the longest or substantially the longest path between the first port 1611 and the second port 1612 of the housing 1610, and the largest or substantially the largest portion of the catheter 1630 is disposed within the housing 1610 when the device 1600 is in the first configuration and/or state (e.g., when the actuator 1650 and/or catheter 1630 is/are in the first position).

The device 1600 can be transitioned from the first configuration and/or state to a second configuration and/or state by manipulating the engaging feature 1659 of the actuator 1650 to move or rotate the actuator 1650 about a central axis 1699 defined by the housing 1610 in a clockwise direction, as indicated by the arrow(s) VV in FIG. 34. The movement of the actuator 1650 results in a rotation of the spool structure 1654 and the engagement structures 1657, which in turn, change a portion of the outer channel 1615 that is disposed between the first port 1611 and a first end portion of the inner channel 1658 (at or near the second port 1612), and a portion of the outer channel 1615 that is disposed between the second port 1612 and a second end portion of the inner channel 1658 opposite the first end portion (at or near the first port 1611), as shown in FIG. 35. More specifically, the portions of the outer channel 1615 are reduced, which in turn, is operable to advance the catheter 1630 through a serpentine, circuitous, tortuous, and/or otherwise curved or non-linear path collectively formed and/or defined by the outer channel 1615 and the inner channel 1658 from its first position toward its second position. Said another way, rotation of the actuator 1650 relative to the housing 1610 results in a rotation of the engagement structures 1657 relative to the first port 1611 and the second port 1612. Moreover, the rotation of the engagement structures 1657 moves and/or changes an orientation of the inner channel 1658 relative to the first port 1611 and the second port 1612.

The engaging feature 1659 can be manipulated to move the actuator 1650 a predetermined and/or desired amount to place the device 1600 in the second configuration and/or state in which the catheter 1630 is in the second position. In some implementations, the actuator 1650 can be rotated approximately 180° to transition the device 1600 from the first configuration to the second configuration. In this position and/or orientation, the outer channel 1615 and the inner channel 1658 can define, for example, the shortest path through the housing 1610 between the first port 1611 and the second port 1612. For example, in some implementations, the arrangement of the engagement structures 1657 is such that when the device 1600 is in the second configuration and/or state, the catheter 1630 can extend between the first port 1611 and the second port 1612 via the inner channel 1658 and without substantially extending through the outer channel 1615 (e.g., neither the first portion nor the second portion of the outer channel 1615).

As described in detail above with reference to previous embodiments, the arrangement of the device 1600 can allow the catheter 1630 to have a length or "reach" that can be longer than, for example, the housing 1610 and/or a length of the housing 1610 between the first port 1611 and the second port 1612 (e.g., via the inner channel 1658). Thus, when the second port 1612 of the housing 1610 is coupled to an access device or the like (not shown), the catheter 1630 can be advanced to a desired position relative to the access device without the device 1600 having an undue length regardless of a type and/or length of the access device, as described in detail above with reference to the device 100.

The arrangement of the device 1600 is such that manipulating the engaging feature 1659 to move or rotate the actuator 1650 an angular amount or distance (e.g., an amount of rotation) results in the distal end portion 1632 of the catheter 1630 being moved a linear amount or distance. In other words, linear displacement (e.g., translation) of the distal end portion 1632 of the catheter 1630 is achieved with an angular displacement (e.g., rotation) of the actuator 1650. In some implementations, the actuator 1650, the spool structure 1654, and/or the engagement structures 1659, are configured to achieve a "length multiplying" and/or "displacement multiplying" effect and/or otherwise configured to provide a mechanical advantage such that a relatively small amount of rotation of the engagement feature 1659 of the actuator 1650 results in a relatively large amount of translation of the distal end portion 1632 of the catheter 1630 (or at least an amount of translation that is greater than the amount of rotation).

As described above, the movement of the actuator 1650 causes the distal end portion 1632 of the catheter 1630 to be moved an amount or distance in a linear direction. Such movement of the actuator exerts a force on the portions of the catheter 1630 that are wound or coiled inside the housing 1610. The arrangement of the device 1600 is such that the all or substantially all the portions of the catheter 1630 disposed within the housing 1610 are supported by the a surface of the housing 1610 and/or actuator 1650 that defines the outer channel 1615 and/or the inner channel 1658, which can, for example, provide tangential support along the portions of the catheter 1630 disposed within the housing 1610 when the actuator 1650 exerts the force operable to move the catheter 1630 through the housing 1610. As a result, the catheter 1630 can be advanced avoiding undesired bending, kinking, or deformation that may otherwise be associated with "pushing" or advancing an unsupported length of a catheter (or other relatively flexible tube, member, etc.).

In some embodiments, the supported path or trajectory that the portions of the catheter 1630 disposed inside the housing 1610 (e.g., that are wound or coiled inside the housing 1610) can be advanced along in response to movement of the actuator 1650 is defined by the inner surfaces of the engagement structures 1657 defining the inner channel 1615 and/or the outer surfaces of the engagement structures 1657 and the corresponding inner surface of the housing 1610 that define the outer channel 1658. In this way, when the actuator 1650 is moved, the portions of the catheter 1630 disposed inside the housing 1610 are supported, guided, directed, and/or otherwise allowed to move along this supported path of trajectory, which in turn, limits and/or substantially prevents undesired deformation, coiling, bending, bowing, and/or deflection of or more portions of the catheter 1630 inside the housing 1650 that may limit and/or substantially prevent a desired linear displacement of the distal end portion 1632 of the catheter 1630.

While the actuator 1650 has been described as moving and/or being moved in a clockwise direction to transition the device 1600 from the first configuration and/or state to the second configuration and/or state, as indicated by the arrow VV in FIG. 34, the actuator 1650 can alternatively be configured to move in a counterclockwise direction to transition the device 1600 from the first configuration and/or state to the second configuration. For example, the arrangement of the spool structure 1654 and/or the arrangement of the catheter 1630 passing through the inner channel 1658 can be inverted with respect to the in-plane axis of the device 1600 such that counterclockwise movement of the actuator 1650 changes a portion of the outer channel 1615 that is disposed between the first port 1611 and a first end portion of the inner channel 1658, and a portion of the outer channel 1615 that is disposed between the second port 1612 and a second end portion of the inner channel 1658 opposite the first end portion.

In some instances, the user can rotate the actuator 1650 in a first direction to transition the device from the first configuration to the second configuration, and thus advance the catheter 1630 from the first position to the second position, as described in detail above. In some instances, the user can then, after the device has been transitioned from the first configuration to the second configuration, rotate the actuator 1650 in a second direction opposite to the first direction, to retract the catheter 1630 from the second position back to the first position, or to a position such that a large portion or length of the catheter 1630 is disposed within the housing 1610 between the first port 1611 and the second port 1612. Alternatively, in some instances, the user can first rotate the actuator 1650 to transition the device from the first configuration to the second configuration, and thus advance the catheter 1630 from the first position to the second position, and then continue to rotate the actuator 1650 in the same direction to retract the catheter 1630 from the second position to a third position in which a portion or length of the catheter 1630 is disposed within the housing 1610 between the first port 1611 and the second port 1612 (e.g., the catheter 1630 is looped around the actuator 1650 in an opposite direction). For example, in some implementations, the actuator 1650 can be rotated about 180° to move the catheter 1630 from the first position to the second position, and then can be rotated beyond 180° (e.g., until the engagement feature 1659 hits the stop 1620) to move the catheter from the second position to the third position.

Referring now to FIG. 40, a flowchart is presented illustrating a method 10 of using a fluid transfer to transfer fluid to or from a patient through an indwelling vascular access device according to an embodiment. The fluid transfer device can be similar to and/or substantially the same as any of the fluid transfer devices 100, 200, 300, 500, 600, 700, 800, 900, 1000, 1100, 1200, 1300, 1400, 1500, and/or 1600 described in detail above. Accordingly, the fluid transfer device (also referred to herein as "device") can include a housing, a catheter at least partially disposed in the housing, and an actuator coupled to the housing and selectively engaging the catheter. The housing includes a first port and a second port. The first port can be fixedly coupled to a proximal end portion of the catheter. The method 10 includes coupling the second port of the housing to an indwelling vascular access device, at 11. For example, in some embodiments, a user can manipulate the fluid transfer device to physically and fluidically couple the second port of the housing of the fluid transfer device to an indwelling vascular access device such as an indwelling peripheral intravenous line (IV), and extended-dwell PIV, a midline PIV, a PICC line and/or the like. The arrangement of the catheter of the fluid transfer device can be such that the proximal end portion of the catheter is fixedly coupled to and/or otherwise maintained in a fixed position relative to the first port. In some embodiments, the second port of the housing can be and/or can include a Luer Lok™, a "Clip-Lock-Snap" connection, and/or the like configured to physically and fluidically couple to, for example, the PIV.

The actuator of the fluid transfer device is rotated an angular distance about a central axis defined by the housing of the fluid transfer device, at 12. For example, in some embodiments the housing can define a range of motion of the actuator. The housing can include a structure, feature, component, and/or the like that can selectively engage a portion of the actuator to limit, restrict, guide, and/or otherwise direct an amount or direction of movement of a portion of the actuator. Thus, the actuator can be rotated through a desired range of motion and/or through a desired angular displacement based at least in part on a size and/or arrangement of a portion of the actuator, a size and/or arrangement of a portion of the housing, and/or the like—similar to the actuators described in detail with reference to the device 900, 1000, 1100 and 1600.

A distal end portion of the catheter is advanced, in response to the rotation of the actuator, a linear distance from a first position to a second position, at 13. In the first position, the distal end portion of the catheter is in the housing, and in the second position, the distal end portion of the catheter is distal to the indwelling vascular access device. The distal end portion of the catheter is advanced linearly in a direction orthogonal to the central axis through the second port and the indwelling access device. In some embodiments, the rotation of the actuator through a rotational and/or angular displacement can advance, coil (or uncoil), spool (or unspool), and/or otherwise move the distal end portion of the catheter disposed within the housing. For example, the rotation of the actuator relative to the housing and the advancement of the catheter (or at least the distal end portion thereof) can be substantially similar to the rotation, advancement, etc., described in detail above with reference to the device 1600. In this manner the arrangement of the fluid transfer device can be such that the catheter has a length sufficient to extend a desired distance (e.g., at least partially into or through a standard or short PIV, an extended-dwell PIV, a midline PIV, a PICC line, and/or any other suitable access device). Similarly, the catheter can have a length that is sufficient to allow the second port of the housing to be coupled to any suitable adapter, extension set, tube, port, etc. In some instances, for example, the catheter can have a length that is sufficient to extend from the housing, through an IV extension set and/or any suitable length of tubing coupled thereto, through a port of an PIV (e.g., a proximal port and/or a side port), and to a position within a vein of a patient distal to the PIV.

While the devices 100, 200, 300, 400, 500, 700, 800, 900, 1000, 1100, 1200, 1300, 1400, and 1500 have been shown and/or described above as being coupled to an access device such as a PIV, in other embodiments, the devices can be coupled to any suitable access device, introducer, adapter, secondary or intermediate device, etc. For example, in some instances, the second port 212 of the housing 210 of the device 200 can be coupled to and extension set or the like, which in turn, is coupled to an indwelling PIV such as those described herein. The extension set can be, for example, a dual port IV extension set such as a "Y-adapter" or "T-adapter." In this manner, the terms "Y-adapter" and "T-adapter" generally describe an overall shape of the dual port IV extension set. In other embodiments, an extension set can be a single port IV extension set. In these embodiments, the devices described herein can include a catheter having a length sufficient to extend from the housing of the device, through the extension set or other intermediate device, and through the access device to position a distal end of the catheter distal to the access device. Moreover, the access device can be any suitable device having any suitable length such as, for example, a standard or short PIV, an extended-dwell PIV, a midline PIV, a PICC line, and/or any other device. In other embodiments, any of the devices described herein can be coupled to any suitable access device or the like and can be used for any suitable procedure, surgery, etc.

In some instances, the transfer devices described herein can be assembled during one or more manufacturing processes and packaged in a pre-assembled configuration. For example, in some instances, the assembly of the devices can be performed in a substantially sterile environment such as, for example, an ethylene oxide environment, or the like. In other embodiments, the transfer devices described herein can be packaged in a non-assembled configuration (e.g., a user can open the package and assemble the components to form the device). The components of the devices can be packaged together or separately. In some embodiments, the devices can be packaged with, for example, a PIV, an extension set, a Y-adapter or T-adapter, and/or any other suitable component.

Any of the devices described herein can be used in any suitable process, procedure, method, and/or the like. For example, in some instances, the devices described herein can be used in a medical procedure, process, and/or method for transferring fluid to or from a patient. Some such procedures can include, for example, aspirating a volume of bodily fluid from a patient via a previously placed or indwelling access device. More particularly, any of the devices described herein can be used to aspirate a volume of blood from a patient via a previously placed or indwelling peripheral intravenous line.

While various embodiments have been described above, it should be understood that they have been presented by way of example only, and not limitation. While the embodiments have been particularly shown and described, it will be understood that various changes in form and details may be made. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above. For example, as described above, the device 400 can be a combination of certain features and/or aspects of the devices 200 and 300.

Although not shown in some of the devices described herein, any of the housings and/or actuators can include one or more internal supports or the like configured to support the catheter within the housing. Such internal supports can be, for example, guides, tracks, rails, springs, sleeves, protrusions, ribs, channels, sponges, pads, etc. configured to selectively engage a portion of the catheter. In this manner, the internal supports can limit and/or substantially prevent undesired deformation and/or deflection of a portion of the catheter as the device is transitioned between the first configuration and the second configuration.

While described as limiting and/or substantially preventing undesired deformation and/or deflection of the catheter, in other embodiments, the catheter can be configured to deflect, bow, bend, and/or reconfigure without kinking and/or permanently deforming. For example, in some instances, a distal end surface of the catheter may impact an obstruction or the like while being advanced from the first position to the second position, which can at least temporarily obstruct and/or prevent further movement of the distal end portion of the catheter. In such instances, if a user continues to exert a force on the actuator otherwise operable to move the catheter toward the second position, an unsupported portion of the catheter within the housing can bend, flex, bow, deflect, and/or otherwise be transitioned from an "unclutched" configuration to a "clutched" configuration. In other words, a portion of the force exerted on the actuator and otherwise operable to advance the catheter toward the second position is operable to deflect, bend, flex, bow, etc. a portion of the catheter within the housing. As such, a force transmitted to and/or through the distal surface of the catheter (e.g., on the obstruction) is reduced, which in turn, can reduce damage to the catheter, an access device through which the catheter is being advanced (e.g., a PIV), a venous structure (e.g., vein wall), and/or the like.

In some embodiments, increasing or decreasing a durometer of the catheter, a length of the catheter, a length of the housing, and/or an amount of support provided, for example, by an internal support member (e.g., a guide, track, rail, spring, pad, post, etc.) can allow for a tuning or adjustment of the amount of deflection (e.g., "clutching") of the catheter and/or an amount of force transferred through the catheter. In some embodiments, a portion of the catheter can impact and/or contact an inner surface of the housing (e.g., a sidewall) when bowed, flexed, deflected, and/or clutched. In some embodiments, this arrangement can produce a visual, audible, and/or haptic indication that the distal end surface of the catheter has impacted an obstruction. In some embodiments, an internal support member (as described above) such as a pad or the like can be used to "tune" and/or alter for example, an audible and/or haptic output or indication that the distal end surface of the catheter has impacted an obstruction.

Although not described above with reference to specific embodiments, it should be understood that any of the embodiments described herein can be manipulated to retract a catheter from its second position to its first position. For example, in some instances, after withdrawing a desired volume of bodily fluid through a catheter of a device, user can manipulate the device by moving the actuator in a substantially opposite direction (e.g., rotating in a counter-clockwise direction, moving in a proximal direction, and/or any other suitable movement). As such, the catheter can be retracted into the housing. In other words, a user can move the actuator to move and/or transition the catheter in a proximal direction to retract a distal end portion of the catheter into the housing (e.g., after use or the like).

Any of the aspects and/or features of the embodiments shown and described herein can be modified to affect the performance of the transfer device. For example, radius of curvature of a portion of an actuator can be increased or decreased to facilitate movement of a catheter coupled to and/or in contact with the portion of the actuator. In other embodiments, the length of the housing can be increased or decreased to accommodate the catheter having an increased or decreased length, respectively. By way of another example, any of the components of the transfer devices described herein can be formed from any suitable material that can result in a desired hardness, durometer, and/or stiffness of that component.

Where methods and/or schematics described above indicate certain events and/or flow patterns occurring in certain order, the ordering of certain events and/or flow patterns may be modified. Additionally, certain events may be performed concurrently in parallel processes when possible, as well as performed sequentially.

What is claimed:

1. An apparatus, comprising:
   a housing having a first port and a second port, the second port being coupleable to an indwelling vascular access device;
   a catheter having a proximal end portion and a distal end portion, the catheter at least partially disposed in the housing such that the proximal end portion is received by the first port; and
   an actuator partially disposed in the housing to selectively engage a portion of the catheter in the housing, the actuator configured to be rotated an angular distance relative to the housing to move the distal end portion of the catheter a linear distance from a first position in which the distal end portion of the catheter is disposed in the housing, to a second position in which the catheter extends through the second port such that the distal end portion of the catheter is distal to the indwelling vascular access device when the second port is coupled thereto, the linear distance being greater than the angular distance.

2. The apparatus of claim 1, wherein a portion of the housing has a circular cross-sectional shape.

3. The apparatus of claim 2, wherein each of the first port and the second port extend from a circumferential surface of the housing.

4. The apparatus of claim 3, wherein an axis defined by a lumen of the first port is substantially parallel to an axis defined by a lumen of the second port.

5. The apparatus of claim 1, wherein the proximal end portion of the catheter is coupled to the first port and maintained in a fixed position when the catheter is moved from the first position to the second position.

6. The apparatus of claim 1, wherein the actuator has a first engagement structure and a second engagement structure disposed in the housing, the portion of the catheter in the housing configured to extend from the first port, substantially wrap around each of the first engagement structure and the second engagement structure, and to the second port when the catheter is in the first position.

7. The apparatus of claim 6, wherein an inner surface of the first engagement structure and an inner surface of the second engagement structure define an inner channel therebetween, the portion of the catheter in the housing configured to extend from the first port, through the inner channel, and to the second port when the catheter is in the second position.

8. An apparatus, comprising:
a housing having a first port and a second port, the second port being coupleable to an indwelling vascular access device;
a catheter having a proximal end portion and a distal end portion, the catheter at least partially disposed in the housing such that the proximal end portion is received by the first port; and
an actuator partially disposed in the housing, the actuator defining an inner channel, the actuator and the housing collectively defining an outer channel, the actuator being rotatable relative to the housing to move the catheter between a first position and a second position different from the first position, the catheter in the first position extending within the housing from the first port, through the outer channel and the inner channel, and to the second port, the catheter in the second position extending within the housing from the first port, through the inner channel, and through the second port, wherein the actuator is configured to be rotated an angular distance relative to the housing to move the distal end portion of the catheter a linear distance when the catheter is moved from the first position to the second position: the linear distance being greater than the angular distance.

9. The apparatus of claim 8, wherein the distal end portion of the catheter is disposed in the housing when the catheter is in the first position and is distal to the indwelling vascular access device when the catheter is in the second position and the second port is coupled to the indwelling vascular access device.

10. The apparatus of claim 8, wherein a distance between the first port and the second port via the inner channel is less than the linear distance.

11. The apparatus of claim 8, wherein the proximal end portion of the catheter is fixedly coupled to the first port, the first port being coupled to a fluid reservoir via a secondary catheter, the secondary catheter being in fluid communication with the proximal end portion of the catheter.

12. The apparatus of claim 8, wherein the actuator has a first engagement structure and a second engagement structure disposed in the housing, the first engagement structure having an outer surface and an inner surface, the second engagement structure having an outer surface and an inner surface,
a first portion of the outer channel being defined between the outer surface of the first engagement structure and an inner surface of the housing, a second portion of the outer channel being defined between the outer surface of the second engagement structure and the inner surface of the housing, and
the inner channel being defined between the inner surface of the first engagement structure and the inner surface of the second engagement structure.

13. The apparatus of claim 12, wherein the catheter in the first position extends from the first port, through the first portion of the outer channel, through the inner channel, through the second portion of the outer channel, and to the second port.

14. The apparatus of claim 13, wherein the actuator is rotated between a first angular position and a second angular position, the actuator in the first angular position having an orientation relative to the housing such that the catheter extends through the inner channel from a position closer to the second port to a position closer to the first port.

15. The apparatus of claim 14, wherein the actuator in the second angular position having an orientation relative to the housing such that the catheter extends through the inner channel from the position closer to the first port to the position closer to the second port.

16. A method of using a fluid transfer device, the fluid transfer device including a housing with a first port and a second port, a catheter having a proximal end portion fixedly coupled to the first port, and an actuator selectively engaging the catheter, the method comprising:
coupling the second port of the fluid transfer device to an indwelling vascular access device;
rotating the actuator an angular distance about a central axis defined by the housing; and
advancing, in response to rotating the actuator, a distal end portion of the catheter a linear distance from a first position to a second position, the distal end portion of the catheter being in the housing when the catheter is in the first position, the distal end portion of the catheter being advanced linearly in a direction orthogonal to the central axis through the second port and the indwelling vascular access device as the catheter is moved to the second position, the distal end portion of the catheter being distal to the indwelling vascular access device when the catheter is in the second position, wherein the linear distance is greater than the angular distance.

17. The method of claim 16, wherein the actuator has a first engagement structure and a second engagement structure disposed in the housing, a portion of the catheter in the housing extending from the first port, substantially wrapping around each of the first engagement structure and the second engagement structure, and to the second port when the catheter is in the first position.

18. The method of claim 17, wherein an inner surface of the first engagement structure and an inner surface of the second engagement structure define an inner channel therebetween, the portion of the catheter in the housing configured to extend from the first port, through the inner channel, and to the second port when the catheter is in the second position.

19. The method of claim 18, wherein a distance between the first port and the second port via the inner channel is less than the linear distance.

20. The method of claim 16, wherein rotating the actuator the angular distance includes rotating the actuator 180° about the central axis from a first orientation relative to the housing to a second orientation relative to the housing.

21. The method of claim 16, further comprising:
supporting the portion of the catheter within the housing during the advancing of the distal end portion of the catheter the linear distance.

22. The method of claim 21, wherein the support is tangential to an axial force exerted along the portion of the catheter within the housing.

* * * * *